United States Patent
Narimatsu et al.

(10) Patent No.: US 7,241,605 B1
(45) Date of Patent: Jul. 10, 2007

(54) POLYPEPTIDE

(75) Inventors: Hisashi Narimatsu, Higashiyamato (JP); Soichiro Isshiki, Nakano-ku (JP); Akira Togayachi, Higashikurume (JP); Katsutoshi Sasaki, Machida (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/914,152

(22) PCT Filed: Feb. 24, 2000

(86) PCT No.: PCT/JP00/01070

§ 371 (c)(1),
(2), (4) Date: Aug. 24, 2001

(87) PCT Pub. No.: WO00/50608

PCT Pub. Date: Aug. 31, 2000

(30) Foreign Application Priority Data

Feb. 25, 1999 (JP) .................................. 11-047571

(51) Int. Cl.
*C12N 9/10* (2006.01)
(52) U.S. Cl. .............................. 435/193; 435/4; 435/6; 435/41; 435/97; 435/100; 435/101; 435/183; 435/252.3; 435/320.1; 435/325; 536/23.2; 536/23.4; 536/23.5; 800/8; 800/295
(58) Field of Classification Search ............... 435/69.1, 435/183, 193, 194, 252.3–259, 320, 325–372.3, 435/348, 4, 6, 320.1, 200; 530/350; 536/23.2–23.7, 536/24.31, 24.33; 800/8, 295
See application file for complete search history.

(56) References Cited

FOREIGN PATENT DOCUMENTS

| | | |
|---|---|---|
| JP | 6-181759 | 7/1994 |
| JP | 11-56373 | 3/1999 |
| WO | WO 00/29558 | 5/2000 |

OTHER PUBLICATIONS

Kyowa Hakko et al. (GenBank Accession No. AAQ67067, 1995).*
Isshiki et al. (J. Biol. Sci. vol., 274(18):12499-12507, Apr. 1999).*
Zhou D et al. (Eur. J. Biochem.vol. 263(2) :571-576).*
Varki, "Biological Roles of Oligosaccharides: all of the theories are correct", Glycobiology, vol. 3, No. 2 (1993), pp. 97-130.
Hannet, et al., "Genomic Cloning and Expression of Three Murine UDP-galactose: . . . ", The Journal of Biological Chemistry, vol. 273, No. 1 (1998), pp. 58-65.
Kolbinger, et al., "Cloning of Human UDP-galactose:2-Acetamido-2-deoxy-d-glucose . . . ", The Journal of Biological Chemistry, vol. 273, No. 1 (1998), pp. 433-440.
Amado, et al., "A Family of Human β3-Galactosyltransferases", The Journal of Biological Chemistry, vol. 273, No. 21 (1998), pp. 12770-12778.
Miyazaki, et al., "Expression of Cloning of Rat cDNA Encoding . . . ", The Journal of Biological Chemistry, vol. 272, No. 40 (1997), pp. 24794-24799.
Holmes, et al., "Synthesis of Type 1 and 2 LactoSeries Glycolipid . . . ", The Journal of Biological Chemistry, vol. 262, No. 32 (1997), pp. 15649-15658.
Holmes, "Characterization and Membrane Organization . . . " Archives of Biochemistry and Biophysics, vol. 270, No. 2 (1989), pp. 630-646.
Holmes, et al., "Preparative in Vitro Generation of Lacto-Series . . . ", Archives of Biochemistry and Biophysics, vol. 274, No. 1 (1989), pp. 14-25.
Kunz, et al., "Biological Functions of Oligosaccharides in Human Milk", Acta Paediatrica, vol. 82, pp. 903-912.
Prieto, et al., "Remodeling of Mouse Milk Glycoconjugates by . . . ", The Journal of Biological Chemistry, vol. 270, No. 49 (1995), pp. 29515-29519.
Zhou, et al., "Molecular Cloning of a Human . . . ", Eur. J. Biochem., vol. 263 (1999), pp. 571-576.
Isshiki, et al., "Cloning, Expression, and Characterization of a Novel . . . ", The Journal of Biological Chemistry, vol. 274, No. 18 (1999), pp. 12499-12507.
Bardoni, et al., "Differential expression of β1,3 galactosyltransferases in human . . . ", FEBS Letters, vol. 451 (1999), pp. 75-80.
Zhou, et al., "A β-1,3-N-acetylglucosaminyltransferase with . . . ", Proc. Natl. Acad. Sci., vol. 96, (1999), pp. 406-411.
Rump, et al., "Homo sapiens chromosome 21", Database accession No. AF064860 (XP002267032) Jun. 2, 1998.
Zhou, et al., "Homo sapiens B3GALT5 gene", Database accession No. AF145784 (XP002267034) Nov. 15, 1999.
Ishhiki, et al., "Homo sapiens mRNA for UDP-Gal:GlcNAc . . . ", Database accession No. AB020337.1 (XP002267033) May 17, 1999.

* cited by examiner

*Primary Examiner*—Manjunath Rao
(74) *Attorney, Agent, or Firm*—Fitzpatrick, Cella, Harper & Scinto

(57) ABSTRACT

According to the present invention, there can be provided a novel polypeptide having β1,3-galactosyltransferase activity involved in the synthesis of type 1 sugar chains, a DNA coding for said polypeptide, a recombinant vector comprising said DNA, a transformant carrying said recombinant vector, a process for producing type 1 sugar chain-containing sugar chains and complex carbohydrates by use of said polypeptide or said transformant, an antibody recognizing said polypeptide, a method for detecting or quantifying said polypeptide by use of said antibody, a method for screening a substance correlated with said polypeptide, a method for diagnosis or treatment of cancers in the digestive system by use of said DNA or said antibody, and a method for treatment of cancers in the digestive system by use of a substance obtained by said screening method.

30 Claims, 6 Drawing Sheets

A

B

C

SEQUENCE LISTING

```
<160> NUMBER OF SEQ ID NOS: 44

<210> SEQ ID NO 1
<211> LENGTH: 310
<212> TYPE: PRT
<213> ORGANISM: Homo sapiens

<400> SEQUENCE: 1

Met Ala Phe Pro Lys Met Arg Leu Met Tyr Ile Cys Leu Leu Val Leu
  1               5                  10                  15

Gly Ala Leu Cys Leu Tyr Phe Ser Met Tyr Ser Leu Asn Pro Phe Lys
             20                  25                  30

Glu Gln Ser Phe Val Tyr Lys Lys Asp Gly Asn Phe Leu Lys Leu Pro
         35                  40                  45

Asp Thr Asp Cys Arg Gln Thr Pro Pro Phe Leu Val Leu Leu Val Thr
     50                  55                  60

Ser Ser His Lys Gln Leu Ala Glu Arg Met Ala Ile Arg Gln Thr Trp
 65                  70                  75                  80

Gly Lys Glu Arg Met Val Lys Gly Lys Gln Leu Lys Thr Phe Phe Leu
                 85                  90                  95

Leu Gly Thr Thr Ser Ser Ala Ala Glu Thr Lys Glu Val Asp Gln Glu
            100                 105                 110

Ser Gln Arg His Gly Asp Ile Ile Gln Leu Asp Phe Leu Asp Val Tyr
        115                 120                 125

Tyr Asn Leu Thr Leu Lys Thr Met Met Gly Ile Glu Trp Val His Arg
    130                 135                 140

Phe Cys Pro Gln Ala Ala Phe Val Met Lys Thr Asp Ser Asp Met Phe
145                 150                 155                 160

Ile Asn Val Asp Tyr Leu Thr Glu Leu Leu Lys Lys Asn Arg Thr
                165                 170                 175

Thr Arg Phe Phe Thr Gly Phe Leu Lys Leu Asn Glu Phe Pro Ile Arg
```

-continued

```
                    180             185                 190
Gln Pro Phe Ser Lys Trp Phe Val Ser Lys Ser Glu Tyr Pro Trp Asp
            195                 200                 205

Arg Tyr Pro Pro Phe Cys Ser Gly Thr Gly Tyr Val Phe Ser Gly Asp
        210                 215                 220

Val Ala Ser Gln Val Tyr Asn Val Ser Lys Ser Val Pro Tyr Ile Lys
225                 230                 235                 240

Leu Glu Asp Val Phe Val Gly Leu Cys Leu Glu Arg Leu Asn Ile Arg
                245                 250                 255

Leu Glu Glu Leu His Ser Gln Pro Thr Phe Pro Gly Gly Leu Arg
            260                 265                 270

Phe Ser Val Cys Leu Phe Arg Arg Ile Val Ala Cys His Phe Ile Lys
            275                 280                 285

Pro Arg Thr Leu Leu Asp Tyr Trp Gln Ala Leu Glu Asn Ser Arg Gly
        290                 295                 300

Glu Asp Cys Pro Pro Val
305                 310
```

```
<210> SEQ ID NO 2
<211> LENGTH: 2775
<212> TYPE: DNA
<213> ORGANISM: Homo sapiens
<220> FEATURE:
<221> NAME/KEY: CDS
<222> LOCATION: (402)..(1331)

<400> SEQUENCE: 2
```

| | |
|---|---|
| gtgaattcct ctttctctgc tggagctggg atattcttct tctcctgccc ttggacatca | 60 |
| gagctgcagg ctctctggcc tttggacccg aggattata ccaagcaggt ttctgggttc | 120 |
| tcaggccttt ggccttggac tgatagttac accattggca tatctggttc tgaggctctt | 180 |
| ggtcttggac tgagccacac tcctggcatc ccagcgtctc cagcttgcat ggcctgtcac | 240 |
| gtgattcctg tcagaatcac cattttggt aaacaaacca agcccagaac tgataatta | 300 |
| tggagcattc tacactgaca gttctttgag acaaatttcc tcttggcatt tacactgtgg | 360 |

```
ctttagcttt caaaccagag gttcctctta cccagcaaaa a atg gct ttc ccg aag       416
                                            Met Ala Phe Pro Lys
                                            1               5 atg aga ttg atg tat att tgc ctt ctg gtt ctg ggg gct ctt tgt ttg        464
Met Arg Leu Met Tyr Ile Cys Leu Leu Val Leu Gly Ala Leu Cys Leu
            10                  15                  20 tat ttt agc atg tac agt cta aat cct ttc aaa gaa cag tcc ttt gtt        512
Tyr Phe Ser Met Tyr Ser Leu Asn Pro Phe Lys Glu Gln Ser Phe Val
        25                  30                  35 tac aag aaa gac ggg aac ttc ctt aag ctc cca gat aca gac tgc agg        560
Tyr Lys Lys Asp Gly Asn Phe Leu Lys Leu Pro Asp Thr Asp Cys Arg
    40                  45                  50 cag aca cct ccc ttc ctc gtc ctg ctg gtg acc tca tcc cac aaa cag        608
Gln Thr Pro Pro Phe Leu Val Leu Leu Val Thr Ser Ser His Lys Gln
55                  60                  65 ttg gct gag cgc atg gcc atc cgg cag acg tgg ggg aaa gag agg atg        656
Leu Ala Glu Arg Met Ala Ile Arg Gln Thr Trp Gly Lys Glu Arg Met
70                  75                  80                  85 gtg aag gga aag cag ctg aag aca ttc ttc ctc ctg ggg acc acc agc        704
Val Lys Gly Lys Gln Leu Lys Thr Phe Phe Leu Leu Gly Thr Thr Ser
                90                  95                 100 agt gca gcg gaa acg aaa gag gtg gac cag gag agc cag cga cac ggg       752
Ser Ala Ala Glu Thr Lys Glu Val Asp Gln Glu Ser Gln Arg His Gly
```

-continued

```
                     105                 110                 115
gac att atc cag aag gat ttc cta gac gtc tat tac aat ctg acc ctg     800
Asp Ile Ile Gln Lys Asp Phe Leu Asp Val Tyr Tyr Asn Leu Thr Leu
            120                 125                 130 aag acc atg atg ggc ata gaa tgg gtc cat cgc ttt tgt cct cag gcg     848
Lys Thr Met Met Gly Ile Glu Trp Val His Arg Phe Cys Pro Gln Ala
135                 140                 145 gcg ttt gtg atg aaa aca gac tca gac atg ttc atc aat gtt gac tat     896
Ala Phe Val Met Lys Thr Asp Ser Asp Met Phe Ile Asn Val Asp Tyr
150                 155                 160                 165 ctg act gaa ctg ctt ctg aag aaa aac aga aca acc agg ttt ttc act     944
Leu Thr Glu Leu Leu Leu Lys Lys Asn Arg Thr Thr Arg Phe Phe Thr
            170                 175                 180 ggc ttc ttg aaa ctc aat gag ttt ccc atc agg cag cca ttc agc aag     992
Gly Phe Leu Lys Leu Asn Glu Phe Pro Ile Arg Gln Pro Phe Ser Lys
            185                 190                 195 tgg ttt gtc agt aaa tct gaa tat ccg tgg gac agg tac cca cca ttc    1040
Trp Phe Val Ser Lys Ser Glu Tyr Pro Trp Asp Arg Tyr Pro Pro Phe
            200                 205                 210 tgc tcc ggc acc ggc tac gtg ttt tct ggc gac gtg gcg agt cag gtg    1088
Cys Ser Gly Thr Gly Tyr Val Phe Ser Gly Asp Val Ala Ser Gln Val
215                 220                 225 tac aat gtc tcc aag agc gtc cca tac att aaa ctg gaa gac gtg ttt    1136
Tyr Asn Val Ser Lys Ser Val Pro Tyr Ile Lys Leu Glu Asp Val Phe
230                 235                 240                 245 gtg ggg ctc tgc ctc gaa agg ctg aac atc aga ttg gag gag ctc cac    1184
Val Gly Leu Cys Leu Glu Arg Leu Asn Ile Arg Leu Glu Glu Leu His
            250                 255                 260 tcc cag ccg acc ttt ttt cca ggg ggc tta cgc ttc tcc gta tgc ctc    1232
Ser Gln Pro Thr Phe Phe Pro Gly Gly Leu Arg Phe Ser Val Cys Leu
            265                 270                 275 ttc agg agg atc gtg gcc tgc cac ttc atc aag cct cgg act ctc ttg    1280
Phe Arg Arg Ile Val Ala Cys His Phe Ile Lys Pro Arg Thr Leu Leu
            280                 285                 290 gac tac tgg cag gct cta gag aat tcc cgg ggg gaa gat tgt ccg cct    1328
Asp Tyr Trp Gln Ala Leu Glu Asn Ser Arg Gly Glu Asp Cys Pro Pro
            295                 300                 305 gtc tgaggggagc ccagaggcac atccggacaa gtttcagata acccgtgggg         1381
Val
310 atagttttg ctagattttg gaagagggg cgggacagag gatgctgttc ttcagtgctg    1441
aaatccacgc cagaatgtcg gtgttcatga agtcactgat tagttcccac ttggtgcccc  1501
aggcaataat aggcccgtct cttgggcacg cacactcttc atactaagtg tttgacatac  1561
acctggattt ttgcatttca ggggtcagta tcctatgaca tgatgggtgt taccatccta  1621
attttacagg caaggacaca gcagctgcga gaggtacaga aacttgtccc aaggctcaca  1681
gccagtaggc ataggagcgg gaatgaaaat cgagcactgt cagaatctgg tgggcagccc  1741
ctgacttgaa ccactcccac gtgctgcctc ccttaggagg ggacactgat gatgaggtct  1801
cggagccggc atccttccat ccctgtcgag tccctccac ctcagctccc agtccttgtg   1861 cttttttggag ctaagcctgg gatgaccaaa ttcaccccag ctccttcatt cacagggctg 1921 gatgtagctg ggattgagtc catgttatcg gctcggtact caacacaacc caagtttcat  1981
ccgaggaaat gtccccgcag tggatgcagc tcacatgctg aggaacaccc agctctggac  2041
agagttctta taaatgtata aattaggctc agaaaccact gcattctgac ctgctgtaca  2101
gactgcccac actgctgacc tgcctagcga gcaggacatc ccttctgagc catctgctgc  2161
```

-continued

```
tctctcattt catcacccca actgtccctt gttttttgatc aatggggacc agccactgcc    2221
ccaggagcac tttagggctc tcagttcaaa ctgaaggaca gttgaactca gatggggttc    2281
atgtgggatt ctgggagctt tctgggaatt cagttggagt caagtcagga tgctctcaag    2341 gaccctcgg gctcagagcc ctaaagtggg ccctggtgaa gcaggtggt cctgcgtcca      2401 cttcccaagc ctgagccaag ctcatcttca ttgaatgtct catttggccg aggaacaact    2461
gaactttgtg gtttgctgtt tagccttcag tttgctccgc tgcctcctac ccagaggttt    2521
gtgcgagcct gtgttgcagg gttgtataaa accaaggtac ttcgttagtt ttgcccattc    2581
agccatggtc acgtgacatg caaagtaatc ttgctcctaa ttatagaaat gattttttctt   2641 ttaattttttt actttaccag actttacttt gtactcagag aagaggcctc acatggctgt   2701
gtcacatata aatgttggac taaactctta aaaaaaaaaa aaaaaaaaaa aaaaaaaaaa    2761
aaaaaaaaaa aaaa                                                       2775
```

<210> SEQ ID NO 3
<211> LENGTH: 10562
<212> TYPE: DNA
<213> ORGANISM: Homo sapiens
<220> FEATURE:
<221> NAME/KEY: promoter
<222> LOCATION: (1)..(5000)
<220> FEATURE:
<221> NAME/KEY: exon
<222> LOCATION: (5001)..(5140)
<220> FEATURE:
<221> NAME/KEY: exon
<222> LOCATION: (5001)..(5273)
<220> FEATURE:
<221> NAME/KEY: exon
<222> LOCATION: (5459)..(5567)
<220> FEATURE:
<221> NAME/KEY: exon
<222> LOCATION: (7427)..(7586)
<220> FEATURE:
<221> NAME/KEY: exon
<222> LOCATION: (8234)..(10562)

<400> SEQUENCE: 3

```
cgcctctggc aaggtagacc ttgaaggcaa aactgagttg aggtttgtta ggacggaaat     60
aattactgct gggcatgcag cacttcccaa ccgttctgtg aggcaggcag tgttattgcc    120
agtttggcac aagggcacag gtgtagaaca cgtaagtgcc ctgggccgtg ctacaccacc    180
actgtgtttg agctgagatg tgaaccaggg ccttctgatt ccaaattcct cattcctttc    240
atcctagcag gctgcctgcg gttagcagaa ggggactcct gtatctgctc tgcagcttct    300
tcagctgatt tataatggaa acagagtag atattgattt ggcaattagt gaaatattat     360
gagaatcatc atagcaaact tcacagtttg atcaaggatc ctgccttcaa tatctggcca    420
actgatgtgt aaaagcagct gcaagaactt cagagctgac aaaaaaagca aactccagac    480
tttatttcct ggaatctgtt ttgtgagaca ctggcccatg aaatgctctc ccagaaatag    540
tcggatttgt ggtcaaataa atttgggcaa ttctacagaa catgtgtctt tttcagagat    600
ttatttttaa ttaaacttat ttaaaaatat taacatggta caatttgcat atagtgaagt    660
gtgcaaatct tcgctacatg gctcaatgag tttttacata tatttccacc catgtaatca    720
ccaccgagat ctagaataga atgtattcgt ctctccagag gttcctctgt tcccttgcag    780
tcaataattc tccaccaaag ataaacattc tgctgacttc cttcatcatt gataagtttt    840
tcctggtttt gaacttcata taaatggaat catttcatgt ctagctcttt tcactcaaca    900
```

-continued

| | |
|---|---|
| taacatctgt cagattaata catcgcatgt caatagtttg tagtttttat ggctgtgtag | 960 |
| catttcattc attcattctg ctgttgatgg aaatttcttg actagagttg tgttatcaat | 1020 |
| ttattgcctc ttggctccaa attcacccct tttgcctggt ctctggaaat gggtctgggc | 1080 |
| cctctaaata ttttcccttt gcaatctggc tcttgaagct tatcagtgga gggtcctgga | 1140 |
| ggggcattgc aggggaaaca gttttccctt cctggttcag ggacgctggt ttggtagccc | 1200 |
| ctgtggtgtt acaggagtac ttggcaagac agcagtttcc ccgggtacac ccgctaggtg | 1260 |
| ttttgtagca gagtgcatct gtgagacaac tggtgaactg ctttccttgc aacctagagg | 1320 |
| gcagatttct ggcaagttcc agagggtgga ttccaaacat gttcctctaa tgtggatctg | 1380 |
| cagtgatgtc tctgccattc agtgggcata gctgtgccct tttagtgggg tctagatctc | 1440 |
| agccctggga ttgggggcat tttctcagtt gctcaatctc agccctaggg gcagtgacca | 1500 |
| ttccttatat atggttgttt gtatattctt tggaactgtc ttgattttat tactgttagt | 1560 |
| ctctcattac tccactccct tattatagta aatgattctt tgtatttgac tttccctggt | 1620 |
| caaggtacta agtggttttt ctctcctgtt tggatctaga ttgatacaat aatttttgc | 1680 |
| aattatgagc aatgctgctg tgaacattct tgatcatgtc ttagtggaca taagcaataa | 1740 |
| ttgctgctgg gtctgtgtgc aggaatgatt tgctagatca tagcacatac gtttatctgt | 1800 |
| agcagaaact gccaaggtat atacagcttt ccaaagtgtg ttaatttaca tgcctgctag | 1860 |
| caaggtagga gaaatacagt tgcttcccaa gtagctggga ttacaggtgt gtgccaccac | 1920 |
| tcctggctaa ttttttgtag atagggtt ttgccatgtt ggccaggcta gtcttgaact | 1980 |
| gctggcctca agtgatctgc ctgccttggg ctcccaaagt gctaggatta cagggatgag | 2040 |
| ccaccatggt cgacttcatg ataaaacttc agtggatgag gagctgcctc ttatgatgaa | 2100 |
| caaagaaggt ggtttcttga aatggaatct actcctggtg aagatgctgt gaacattgtt | 2160 |
| gaaatgacaa gaaagaattt acagtgttac atagagttag ttgatgaagc agtagcagga | 2220 |
| ttcgagagga tcgattccaa tttcaaaata agttcttctg tgggtaaaat gctatcaaat | 2280 |
| ggcgtcgcat gctacagaga aatctatcat gaaaggaaga gtcaattgat gtggcaaact | 2340 |
| tcattgttgt cgtatttaa gaaattgtca ggaccacccc aaccttcaac aaccatgacc | 2400 |
| ctgatcagtc aggagccatc cacattgagg cgagaacctc cagcagtaaa aagattatga | 2460 |
| ttctctaaag gatcagatga acattagcat tttttaagc aataaagtat ttttacgtaa | 2520 |
| gatatgtatg ttattttta ggcataatgc tattatgcat ttaatagact ccagtatatt | 2580 |
| gtaaacataa ctttaaatgc actgggagat aaaagtattt gctcttttat gatatttgct | 2640 |
| ttattgcagt agtctgtaat ggaaactaca ttatctcttg ggtacacctg tatacagaaa | 2700 |
| gaaatttatc atgaggaaat gctcatgcaa tgatggaggc tggaaagtcc caagatctgc | 2760 |
| agtcagcaag ttggagaccc atgagagtcg atggtgtggc cccagtctgt gtttgaaggc | 2820 |
| ctgagaacca ggagagccaa aagctggcaa gctctggacc caggaagagc tgatgtttca | 2880 |
| gttcaagtcc gaaggcagga aaagactgaa ggcccagctc caggcagtca ggcaggagaa | 2940 |
| ctttcctttt actcacgaga gggtcagcat tttgttctgt tcaggctgtc aactgagtga | 3000 |
| cccagaaaag ctggcacata acattcacca tcgtgctgca agagctgcaa aaccctctct | 3060 |
| gcttctaaca ctgatgctca gcccacctcc agtgggcagg gagctgggtg ccggaggac | 3120 |
| ttggggttgc cagcccagtg tgggcctgga cagttgctga aatctccct ccgccctgtg | 3180 |
| acttcttaat tacttagagg gtcacccctgg ttgctcactt cagctcactt gggagattct | 3240 |
| ctctgcttga ggccaggggt aggtccaggt ctgatggggt ctgaagctta tacaattggg | 3300 |

```
gtgggggca   ttcctctta   aggaaaagaa   aacagcagag   gtgagtcgtc   ctgcagctta   3360
gcttcactag  tctcgtggaa  aatttgcctc   ctaaaatgtc   tttcctctga   gaaagcccag   3420
gcctccaaag  gcccagccag  gctggcgtca   gtctggggtc   agctgcgggg   aggctccagg   3480
ccatgtgtga  cacgggagtt  taccccatcc   cagtttccag   tggagaagca   tcgttctcgt   3540 ccaccccgt   catgctcttt  tccaccttct   ccaggggaag   ggatattttc   agtctgtaca   3600
acgaatccac  tgaaatgtta  aggtgggcac   agtggtctgg   ggtcttcgac   cttgtttata   3660
cgtggtgcct  gttactggtc  gggtctgtac   aggcagtttc   cactggcgtt   ttttaccagg   3720
ccagcctaga  gtagaatgac  cgcatgttaa   aatatagatt   cctgggcccc   agacctgcca   3780
gaatctctgt  gagatggaac  ctttcaacct   gggttttaaa   caagcctccc   gggtgattct   3840
gacactcact  ggatttgaga  accgtggggt   tgttcagaca   gcagggacgt   tgatgttgtt   3900
ccttctgcgt  tcctggtgat  gctgttctgt   tctcccaagg   cctatgcggt   ggtgagaatc   3960
tccaaggata  caagacagtg  atctggagcg   agtgtcctga   aagcagactc   tagcactcag   4020
gactgccaac  ccctccccg   ggtttccttg   gtctggaatt   cccatcccct   ggttccacct   4080
gttacatcac  acctcccctt  caaggaccag   tgcagatgcc   acgtccttca   cggggctcag   4140
aatgctcacc  agcttcctct  ccaccgaggg   ccacagcccc   tggagacccc   ttgagctgag   4200
tgctttgtcc  ttgcatactc  tttctggcct   catagtgggg   cttggccatt   gtcccttcac   4260
tccagatctc  tccttcagg   tccaggaagt   gcatcttgaa   cttaactttc   cagacccccc   4320
cttcagtttt  ccagtcctta  gagaggtgga   cttctgattc   ctttgtctct   gtgccctgta   4380
gcctcaggtc  aggcttaagg  caaggtctcc   tcacctggcc   tggggagagt   cccaggacgc   4440
tgcacgtgcc  tgtgcgggta  ggatgctgat   gcccagattt   cccgttagag   agcctttccc   4500
tatcctgacg  gctctagctt  tgtgtgttac   ttacttgttc   cactttaatt   caaaatgtac   4560
ccagcaacca  gcttgtgcac  agttctctgg   ggtttcagga   gggatgtaag   acatacccct   4620
tgcccttcag  gcactatggc  cagaaggggg   gcagtgacct   aggcagaggg   cgggagccag   4680
cagatgggat  acactcagag  gagcctgcag   caggcagagg   cagaggagaa   gggaggtcta   4740
cacgttctgc  actgtattta  tctccttcag   ttccaaggtt   ctctcctggc   atctatattg   4800
ctcatgagtt  acagagcaaa  gcctggtgtg   atggttactt   taggtgtca   acttggctgg   4860 attaataaat  acctagagaa  ctggtaaagc   attatttctg   ggtgtgtttg   tgaaggtgtt   4920
tccagaggag  attggctgtg  agtcagtggg   ctgagtgggg   aggagctgcc   ctccatgtgg   4980
gcaggcacca  tccattgact  gggcccagat   agaacaagaa   ggcagaagaa   atgtgaattc   5040
ctctttctct  gctggagctg  ggatattctt   cttctcctgc   ccttggacat   cagagctgca   5100
ggctctctgg  cctttggacc  cgaggattta   taccaagcag   gtttctgggt   tctcaggcct   5160
ttggccttgg  actgatagtt  acaccattgg   catatctggt   tctgaggctc   ttggtcttgg   5220
actgagccac  actcctggca  tcccagcgtc   tccagcttgc   atggcctgtc   acggtatttc   5280
ccaacctccg  taatcacgct  agccaattct   tctaagaaat   ttcttctcat   ctatctgtct   5340
gtctatctat  ctatctgtct  acctaccgac   ttacctacct   acctgcctat   ctatcttttg   5400
attaatctac  ctatcaatct  ttctatctat   ccataacctg   ttgattcgat   ctctctagag   5460
aaccctgact  aatacacctg  gagtgcagaa   tctgctggag   aaactgccat   tccgttattg   5520
actggctggt  caggccatac  agcctggtgg   tctagatgtg   tttggaggta   gggcttctgt   5580
agcacagata  gtgcctgttc  atggctctgt   cccaggtaag   gcagagctag   cttgtgctga   5640
```

-continued

| | | | | |
|---|---|---|---|---|
| gggcttctgc | tttgcagctg | gcctggggtg | gctaggatct | ggggacacag gctgcccttt | 5700 |
| ccaggctctg | tctgctggtg | ctgcaggtgc | cctacctcc | tccttcagtg gaaggctggc | 5760 |
| ccccaggtcc | tctttaggcc | caatacagac | tcagccaaag | atgcagatgt ctcatatatg | 5820 |
| aggattctga | gctgtgactt | ctggtggtaa | ctccacttta | ggcaggaaaa atgttcaact | 5880 |
| gcccatgaaa | acaaatgacc | ccgggtcatt | tgggtttggc | acctgctctg ccagttgggt | 5940 |
| ttggcacctg | ctctgcctcc | tgggaaacag | tttggccaat | gcactgcatg aggtgagcgc | 6000 |
| ccatccctgg | gaattagag | ccctgtgaag | ggtcctgagg | agaggcacat cagagagaat | 6060 |
| gagaatttaa | ggtttactgt | taaagcaacc | catagaaaag | gagcagaatt attcaagcaa | 6120 |
| ggaaacaaag | tagaaaaata | tcttctttcc | cttgcacttg | gtttttatgt ttctctctaa | 6180 |
| aatgtattgt | gggggagaaa | gcagtccccc | aacccccta | atcagctgca tatcttagcc | 6240 |
| atgcaaataa | ataatgaaag | agagaaagaa | ggagagaaag | agaaagaaaa gtaaaggaag | 6300 |
| gaaggagaga | aggaaggaaa | gaaagaaag | aaagaaagaa | actttgcagc atcctggagc | 6360 |
| accagttcag | acaagttctg | gtctcctgct | tgccttctgc | tgtgatttct ctgaagttgc | 6420 |
| tgggggcagg | agctgggcag | gaactcccca | ggggtgccaa | gcagagcagg tagttggcta | 6480 |
| agtttgcctc | caggaaagaa | gtccctggag | agcgagctgg | ttctagaaag ctccattatt | 6540 |
| atattcctat | tgcttttggc | gaatatatgt | agaacagaat | tttgacaatg aaattttcag | 6600 |
| gtgctctttt | ggccatcaaa | ataaccagct | cttggctggg | cacagtggct tgcccttgta | 6660 |
| attccagtgt | tttgggaggc | caaggcaggg | gactgcgtga | gcccaggagt ttgagactag | 6720 |
| cctgggcaac | atagtgaaac | cccatctcta | caaaaatac | aaagttagaa gagtatggtg | 6780 |
| gcatgcgcct | gtggtcacag | ctacttggga | agctgtgacc | caagtcacag gaggatcgct | 6840 |
| tgagcccagg | agttcagggc | tgtagtgagc | tatgattgtg | ctactgtgct ccagcctggg | 6900 |
| agacagagtg | acatcaggtc | tctgaaatat | taaaattaaa | aagcccaaac caactctgct | 6960 |
| tttcactctt | tcagtttcat | ttcttgctgt | cctctctgtc | ctctcaccca gggtaacatt | 7020 |
| tttaaagtgc | cgctattgtg | ttaagaattg | gatttattct | ctgtgttaaa ttctctcagc | 7080 |
| attaactaca | gactctgtta | tgtaaataag | gtaaattatc | aggatgagaa gtgagactct | 7140 |
| aatttatgag | tttatcatgt | ctcttttaaaa | agctgctagg | tgctatccta acttattagg | 7200 |
| cttgaaggat | tctgggggat | tggcatattg | ttactgttgt | ggactttgtt tgccttgatc | 7260 |
| atacccattt | tacagatgag | aaaagtgagg | ctgggattgg | ggctcaaatg cgtgctcaga | 7320 |
| gtcacataag | taggttggaa | ggtgacgcta | cagacacggt | aaattgtgaa ggcctgctgg | 7380 |
| taaggcacga | gtgatttgaa | tgacactctt | tttttttttt | tcctagtgat tcctgtcaga | 7440 |
| atcaccattt | ttggtaaaca | aaccaagccc | agaacctgat | aattatggag cattctacac | 7500 |
| tgacagttct | ttgagacaaa | tttcctcttg | gcatttacac | tgtggcttta gctttcaaac | 7560 |
| cagaggttcc | tcttacccag | caaaaagtga | gttatacgct | ttcttaatgt tataacgtta | 7620 |
| ccatggatga | tcctgaactt | gccgaggata | gcagagacgg | gtgggcagaa caggaaagaa | 7680 |
| tcagatcaga | gactgtaaaa | agtaacttaa | aaaaaaataa | ttctggcaga gacagaattt | 7740 |
| gaaggtactt | gtgcacatca | gaacactgga | cttgcttttt | tctgggagca ggaatgctgc | 7800 |
| ttaattagat | cagagaagaa | tgcaagtggt | ccatacattt | agatctacaa tgcgtggttt | 7860 |
| ccagacctgc | agcttgtttt | gctgcgcttc | atcatggagt | catagaaggg cagagctgga | 7920 |
| ggaccgagtg | agggacctgg | tgccatatcc | ctacagacag | gcaattggag actcccgtag | 7980 |
| gttaagggct | gcagagcctg | gaccaatgcc | cagaatctct | gagcttttta tcttacacca | 8040 |

```
tgaagtgaca gatgctggca gatgttagac ctttgtgctt aactgtttaa ccacacagca    8100
cccgacttct gtatgcagcg aggttctaga gtttccaaaa cacgggtctc ctctcccacc    8160
tcagcctcct agcataaaac tagacacatc ctcatgcttt tgaggtctaa tcattggatt    8220
ttgttccttt cagatggctt tcccgaagat gagattgatg tatatttgcc ttctggttct    8280
gggggctctt tgtttgtatt ttagcatgta cagtctaaat cctttcaaag aacagtcctt    8340
tgtttacaag aaagacggga acttccttaa gctcccagat acagactgca ggcagacacc    8400
tcccttcctc gtcctgctgg tgacctcatc ccacaaacag ttggctgagc gcatggccat    8460
ccggcagacg tgggggaaag agaggatggt gaagggaaag cagctgaaga cattcttcct    8520
cctggggacc accagcagtg cagcggaaac gaaagaggtg gaccaggaga gccagcgaca    8580
cggggacatt atccagaagg atttcctaga cgtctattac aatctgaccc tgaagaccat    8640
gatgggcata gaatgggtcc atcgcttttg tcctcaggcg gcgtttgtga tgaaaacaga    8700
ctcagacatg ttcatcaatg ttgactatct gactgaactg cttctgaaga aaaacagaac    8760
aaccaggttt tcactggct tcttgaaact caatgagttt cccatcaggc agccattcag     8820
caagtggttt gtcagtaaat ctgaatatcc gtgggacagg tacccaccat tctgctccgg    8880
caccggctac gtgttttctg cgacgtggc gagtcaggtg tacaatgtct ccaagagcgt     8940
cccatacatt aaactggaag acgtgtttgt ggggctctgc ctcgaaaggc tgaacatcag    9000
attggaggag ctccactccc agccgacctt ttttccaggg ggcttacgct tctccgtatg    9060
cctcttcagg aggatcgtgg cctgccactt catcaagcct cggactctct tggactactg    9120
gcaggctcta gagaattccc gggggaaga ttgtccgcct gtctgagggg agcccagagg     9180
cacatccgga caagtttcag ataacccgtg gggatagttt ttgctagatt ttggaagagg    9240
gggcgggaca gaggatgctg ttcttcagtg ctgaaatcca cgccagaatg tcggtgttca    9300
tgaagtcact gattagttcc cacttggtgc cccaggcaat aataggcccg tctcttgggc    9360
acgcacactc ttcatactaa gtgtttgaca tacacctgga ttttgcatt tcagggtca     9420
gtatcctatg acatgatggg tgttaccatc ctaattttac aggcaaggac acagcagctg    9480
cgagaggtac agaaacttgt cccaaggctc acagccagta ggcataggag cgggaatgaa    9540
aatcgagcac tgtcagaatc tggtgggcag cccctgactt gaaccactcc cacgtgctgc    9600
ctcccttagg aggggacact gatgatgagg tctcggagcc ggcatccttc catccctgtc    9660
gagtcccctc cacctcagct cccagtcctt gtgcttttg gagctaagcc tgggatgacc     9720
aaattcaccc cagctccttc attcacaggg ctggatgtag ctgggattga gtccatgtta    9780
tcggctcggt actcaacaca acccaagttt catccgagga aatgtccccg cagtggatgc    9840
agctcacatg ctgaggaaca cccagctctg gacagagttc ttataaatgt ataaattagg    9900
ctcagaaacc actgcattct gacctgctgt acagactgcc cacactgctg acctgcctag    9960
cgagcaggac atcccttctg agccatctgc tgctctctca tttcatcacc ccaactgtcc   10020
cttgttttg atcaatgggg accagccact gccccaggag cactttaggg ctctcagttc    10080
aaactgaagg acagttgaac tcagatgggg ttcatgtggg attctgggag ctttctggga   10140
attcagttgg agtcaagtca ggatgctctc aaggacccct cgggctcaga gccctaaagt   10200
gggccctggt gaagcagggt ggtcctgcgt ccacttccca agcctgagcc aagctcatct   10260
tcattgaatg tctcatttgg ccgaggaaca actgaacttt gtggtttgct gtttagcctt   10320
cagtttgctc cgctgcctcc tacccagagg tttgtgcgag cctgtgttgc agggttgtat   10380
```

```
aaaaccaagg tacttcgtta gttttgccca ttcagccatg gtcacgtgac atgcaaagta    10440
atcttgctcc taattataga aatgattttt cttttaattt tttactttac cagactttac    10500
tttgtactca gagaagaggc ctcacatggc tgtgtcacat ataaatgttg gactaaactc    10560
tt                                                                   10562
```

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 4
ttcagccacc taacagttgc cagg                                            24

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 5
ataccttctt cgtggcttgg tggag                                           25

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 6
tagaagctag aagagctatt cggc                                            24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 7
actcgccagt gattgaacac aaac                                            24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 8
cccaatgcca agtacgtaat gaag                                            24

<210> SEQ ID NO 9
<211> LENGTH: 24
<212> TYPE: DNA
<213> ORGANISM: Artificial Sequence
<220> FEATURE:

```
<223> OTHER INFORMATION: Description of Artificial Sequence: synthetic
      DNA

<400> SEQUENCE: 9
tgtggtgttc cttagcatga cctg                                          24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 10
ttgatcccca accaggaagc ttgc                                          24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 11
tgaggccact gctcctctga tacg                                          24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 12
gatatcgccg cgctcgtcgt cgac                                          24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 13
caggaaggaa ggctggaaga gtgc                                          24

<210> SEQ ID NO 14
<211> LENGTH: 11
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 14
ctttagagca c                                                        11

<210> SEQ ID NO 15
<211> LENGTH: 8
<212> TYPE: DNA
<213> ORGANISM: Artificial Sequence
<220> FEATURE:
<223> OTHER INFORMATION: Description of Artificial Sequence: synthetic
```

DNA

<400> SEQUENCE: 15 ctctaaag                                                              8

<210> SEQ ID NO 16
<211> LENGTH: 20
<212> TYPE: DNA
<213> ORGANISM: Artificial Sequence
<220> FEATURE:
<221> NAME/KEY: modified_base
<222> LOCATION: (3)
<223> OTHER INFORMATION: i
<220> FEATURE:
<221> NAME/KEY: modified_base
<222> LOCATION: (9)
<223> OTHER INFORMATION: i
<220> FEATURE:
<221> NAME/KEY: modified_base
<222> LOCATION: (15)
<223> OTHER INFORMATION: i
<220> FEATURE:
<223> OTHER INFORMATION: Description of Artificial Sequence: synthetic
      DNA

<400> SEQUENCE: 16
gcnathmgnc aracntgggg                                                20

<210> SEQ ID NO 17
<211> LENGTH: 24
<212> TYPE: DNA
<213> ORGANISM: Artificial Sequence
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (15)
<223> OTHER INFORMATION: i
<220> FEATURE:
<221> NAME/KEY: modified_base
<222> LOCATION: (21)
<223> OTHER INFORMATION: i
<220> FEATURE:
<223> OTHER INFORMATION: Description of Artificial Sequence: synthetic
      DNA

<400> SEQUENCE: 17
taygtnatga aracngaytc ngay                                           24

<210> SEQ ID NO 18
<211> LENGTH: 24
<212> TYPE: DNA
<213> ORGANISM: Artificial Sequence
<220> FEATURE:
<221> NAME/KEY: modified_base
<222> LOCATION: (10)
<223> OTHER INFORMATION: i
<220> FEATURE:
<221> NAME/KEY: modified_base
<222> LOCATION: (19)
<223> OTHER INFORMATION: i
<220> FEATURE:
<223> OTHER INFORMATION: Description of Artificial Sequence: synthetic
      DNA

<400> SEQUENCE: 18
rtcrctrtcn gtyttcatna crta                                           24

<210> SEQ ID NO 19

```
<211> LENGTH: 24
<212> TYPE: DNA
<213> ORGANISM: Artificial Sequence
<220> FEATURE:
<221> NAME/KEY: modified_base
<222> LOCATION: (4)
<223> OTHER INFORMATION: i
<220> FEATURE:
<221> NAME/KEY: modified_base
<222> LOCATION: (7)
<223> OTHER INFORMATION: i
<220> FEATURE:
<221> NAME/KEY: modified_base
<222> LOCATION: (10)
<223> OTHER INFORMATION: i
<220> FEATURE:
<221> NAME/KEY: modified_base
<222> LOCATION: (16)
<223> OTHER INFORMATION: i
<220> FEATURE:
<223> OTHER INFORMATION: Description of Artificial Sequence: synthetic
      DNA

<400> SEQUENCE: 19
rcanarnccn acrtanacrt cytc                                          24

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 20
accaccagca gtgcagcgga aac                                           23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 21
gccacgatcc tcctgaagag gca                                           23

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 22
ctaagcttga aaggatttag actgtacatg c                                  31

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 23
ctaagcttgt ctgcctgcag tctgtatctg g                                  31
```

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 24
ctaagcttga caggccatgc aagctggag                                         29

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 25
ctaagcttgt gaattcctct ttctctgctg                                        30

<210> SEQ ID NO 26
<211> LENGTH: 7
<212> TYPE: PRT
<213> ORGANISM: Homo sapiens

<400> SEQUENCE: 26

Ala Ile Arg Glu Thr Trp Gly
  1               5

<210> SEQ ID NO 27
<211> LENGTH: 8
<212> TYPE: PRT
<213> ORGANISM: Homo sapiens

<400> SEQUENCE: 27

Tyr Val Met Lys Thr Asp Ser Asp
  1               5

<210> SEQ ID NO 28
<211> LENGTH: 8
<212> TYPE: PRT
<213> ORGANISM: Homo sapiens

<400> SEQUENCE: 28

Glu Asp Val Tyr Val Gly Leu Cys
  1               5

<210> SEQ ID NO 29
<211> LENGTH: 7
<212> TYPE: PRT
<213> ORGANISM: Homo sapiens

<400> SEQUENCE: 29

Ala Ile Arg Gln Thr Trp Gly
  1               5

<210> SEQ ID NO 30
<211> LENGTH: 8
<212> TYPE: PRT
<213> ORGANISM: Homo sapiens

<400> SEQUENCE: 30

Tyr Val Met Lys Thr Asp Ser Asp

```
<210> SEQ ID NO 31
<211> LENGTH: 8
<212> TYPE: PRT
<213> ORGANISM: Homo sapiens

<400> SEQUENCE: 31

Glu Asp Val Tyr Val Gly Ile Cys
 1               5

<210> SEQ ID NO 32
<211> LENGTH: 7
<212> TYPE: PRT
<213> ORGANISM: Homo sapiens

<400> SEQUENCE: 32

Ala Ile Arg Val Thr Trp Gly
 1               5

<210> SEQ ID NO 33
<211> LENGTH: 8
<212> TYPE: PRT
<213> ORGANISM: Homo sapiens

<400> SEQUENCE: 33

Tyr Val Met Lys Thr Asp Thr Asp
 1               5

<210> SEQ ID NO 34
<211> LENGTH: 8
<212> TYPE: PRT
<213> ORGANISM: Homo sapiens

<400> SEQUENCE: 34

Glu Asp Val Tyr Val Gly Ile Cys
 1               5

<210> SEQ ID NO 35
<211> LENGTH: 7
<212> TYPE: PRT
<213> ORGANISM: Homo sapiens

<400> SEQUENCE: 35

Ala Ile Arg Ala Ser Trp Gly
 1               5

<210> SEQ ID NO 36
<211> LENGTH: 8
<212> TYPE: PRT
<213> ORGANISM: Homo sapiens

<400> SEQUENCE: 36

Tyr Val Leu Lys Thr Asp Asp Asp
 1               5

<210> SEQ ID NO 37
<211> LENGTH: 8
<212> TYPE: PRT
<213> ORGANISM: Homo sapiens

<400> SEQUENCE: 37

Glu Asp Phe Tyr Val Gly Val Ser
 1               5
```

-continued

```
<210> SEQ ID NO 38
<211> LENGTH: 16
<212> TYPE: DNA
<213> ORGANISM: Homo sapiens

<400> SEQUENCE: 38
ctgtcacggt atttcc                                                    16

<210> SEQ ID NO 39
<211> LENGTH: 16
<212> TYPE: DNA
<213> ORGANISM: Homo sapiens

<400> SEQUENCE: 39
ccaagcaggt ttctgg                                                    16

<210> SEQ ID NO 40
<211> LENGTH: 16
<212> TYPE: DNA
<213> ORGANISM: Homo sapiens

<400> SEQUENCE: 40
ctctctagag aaccct                                                    16

<210> SEQ ID NO 41
<211> LENGTH: 16
<212> TYPE: DNA
<213> ORGANISM: Homo sapiens

<400> SEQUENCE: 41
gtttggaggt agggct                                                    16

<210> SEQ ID NO 42
<211> LENGTH: 16
<212> TYPE: DNA
<213> ORGANISM: Homo sapiens

<400> SEQUENCE: 42
tttcctagtg attcct                                                    16

<210> SEQ ID NO 43
<211> LENGTH: 16
<212> TYPE: DNA
<213> ORGANISM: Homo sapiens

<400> SEQUENCE: 43
agcaaaaagt gagtta                                                    16

<210> SEQ ID NO 44
<211> LENGTH: 16
<212> TYPE: DNA
<213> ORGANISM: Homo sapiens

<400> SEQUENCE: 44
cctttcagat ggcttt                                                    16
```

POLYPEPTIDE

TECHNICAL FIELD

The present invention relates to a novel polypeptide having β1,3-galactosyltransferase activity involved in the synthesis of type 1 sugar chains such as sialyl-Lewis a sugar chain in cancer cells in the digestive system such as colon cancer cells, pancreatic cancer cells, etc. expressing sialyl-Lewis a sugar chain, a process for producing said polypeptide, a DNA coding for said polypeptide, a recombinant vector having said DNA integrated therein, a transformant carrying said recombinant vector, an antibody recognizing said polypeptide, a process for producing type 1 sugar chain-containing sugar chains and complex carbohydrates containing said sugar chains by use of said polypeptide, and a process for producing type 1 sugar chain-containing sugar chains and complex carbohydrates containing said sugar chains by use of a transformant carrying said recombinant vector.

BACKGROUND ART

It is estimated that sugar chains are involved not only in life phenomena such as development, differentiation and cell recognition but also in occurrence and progress of inflammations, cancers, infections, auto-immune diseases and a number of other diseases [A. Kobata, S. Hakomori and K. Nagai: Glycobiology Series (1) to (6), Kodansha (1993), Glycobiology, 3, 97 (1993)].

Sugar chains exist not only as glycoproteins, proteoglycans or glycolipids, in which they are added to proteins or lipids, but also as oligosaccharides.

Sugar chains having Galβ1-3GlcNAc structure are called type 1 sugar chains, and constitute core sugar chains of Lewis blood type antigens and cancer-related sugar chain antigens. The Lewis blood type antigens include not only Lewis a sugar chain [Galβ1-3(Fucα1-4)GlcNAc] but also Lewis b sugar chain [Fucα1-2Galβ1-3(Fucα1-4)GlcNAc]. Sialyl-Lewis a sugar chain [NeuAcα2-3Galβ1-3(Fucα1-4)GlcNAc] and sialyl-Lewis c sugar chain (NeuAcα2-3Galβ1-3GlcNAc) are cancer-related sugar chains detected highly frequently in cancers in mainly the digestive system such as colon cancers, pancreatic cancers, etc., and antibodies against sialyl-Lewis a sugar chain and sialyl-Lewis c sugar chain are utilized for serodiagnosis of cancers.

It is revealed that adhesion of adhesion molecule selectins (E-, P- and L-selectins) and their sugar chain ligands (sialyl-Lewis x sugar chains or their related sugar chains) is involved in accumulation of leukocytes in inflammatory sites and homing of lymphocytes to lymph nodes.

Because sialyl-Lewis a sugar chain, i.e. structural isomer of sialyl-Lewis x sugar chain [NeuAcα2-3Galβ1-4(Fucα1-3)GlcNAc] binds to selectins, sialyl-Lewis a sugar chain is considered to participate in cancer metastasis. Further, it is reported that the expression level of sialyl-Lewis a sugar chain in colon cancers and pancreatic cancers is correlated with poor prognosis of cancers.

The Galβ1-3GlcNAc structure is synthesized by a GlcNAc β1,3-galactosyltransferase. To date, genes of three GlcNAc β1,3-galactosyltransferases (β3Gal-T1, β3Gal-T2, β3Gal-T3) have been cloned, and the acceptor substrate specificity of each enzyme has been analyzed [Japanese Published Unexamined Patent Application No. 181759/94, J. Biol. Chem., 273, 58–65 (1998), J. Biol. Chem., 273, 433–440 (1998), J. Biol. Chem., 273, 12770–12778 (1998)]. Further, another β1,3-galactosyltransferase (β3Gal-T4) having different substrate specificity has been cloned [J. Biol. Chem., 272, 24794–24799 (1997), J. Biol. Chem., 273, 12770–12778 (1998)]. β3Gal-T4 synthesizes ganglioside GA1, GM1 or GD1b, but not the Galβ1-3GlcNAc structure.

If GlcNAc β1,3-galactosyltransferase involved in the synthesis of sialyl-Lewis a sugar chain and sialyl-Lewis c sugar chain as cancer-related sugar chains can be identified in cancers in the digestive system such as colon cancers, pancreatic cancers, etc., more accurate diagnosis of cancers would be feasible by examining said enzyme or the expression level of a gene of said enzyme. Further, it is expectable that cancer metastasis could be inhibited by regulating the activity of said enzyme or the transcription and translation of said enzyme gene. However, neither said enzyme nor said enzyme gene has been identified. A GlcNAc 1,3-galactosyltransferase has been partially purified from colon cancer cell line Colo205, but nobody has achieved isolation of said enzyme, determination of the amino acid sequence of said enzyme, or isolation of a gene of said enzyme [J. Biol. Chem., 262, 15649–15658 (1987), Archi. Biochem. Biophys. 270, 630–646 (1989), Archi. Biochem. Biophys. 274, 14–25 (1989)].

A sugar chain having an ability to bind to selectins is useful as a selectin antagonist to treat and prevent inflammations and cancer metastasis. Accordingly, it is estimated that β1,3-galactosyltransferases involved in the synthesis of sialyl-Lewis a sugar chains in cancers in digestive system such as colon cancers and pancreatic cancers is also applicable to efficient synthesis of selectin antagonists.

It is known that various oligosaccharides occur in human milk [Acta Paediatrica, 82, 903 (1993)]. Lacto-N-tetraose (Galβ1-3GlcNAcβ1-3GlcNAcβ1-4Glc) is contained in human milk and estimated to prevent infants from being infected with viruses or microorganisms. Further, lacto-N-tetraose has the activity of promoting the growth of *bifidobacterium* as benign enteric bacterium. On the other hand, there are few types of oligosaccharides occurring in milk from animals such as cattle, mice, etc., and a majority thereof are lactose, and trisaccharides or higher oligosaccharides scarcely occur [Acta Paediatrica, 82, 903 (1993), J. Biol. Chem., 270, 29515 (1995)].

It would be considered significantly advantageous in industry if we could produce efficiently various oligosaccharides having lacto-N-tetraose as a backbone. It is therefore an industrially important task to develop an enzyme having a higher activity of synthesizing lacto-N-tetraose than the activity of GlcNAc β1,3-galactosyltransferase so far cloned.

DISCLOSURE OF INVENTION

The object of the present invention is to provide a pharmaceutical preparation for anti-inflammations, anti-infections or inhibition of cancer metastasis, foods such as dairy products, a method of improving proteins, and a method for diagnosis of diseases such as cancers, by utilizing a novel polypeptide having β1,3-galactosyltransferase activity.

The present invention relates to:

1. A polypeptide having β1,3-galactosyltransferase activity involved in the synthesis of sialyl-Lewis a sugar chain, present in colon cancer cells expressing sialyl-Lewis a sugar chain.

The novel polypeptide of the present invention having β1,3-galactosyltransferase activity occurs not only in colon cancer cells expressing sialyl-Lewis a sugar chain, but also in cancer cells in the digestive system, such as colon cancer cells, pancreatic cancer cells, etc. expressing type 1 sugar chains such as sialyl-Lewis c sugar chain, Lewis a sugar chain, Lewis b sugar chain, etc. A polypeptide having β1,3-galactosyltransferase activity involved in efficient synthesis of type 1 sugar chains present in these cancer cells in the digestive system is also the polypeptide of the present invention. The polypeptide of the present invention is a novel β1,3-galactosyltransferase different from known β3Gal-T1, β3Gal-T2 and β3Gal-T3.

2. A polypeptide selected from the group consisting of:
   (a) a polypeptide consisting of the amino acid sequence represented by SEQ ID NO:1,
   (b) a polypeptide containing the amino acid sequence of 31 to 310 in the amino acid sequence represented by SEQ ID NO: 1, and
   (c) a polypeptide consisting of an amino acid sequence where in the amino acid sequence of the polypeptide (a) or (b), one or more amino acids have been deleted, replaced or added and having β1,3-galactosyltransferase activity capable of synthesizing Galβ1-3GlcNAc structure.

The polypeptide consisting of an amino acid sequence where in the amino acid sequence of the polypeptide (a) or (b), one or more amino acids have been deleted, replaced or added and having the β1,3-galactosyltransferase activity of the polypeptide (a) or (b) capable of synthesizing Galβ1-3GlcNAc structure can be obtained by, e.g., site-directed mutagenesis of DNA coding for a polypeptide having, e.g., the amino acid sequence represented by SEQ ID NO: 1 by using site-directed mutagenesis methods described in Molecular Cloning, A laboratory Manual, Second Edition, Cold Spring Harbor Laboratory Press (1989) (abbreviated hereinafter to Molecular Cloning, 2nd edition), Current Protocols in Molecular Biology, John Wiley & Sons (1987–1997) (abbreviated hereinafter to Current Protocols in Molecular Biology), Nucleic Acids Research, 10, 6487 (1982), Proc. Natl. Acad. Sci., USA, 79, 6409 (1982), Gene, 34, 315 (1985), Nucleic Acids Research, 13, 4431 (1985), Proc. Natl. Acad. Sci., USA, 82, 488 (1985), etc.

The number of amino acids deleted, replaced or added, which is the number of amino acids capable of being deleted, replaced or added by known methods such as site-directed mutagenesis, etc. described above, is not particularly limited, but it is preferably 1 to several decades, preferably 1 to 20, more preferably 1 to 10 and most preferably 1 to 5.

To achieve the β1,3-galactosyltransferase activity capable of synthesizing Galβ1-3GlcNAc structure, the homology of the polypeptide of the present invention with the amino acid sequence represented by SEQ ID NO: 1, as calculated using BLAST [J. Mol. Biol., 215, 403 (1990)] or FASTA [Methods in Enzymology, 183, 63–98 (1990)] (calculation means, method, etc. are described for defining of the % homology), is 60% or more, preferably 80% or more, and more preferably 95% or more.

The polypeptide consisting of an amino acid sequence where in the amino acid sequence of the polypeptide (a) or (b), one or more amino acids have been deleted, replaced or added and having β1,3-galactosyltransferase activity capable of synthesizing Galβ1-3GlcNAc structure is a novel β1,3-galactosyltransferase different from known β3Gal-T1, β3Gal-T2 and β3Gal-T3.

3. A polypeptide according to item 1 or 2 wherein the β1,3-galactosyltransferase activity is the activity of transferring galactose via β1,3-linkage to N-acetylglucosamine residue present at the non-reducing terminus of a sugar chain.

4. A polypeptide according to item 1 or 2 wherein the β1,3-galactosyltransferase activity is the activity of transferring galactose via β1,3-linkage to N-acetylglucosamine residue present at the non-reducing terminus of GlcNAcβ1-3Galβ1-4Glc or to N-acetylglucosamine monosaccharide.

5. A DNA selected from the group consisting of:
   (a) DNA coding for the polypeptide described in any one of items 1 to 4,
   (b) DNA having the nucleotide sequence of 402 to 1331 in the nucleotide sequence represented by SEQ ID NO: 2,
   (c) DNA having the nucleotide sequence of 492 to 1331 in the nucleotide sequence represented by SEQ ID NO: 2, and
   (d) DNA hybridizing under stringent conditions with the DNA described in any of (a) to (c) and coding for a polypeptide having β1,3-galactosyltransferase activity capable of synthesizing Galβ1-3GlcNAc structure.

The "DNA capable of hybridizing under stringent conditions" described above refers to a DNA obtained by colony hybridization, plaque hybridization, Southern blot hybridization, or the like, with a DNA selected as the probe from the group consisting of DNAs in items (a), (b) and (c) described above. A specific example includes a DNA which can be identified by carrying out hybridization at 65° C. in the presence of 0.7 to 1.0 mol/l NaCl using a filter on which a DNA prepared from colonies or plaques is immobilized and then washing the filter at 65° C. with a 0.1 to 2-fold conc. SSC (saline-sodium citrate) solution (1-fold conc. SSC solution is composed of 150 mmol/l sodium chloride and 15 mmol/l sodium citrate).

Hybridization can be effected according to a method described in books on experiments such as Molecular Cloning, Second Edition; and Current Protocols in Molecular Biology, Supplements 1 to 38; DNA cloning 1: Core Techniques, A Practical Approach, Second Edition, Oxford University Press (1995).

Specifically, the DNA capable of hybridizing, when calculated using BLAST [J. Mol. Biol., 215, 403 (1990)] or FASTA [Methods in Enzymology, 13, 63–98 (1990)], includes DNA having 60% or more homology, preferably 80% or more homology, more preferably 95% or more homology with a nucleotide sequence coding for a polypeptide having the amino acid sequence represented by SEQ ID NO: 1. The polypeptide encoded by said DNA and having β11,3-galactosyltransferase activity capable of synthesizing the Galβ1-3GlcNAc structure is a novel β1,3-galactosyltransferase different from known β3Gal-T1, β3Gal-T2 and β3Gal-T3.

6. A recombinant DNA prepared by integrating the DNA described in item 5 into a vector.

7. A recombinant DNA according to item 6 which is plasmid pAMo-3GT5 or plasmid pBS-3GT5 (FERM BP-6645).

8. A transformant harboring the DNA described in item 5, the recombinant DNA in item 6 or the recombinant DNA in item 7.

9. A transformant according to item 8 which is a member selected from the group consisting of a microorganism, an animal cell, a plant cell, an insect cell, a non-human transgenic animal and a transgenic plant.

10. A transformant according to item 9 wherein the microorganism is a microorganism belonging to the genus *Escherichia*.

11. A transformant according to item 9 wherein the animal cell is a member selected from the group consisting of a mouse myeloma cell, a rat myeloma cell, a mouse hybridoma cell, a CHO cell, a BHK cell, an African green monkey kidney cell, a Namalwa cell, a Namalwa KJM-1 cell, a human embryonic kidney cell and a human leukemia cell.

12. A transformant according to item 9 wherein the insect cell is a member selected from the group consisting of a *Spodoptera frugiperda* ovarian cell, a *Trichoplusia ni* ovarian cell and a silkworm ovarian cell.

13. A process for producing the polypeptide described in any one of items 1 to 4, which comprises culturing a transformant harboring a recombinant DNA prepared by integrating DNA coding for the polypeptide of any one of items 1 to 4 into a vector in a medium to thereby form and accumulate said polypeptide in the culture, and collecting said polypeptide from said culture.

14. A process for producing the polypeptide described in any one of items 1 to 4, which comprises breeding a non-human transgenic animal harboring a recombinant DNA prepared by integrating DNA coding for the polypeptide of any one of items 1 to 4 into a vector to thereby form and accumulate said polypeptide in said animal, and collecting said polypeptide from said animal.

15. A process according to item 14 wherein formation and accumulation occur in animal milk.

16. A process for producing the polypeptide described in any one of items 1 to 4, which comprises culturing a transgenic plant harboring a recombinant DNA prepared by integrating DNA coding for the polypeptide of any one of items 1 to 4 into a vector to thereby form and accumulate said polypeptide in said plant, and collecting said polypeptide from said plant.

17. A process for producing the polypeptide described in any one of items 1 to 4, which comprises synthesizing the polypeptide of any one of items 1 to 4 in an in vitro transcription and translation system using DNA coding for said polypeptide.

18. A process for producing a reaction product having galactose, which comprises using the polypeptide of any one of items 1 to 4 as an enzyme source, and allowing
 (a) said enzyme source,
 (b) an acceptor substrate selected from the group consisting of:
  i) N-acetylglucosamine (GlcNAc),
  ii) an oligosaccharide having N-acetylglucosamine residue at the non-reducing terminus thereof, and
  iii) a complex carbohydrate having N-acetylglucosamine residue at the non-reducing terminus thereof, and
 (c) uridine-5'-diphosphate galactose to be present in an aqueous medium to thereby form and accumulate said reaction product in the aqueous medium, and collecting said reaction product from said aqueous medium, wherein the galactose is transferred via β1,3-linkage to N-acetylglucosamine or N-acetylglucosamine residue of said acceptor substrate.

19. A process for producing a reaction product having galactose, which comprises using the polypeptide of any of items 1 to 4 as an enzyme source, and allowing
 (a) said enzyme source,
 (b) an acceptor substrate selected from the group consisting of:
  i) glucose,
  ii) an oligosaccharide having glucose residue at the non-reducing terminus thereof, and
  iii) a complex carbohydrate having glucose residue at the non-reducing terminus thereof, and
 (c) uridine-5'-diphosphate galactose to be present in an aqueous medium to thereby form and accumulate said reaction product in the aqueous medium, and collecting said reaction product from said aqueous medium, wherein the galactose is transferred via β1,3-linkage to glucose or glucose residue of said acceptor substrate.

20. A process for producing a sugar chain or a complex carbohydrate, which comprises culturing the transformant selected from the group consisting of transformants of item 9 derived from a microorganism, an animal cell, a plant cell and an insect cell in a medium to thereby form and accumulate a sugar chain having galactose transferred via 11,3-linkage to N-acetylglucosamine, N-acetylglucosamine residue, glucose or glucose residue thereof or a complex carbohydrate containing said sugar chain in the culture, and collecting said sugar chain or said complex carbohydrate from said culture.

21. A process for producing a sugar chain or a complex carbohydrate, which comprises breeding the non-human transgenic animal of item 9 to thereby form and accumulate in said animal a sugar chain having galactose transferred via β1,3-linkage to N-acetylglucosamine, N-acetylglucosamine residue, glucose or glucose residue thereof or a complex carbohydrate containing said sugar chain, and collecting said sugar chain or said complex carbohydrate from said animal.

22. A process for producing a sugar chain or a complex carbohydrate, which comprises culturing the transgenic plant of item 9 to thereby form and accumulate in said plant a sugar chain having galactose transferred via β1,3-linkage to N-acetylglucosamine, N-acetylglucosamine residue, glucose or glucose residue thereof or a complex carbohydrate containing said sugar chain, and collecting said sugar chain or said complex carbohydrate from said plant.

23. A process according to any of items 18 to 22 wherein the complex carbohydrate is a complex carbohydrate selected from the group consisting of a glycoprotein, a glycolipid, a proteoglycan, a glycopeptide, a lipopolysaccharide, a peptidoglycan and a glycoside which is a steroid compound with a sugar chain.

24. A process according to item 21 wherein formation and accumulation occur in animal milk.

25. A method for determining the expression level of a gene encoding the polypeptide of any one of items 1 to 4, which comprises hybridization using DNA coding for said polypeptide or a fragment of said DNA.

26. A DNA selected from the group consisting of an oligonucleotide having the same nucleotide sequence as a consecutive 5- to 60-nucleotide sequence in the nucleotide sequence of the DNA of item 5 or of a DNA having the nucleotide sequence represented by SEQ ID NO: 2 or 3, an oligonucleotide having a sequence complementary to said oligonucleotide, and an oligonucleotide derivative of any of said oligonucleotides.

27. A DNA according to item 26 wherein the oligonucleotide derivative is selected from the group consisting of an oligonucleotide derivative in which the phosphodiester bond is converted into a phosphorothioate bond, an oligonucleotide derivative in which the phosphodiester bond is converted into an N3'-P5'-phosphoamidate bond, an oligonucleotide derivative in which the ribose and the phosphodiester bond are converted into a peptide-nucleic acid bond, an oligonucleotide derivative in which the uracil is replaced by a C-5 propynyluracil, an oligonicleotide derivative in which the uracil is replaced by a C-5 thiazolyluracil, an oligonucleotide derivative in which the cytosine is replaced by a C-5 propynylcytosine, an oligonucleotide derivative in which the cytosine is replaced by a phenoxazine-modified cytosine, an oligonucleotide derivative in which the ribose is replaced by a 2'-O-propylribose, and an oligonucleotide derivative in which the ribose is replaced by a 2'-methoxyethoxyribose.

28. A DNA that has a nucleotide sequence represented by SEQ ID NO: 20 or 21.

29. A method for determining the expression level of a gene encoding the polypeptide of any one of items 1 to 4, which comprises polymerase chain reaction using the DNA of any one of items 26 to 28.

30. A method for detecting cancers and cancer metastasis, which comprises using the method of item 25 or 29.

31. A method for inhibiting transcription of DNA coding for the polypeptide of any one of items 1 to 4 or translation of its corresponding mRNA, which comprises using a DNA selected from DNAs of items 5 and 26 to 28 and DNAs having a nucleotide sequence represented by SEQ ID NO: 2 or 3.

32. An antibody recognizing the polypeptide of any one of items 1 to 4.

33. A method for immunological detection of the polypeptide of any one of items 1 to 4, which comprises using the antibody of item 32.

34. An immunohistostaining method, which comprises detecting the polypeptide of any one of items 1 to 4 by using the antibody of item 32.

35. An immunohistostaining agent comprising the antibody of item 32.

36. A diagnostic reagent for cancers or cancer metastasis, which comprises the antibody of item 32.

37. A method for screening a compound varying the activity of the polypeptide of any one of items 1 to 4, which comprises contacting said polypeptide with a test sample.

38. A method for screening a compound varying the expression of a gene coding for the polypeptide of any one of items 1 to 4, which comprises contacting cells expressing said polypeptide with a test sample and determining the content of sialyl-Lewis a sugar chain, Lewis a sugar chain, Lewis b sugar chain or sialyl-Lewis c sugar chain by use of anti-sialyl-Lewis a antibody, anti-Lewis a antibody, anti-Lewis b antibody or anti-sialyl-Lewis c antibody.

39. A method for screening a compound varying the expression of a gene coding for the polypeptide of any one of items 1 to 4, which comprises contacting cells expressing said polypeptide with a test sample and determining the content of said polypeptide by use of the antibody of item 32.

40. A promoter DNA governing transcription of a gene coding for the polypeptide described in any one of items 1 to 4.

41. A promoter DNA according to item 40, which works in cells selected from the group consisting of small intestine cells, large intestine cells, pancreas cells, stomach cells, colon cancer cells, pancreatic cancer cells and stomach cancer cells.

42. A promoter DNA according to item 40 or 41, which is a human- or mouse-derived promoter DNA.

43. A promoter DNA according to any one of items 40 to 42, which comprises a 50- to 5000-bp consecutive nucleotide DNA sequence in the nucleotide sequence of 1 to 5000 in the nucleotide sequence represented by SEQ ID NO: 3.

44. A method for screening a compound varying the efficiency of transcription by the promoter DNA of any one of items 40 to 43, which comprises transforming animal cells with a plasmid containing said promoter DNA and a reporter gene ligated downstream of said promoter DNA, then contacting the transformant with a test sample, and determining the content of a translation product of said reporter gene.

45. A screening method according to item 44 wherein the reporter gene is a gene selected from the group consisting of a chloramphenicol acetyltransferase gene, a β-glucuronidase gene, a β-galactosidase gene, a β-lactamase gene, a luciferase gene, an aequorin gene and a green fluorescent protein gene.

46. A knockout non-human animal wherein a DNA coding for the polypeptide of any one of items 1 to 4 is rendered defective or mutated.

47. A knockout non-human animal according to item 46 wherein the knockout non-human animal is a mouse.

Hereinafter, the present invention is described in detail.

(1) Acquisition of DNA Coding for the Novel Polypeptide of the Present Invention having β1,3-Galactosyltransferase Activity Capable of Synthesizing Type 1 Sugar Chains Such as Sialyl-Lewis a Sugar Chain (Hereinafter Also Called Novel β1,3-Galactosyltransferase Gene) and Production of said DNA and Oligonucleotides A cDNA library is prepared in a usual manner from sialyl-Lewis a sugar chain- or sialyl-Lewis c sugar chain-expressing cancer cells in the digestive system, such as colon cancer cells or pancreatic cancer cells.

The method of preparing the cDNA library includes methods described in Molecular Cloning, 2nd edition, Current Protocols in Molecular Biology, Supplements 1-38, A Laboratory Manual, 2nd Ed. (1989), DNA Cloning 1: Core Techniques, A Practical Approach, Second Edition, Oxford University Press (1995) or methods using commercially available kits such as SuperScript Plasmid System for cDNA Synthesis and Plasmid Cloning (a product of Gibco BRL) and ZAP-cDNA Synthesis Kit (a product of Stratagene).

Examples of the sialyl-Lewis a sugar chain- or sialyl-Lewis c sugar chain-expressing cancer cells in the digestive system, such as colon cancer cells or pancreatic cancer cells useful in the present invention include human colon cancer cell lines Colo205, Colo201 and SW1116 expressing sialyl-Lewis a sugar chains and human pancreatic cancer cell line Capan-2 expressing sialyl Lewis a sugar chains. The cloning vector for preparing the cDNA library may be any phage vectors, plasmid vectors, etc. insofar as they can be autonomously replicated in *E. coli* K12.

Specific examples include ZAP Express [Strategies, 5, 58 (1992), a product of Stratagene], pBluescript II SK(+) [Nucleic Acids Research, 17, 9494 (1989)], λZAP II (a product of Stratagene), λgt10, λgt11 [DNA Cloning, A Practical Approach, 1, 49 (1985)], λTriplEx (a product of Clonetech), λExCell (a product of Pharmacia), pT7T318U (a product of Pharmacia), pcD2 [Mol. Cell. Biol., 3, 280 (1983)], pUC18 [Gene, 33, 103 (1985)] and pAMo [J. Biol. Chem., 268, 22782–22787 (1993), also called pAMoPRC3Sc (Japanese Published Unexamined Patent Application No. 336963/93)].

The host microorganisms may be any microorganisms belonging to *Escherichia coli*. Specifically, *Escherichia coli* XL1-Blue MRF' [Strategies, 5, 81 (1992), a product of Stratagene], *Escherichia coli* C600 [Genetics, 39, 440 (1954)], *Escherichia coli* Y1088 [Science, 222, 778 (1983)], *Escherichia coli* Y1090 [Science, 222, 778 (1983)], *Escherichia coli* NM522 [J. Mol. Biol., 166, 1 (1983)], *Escherichia coli* K802 [J. Mol. Biol., 16, 118 (1966)], *Escherichia coli* JM105 [Gene, 38, 275 (1985)], *Escherichia coli* SOLR™ Strain [commercially available from Stratagene], *E. coli* LE392 (Molecular Cloning, 2nd ed.), etc. can be used.

The cDNA library includes a cDNA library prepared, e.g., in the following manner.

A cDNA is synthesized with a cDNA synthesis system (a product of GIBCO BRL) using mRNA derived from human colon cancer cell line Colo205.

A plasmid is prepared by adding an SfiI linker to both termini of the DNA and then inserting the resulting DNA into SfiI sites of cloning vector pAMo.

The plasmid is used to transform *E. coli* LE392 to prepare a cDNA library.

From the prepared cDNA library, a clone containing the objective DNA is selected in the following manner.

From the cDNA library prepared above, plasmids are prepared in a usual manner or by using a plasmid maxi kit (Product No. 41031), that is, a plasmid preparation kit produced by Qiagen.

By comparing the amino acid sequences of four known P1,3-galactosyltransferases, two or more well-conserved regions among the four β1,3-galactosyltransferases are found.

Degenerate primers each having a DNA sequence corresponding to the amino acid sequence of each region are designed according to known methods [Carl W. Dieffenbach, Gabriela S. Dveksler, "PCR Primer: A Laboratory Manual", Cold Spring Harbor Lab. (1995), The Protocol Series "cDNA Cloning" ed. Jyunichiro Inoue & Kentaro Senba, Yodosha (1996), Science, 241, 42 (1988)], and polymerase chain reaction (hereinafter abbreviated to PCR) [Molecular Cloning, 2nd edition and PCR Protocols Academic Press (1990)] is conducted using the cDNA library prepared above as a template, and the amplified fragment is subcloned into a suitable plasmid.

Subcloning of the PCR-amplified fragment can be performed in a usual manner by integrating the amplified fragment, as such or after treatment with restriction enzymes or DNA polymerase into a vector.

The vector includes pBluescript II SK(+) and pBluescript SK(−) (both available from Stratagene), pDIRECT [Nucleic Acids Research, 18, 6069 (1990)], pCR-Script Amp SK(+) [a product of Stratagene, Strategies, 5, 6264 (1992)], pT7Blue [a product of Novagen], pCR II [a product of Invitrogen, Biotechnology, 9, 657 (1991)], pCR-TRAP [a product of Genehunter], pNoTA$_{T7}$ (a product of 5'→3' Ltd.), etc.

By determining the nucleotide sequence of the subcloned PCR-amplified fragment, a DNA fragment coding for an amino acid sequence that is homologous to, but not completely consistent with, the amino acid sequence of known β1,3-galactosyltransferase is selected. The nucleotide sequence of the DNA can be determined by conventional nucleotide sequence analysis using the dideoxy method of Sanger, et al. [Proc. Natl. Acad. Sci. USA, 74, 5463 (1977)] or a nucleotide sequencer such as 373A•DNA sequencer (a product of Perkin Elmer).

By subjecting the cDNA library prepared above to colony hybridization or plaque hybridization (Molecular Cloning, 2nd ed.) with said DNA fragment as the probe, cDNA coding for a polypeptide having homology to known β1,3-galactosyltransferases can be obtained. As the probe, said DNA fragment labeled with an isotope or digoxigenin can be used.

The DNA obtained in the method described above, as such or after cleavage with appropriate restriction enzymes, is inserted into a vector by a conventional method, and then the nucleotide sequence of the DNA can be determined by conventional nucleotide sequence analysis using the dideoxy method of Sanger, et al. [Proc. Natl. Acad. Sci. USA, 74, 5463 (1977)] or a nucleotide sequencer such as 373A•DNA sequencer (a product of Perkin Elmer).

The DNA obtained by said method includes, e.g., DNA coding for the polypeptide represented by SEQ ID NO: 1, and specifically, DNA having the nucleotide sequence represented by SEQ ID NO: 2 or 3 can be mentioned.

The plasmid containing the DNA represented by SEQ ID NO: 2 includes, e.g., pAMo-3GT5 and pBS-3GT5 (FERM BP-6645) described in the Examples below.

The DNA obtained in the manner described above is integrated into an expression vector to construct an expression plasmid. After the resulting expression plasmid is introduced into suitable animal cells, whether said DNA codes for β1,3-galactosyltransferase participating in the synthesis of sialyl-Lewis a sugar chain or sialyl-Lewis c sugar chain can be examined by analysis with a fluorescence activated cell sorter (hereinafter abbreviated to FACS) using anti-sialyl-Lewis a sugar chain antibody or anti-sialyl-Lewis c sugar chain antibody.

As said expression vector, an vector capable of integrating said cDNA therein and expressing it in animal cells can be used, and for example, pcDNAI/Amp, pcDNAI, pCDM8 (which all are available from Funakoshi K. K.), pAGE107 [Japanese Published Unexamined Patent Application No. 22979/91, Cytotechnology, 3, 133 (1990)], pREP4 (a product of Invitrogen), pAGE103 [J. Biochem., 101, 1307 (1987)], pAMo, pAMoA [J. Biol. Chem., 268, 22782–22787 (1993), also called pAMoPRSA (Japanese Published Unexamined Patent Applicaiton No. 336963/93], pAS3-3 (Japanese Published Unexamined Patent Application No. 227075/90), etc. can be mentioned.

The expression vector into which the cDNA has been integrated is introduced into animal cells capable of expressing the objective cDNA, to give transformed cells.

The method of introducing said expression vector may be any method of introducing DNA into animal cells, and mention can be made of, e.g., the electroporation method [Cytotechnology, 3, 133 (1990)], the calcium phosphate method (Japanese Published Unexamined Patent Application No. 227075/90), the lipofection method [Proc. Natl. Acad. Sci. USA, 84, 7413 (1987)] and the method described in Virology, 52, 456 (1973).

The animal cells include Namalwa cells that are human cells, Namalwa KJM-1 cells that are a sub-line of Namalwa cells, COS cells that are simian cells, CHO cells that are Chinese hamster cells, HBT5637 (Japanese Published Unexamined Patent Application No. 299/88) and HCT-15 that is a colon cancer cell line, among which Namalwa cells, Namalwa KJM-1 cells and HCT-15 are preferable.

The resulting transformed cells are cultured in a usual manner.

Specifically, mention can be made of the following method of culturing transformants.

When the transformants are animal cells, the medium for culturing the cells is a generally used medium such as RPMI1640 medium [The Journal of the American Medical Association, 199, 519 (1967)], Eagle's MEM medium [Science, 122, 501 (1952)], DMEM medium [Virology, 8, 396 (1959)], 199 medium [Proceeding of the Society for the Biological Medicine, 73, 1 (1950)] or any of these media further supplemented with fetal calf serum.

The culturing is conducted usually for 1 to 7 days at pH 6 to 8, at 25 to 40° C. in the presence of 5% $CO_2$.

If necessary, antibiotics such as kanamycin, penicillin and streptomycin may be added to the medium during the culturing.

The cells obtained in the culturing are fluorescently stained with anti-sialyl-Lewis a sugar chain antibody or anti-sialyl-Lewis c sugar chain antibody and then analyzed by FACS, to examine whether the amount of sialyl-Lewis a sugar chains or sialyl-Lewis c sugar chains in the cells transformed with said expression plasmid is increased or not. If the amount of sialyl-Lewis a sugar chains or sialyl-Lewis c sugar chains is increased, said DNA can be estimated to code for novel β1,3-galactosyltransferase involved in the synthesis of sialyl-Lewis a sugar chain or sialyl-Lewis c sugar chain.

Any antibodies reacting with sialyl-Lewis a sugar chain or sialyl-Lewis c sugar chain can be used as anti-sialyl-Lewis a sugar chain antibody or anti-sialyl-Lewis c sugar chain antibody, respectively, and examples thereof include 19-9 (a product of Fujirebio) and KM231 (a product of Kyowa Medex) as anti-sialyl-Lewis a sugar chain antibodies and DU-PAN-2 (a product of Kyowa Medex) as anti-sialyl-Lewis c sugar chain antibody.

In the manner described above, it is possible to obtain DNA coding for the novel polypeptide having β1,3-galactosyltransferase activity, participating in the synthesis of cancer-related sugar chains belonging to type 1 sugar chains such as sialyl-Lewis a sugar chain in cancer cells in the digestive system, such as colon cancer cells, pancreatic cancer cells, etc.

By selecting DNA hybridizing under stringent conditions with the DNA obtained in the method described above, it is possible to obtain the objective DNA coding for a polypeptide having an amino acid sequence where in SEQ ID NO: 1, one or more amino acids have been replaced, deleted or added.

That is, the objective DNA can be obtained by screening a cDNA library derived from non-human animals such as mouse, rat, cattle and monkey.

On the basis of the determined amino acid sequence of the novel β1,3-galactosyltransferase polypeptide, the objective DNA can also be prepared by chemically synthesizing DNA coding for said polypeptide. Chemical synthesis of the DNA can be carried out with a DNA synthesizer using the thiophosphite method (a product of Shimadzu Corporation), a DNA synthesizer model 392 using the phosphoamidite method (a product of Perkin Elmer), or the like.

Further, the objective DNA can also be prepared by PCR where oligonucleotides described below are used as sense primer and antisense primer while cDNA prepared from mRNA in cells expressing mRNA complementary to said DNA is used as a template.

The DNA and DNA fragment of the present invention obtained in the above-described methods can be used in the conventional method described in Molecular Cloning, 2nd edition or in a DNA synthesizer, to prepare oligonucleotides such as antisense oligonucleotide, sense oligonucleotide, etc. having a partial sequence of the DNA of the present invention.

Said oligonucleotides include DNA having the same sequence as a sequence of consecutive 5 to 60 nucleotides in the objective DNA, or DNA having a complementary sequence to said DNA, and specific examples include DNA having the same sequence as a consecutive 5- to 60-nucleotide sequence in the nucleotide sequence represented by SEQ ID NO: 2 or 3, or DNA having a complementary sequence to said DNA. If these are used as sense and antisense primers, two oligonucleotides described above having similar melting temperatures (Tm) and similar numbers of nucleotides are preferably used. Specifically, mention is made of oligonucleotides having the nucleotide sequences represented by SEQ ID NOS: 20, 21, etc.

Furthermore, derivatives of these oligonucleotides (also referred to hereinafter as oligonucleotide derivatives) can also be used as the oligonucleotide of the present invention.

Said oligonucleotide derivatives include an oligonucleotide derivative in which the phosphodiester bond is converted into a phosphorothioate bond, an oligonucleotide derivative in which the phosphodiester bond is converted into an N3'-P5'-phosphoamidate bond, an oligonucleotide derivative in which the ribose and the phosphodiester bond are converted into a peptide-nucleic acid bond, an oligonucleotide derivative in which the uracil is replaced by a C-5 propynyluracil, an oligonucleotide derivative in which the uracil is replaced by a C-5 thiazolyluracil, an oligonucleotide derivative in which the cytosine is replaced by a C-5 propynylcytosine, an oligonucleotide derivative in which the cytosine is replaced by a phenoxazine-modified cytosine, an oligonucleotide derivative in which the ribose is replaced by a 2'-O-propylribose, and an oligonucleotide derivative in which the ribose is replaced by a 2'-methoxyethoxyribose [Saibo Kogaku (Cell Engineering), 16, 1463 (1997)].

(2) Production of Novel β1,3-Galactosyltransferase Polypeptide (also Referred to Hereinafter as the Polypeptide of the Present Invention)

The polypeptide of the present invention can be produced by expressing the DNA of the present invention in host cells in, e.g., the following manner using the methods described in Molecular Cloning, 2nd edition or Current Protocols in Molecular Biology Supplements 1–38, etc.

On the basis of the full-length DNA coding for the polypeptide of the present invention, a DNA fragment having suitable length containing a region coding for said polypeptide is prepared, if necessary.

Further, DNA useful for improving the production efficiency of said polypeptide can be prepared by replacing a nucleotide in the nucleotide sequence of the region encoding the polypeptide so as to make a codon most suitable for the expression in a host.

Said DNA fragment or said full-length DNA is inserted into a site downstream from a promoter in a suitable expression vector to construct a recombinant DNA (recombinant vector).

By introducing said recombinant vector into host cells suitable for said expression vector, a transformant expressing the polypeptide of the present invention can be obtained.

The host cells may be prokaryotic cells, yeasts, animal cells, insect cells, plant cells insofar as they can express the objective gene. Animals or plants can also be used.

The expression vector used is a vector capable of autonomous replication or integration into the chromosome in the host cells and containing a promoter at a position suitable for transcription of the novel β1,3-galactosyltransferase gene.

When prokaryotes such as bacteria are used as the host cells, it is preferred that the expression vector for the novel β1,3-galactosyltransferase gene is capable of autonomous replication in the prokaryotes and comprises a promoter, a ribosome-binding sequence, the novel β1,3-galactosyltransferase gene, and a transcription termination sequence. The vector may further comprise a gene regulating the promoter.

The expression vector includes, e.g., pBTrp2, pBTac1, pBTac2 (which all are commercially available from Boehringer Mannheim), pKK233-2 (a product of Pharmacia), pSE280 (a product of Invitrogen), pGEMEX-1 (a product of Promega), pQE-8 (a product of QIAGEN), pKYP10 (Japanese Published Unexamined Patent Application No. 110600/83), pKYP200 [Agric. Biol. Chem., 48, 669 (1984)], pLSA1 [Agric. Biol. Chem., 53, 277 (1989)], pGEL1 [Proc. Natl.

Acad. Sci., USA, 82, 4306 (1985)], pBluescript II SK+ (a product of Stratagene), pBluescript II SK(−) (a product of Stratagene), pTrs30 (FERM BP-5407), pTrs32 (FERM BP-5408), pGHA2 (FERM BP-400), pGKA2 (FERM BP-6798), pTerm2 (Japanese Published Unexamined Patent Application No. 22979/91, U.S. Pat. Nos. 4,686,191, 4,939,094, 5,160,735), pEG400 [J. Bacteriol., 172, 2392 (1990)], pGEX (a product of Pharmacia), pET system (a product of Novagen), pSupex, pUB110, pTP5, pC194, pTrxFus (a product of Invitrogen), pMAL-c2 (a product of New England Biolabs), pUC19 [Gene, 33, 103 (1985)], pSTV28 (a product of Takara Shuzo Co., Ltd.), pUC118 (a product of Takara Shuzo Co., Ltd.) and pPA1 (Japanese Published Unexamined Patent Application No. 233798/88).

The promoter may be any one insofar as it is capable of working in host cells such as *E. coli*, etc. Examples are promoters derived from *E. coli*, phage, etc., such as trp promoter (Ptrp), lac promoter (Plac), $P_L$ promoter, $P_R$ promoter, $P_{SE}$ promoter, etc. as well as SP01 promoter, SPO2 promoter, pen P promoter, etc. Artificially designed and modified promoters such as a Ptrpx2 promoter in which two Ptrps are combined in tandem, tac promoter, lacT7 promoter, letI promoter, etc. can also be used.

A plasmid in which the distance between the Shine-Dalgarno sequence (ribosome binding sequence) and the initiation codon is adjusted to an appropriate length (e.g., 6 to 18 bases) may be preferably used.

Although a transcription termination sequence is not necessarily required to express the DNA of the present invention, it is preferable to locate the transcription termination sequence just downstream from the structural gene.

The host cells include microorganisms belonging to the genera *Escherichia, Serratia, Bacillus, Brevibacterium, Corynebacterium, Microbacterium* and *Pseudomonas*. Specific examples are *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* BL21(DE3), *Escherichia coli* BL21(DE3)pLysS, *Escherichia coli* HMS174(DE3), *Escherichia coli* HMS174 (DE3)pLysS, *Serratia ficaria, Serratia fonticola, Serratia liquefaciens, Serratia marcescens, Bacillus subtilis, Bacillus amyloliquefaciens, Brevibacterium ammoniagenes, Brevibacterium immariophilum* ATCC14068, *Brevibacterium* saccharolyticum ATCC14066, *Corynebacterium glutamicum* ATCC13032, *Corynebacterium glutamicum* ATCC14067, *Corynebacterium glutamicum* ATCC13869, *Corynebacterium acetoacidophilum* ATCC13870, *Microbacterium* ammoniaphilum ATCC15354, *Pseudomonas* sp. D-0110, etc.

The method of introducing the recombinant vector may be any method of introducing DNA into the host cells described above, and for example, mention can be made of the electroporation method [Nucleic Acids Res., 16, 6127 (1988)], the method using calcium ion [Proc. Natl. Acad. Sci. USA, 69, 2110 (1972)], the protoplast method (Japanese Published Unexamined Patent Application No. 248394/88), and the methods described in Gene, 17, 107 (1982) and Molecular & General Genetics, 168, 111 (1979).

When yeasts are used as the host cells, expression vectors such as YEp13 (ATCC37115), YEp24 (ATCC37051), YCp50 (ATCC37419), pHS19, pHS15, etc. can be exemplified.

Any promoters can be used insofar as they are capable of working in yeasts. For example, mention can be made of promoters such as PHO5 promoter, PGK promoter, GAP promoter, ADH promoter, gal 1 promoter, gal 10 promoter, heat shock protein promoter, MF α1 promoter, CUP 1 promoter, etc.

The host cells include yeast strains belonging to the genera *Saccharomyces, Schizosaccharomyces, Kluyveromyces*, Trichosporon, *Schwanniomyces* and *Pichia*. Specifically, mention can be made of Saccharomyces cerevisiae, Schizosaccharomyces pombe, Kluyveromyces lactis, Trichosporon pullulans, *Schwanniomyces* alluvius, *Pichia pastoris*, etc.

The method of introducing the recombinant vector may be any method of introducing DNA into yeast, and examples include the electroporation method [Methods Enzymol., 194, 182 (1990)], the spheroplast method [Proc. Natl. Acad. Sci. USA, 84, 1929 (1978)], the lithium acetate method [J. Bacteriol., 153, 163 (1983)] and the method described in Proc. Natl. Acad. Sci. USA, 75, 1929 (1978).

When animal cells are used as the host cells, mention can be made of, e.g., expression vectors such as pcDNAI/Amp, pcDNAI, pCDM8 (which all are available from Funakoshi), pAGE107 [Japanese Published Unexamined Patent Application No. 22979/91, Cytotechnology, 3, 133 (1990)], pREP4 (a product of Invitrogen), pAGE103 [J. Biochem., 101, 1307 (1987)], pAMo, pAMoA [J. Biol. Chem., 268, 22782–22787 (1993), also called pAMoPRSA (Japanese Published Unexamined Patent Application No. 336963/93), pAS3-3 (Japanese Published Unexamined Patent Application No. 227075/90).

The promoter used may be any promoter capable of working in animal cells. Examples are the promoter of IE (immediate early) gene of cytomegalovirus (human CMV), SV40 early promoter, the long terminal repeat promoter of moloney murine leukemia virus, the promoter of retrovirus, a heat shock promoter, SR a promoter and a metallothionein promoter. Furthermore, the enhancer of IE gene of human CMV may be used together with the promoter.

The host cells include mouse myeloma cells, rat myeloma cells, mouse hybridoma cells, CHO cells that are Chinese hamster cells, BHK cells, African green monkey kidney cells, Namalwa cells or Namalwa KJM-1 cells that are human cells, human embryonic kidney cells, human leukemia cells, HBT5637 (Japanese Published Unexamined Patent Application No. 299/88) and human colon cancer cell lines.

The mouse myeloma cells include SP2/0 and NS0; the rat myeloma cells include YB2/0; the human embryonic kidney cells include HEK293 (ATCC: CRL-1573); the human leukemia cells include BALL-1; the African green monkey kidney cells include COS-1 and COS-7; and the human colon cancer cell lines include HCT-15.

The method of introducing the recombinant vector may be any method of introducing DNA into animal cells. For example, mention can be made of the electroporation method [Cytotechnology, 3, 133 (1990)], the calcium phosphate method (Japanese Published Unexamined Patent Application No. 227075/90), the lipofection method [Proc. Natl. Acad. Sci. USA, 84, 7413 (1987)], and the method described in Virology, 52, 456 (1973).

When insect cells are used as the host, the polypeptide can be expressed by methods described in Baculovirus Expression Vectors, A Laboratory Manual, W.H. Freeman and Company, New York (1992); Molecular Biology, A Laboratory Manual; Current Protocols in Molecular Biology Supplements 1–38; Bio/Technology, 6, 47 (1988), and so on.

That is, the recombinant gene transfer vector and a baculovirus are cotransfected into insect cells so that a recombinant virus is obtained in the culture supernatant of the insect cells, and then insect cells are infected with the recombinant virus, whereby the polypeptide can be expressed.

The gene transfer vector used in this method includes, e.g., pLV1392, pVL1393 and pBlueBacIII (which all are products of Invitrogen).

As the baculovirus, it is possible to employ, e.g. *Autographa californica* nuclear polyhedrosis virus, which is a virus infecting insects of the family Barathra.

As the insect cells, it is possible to use *Spodoptera frugiperda* ovarian cells, *Trichoplusia ni* ovarian cells, cultured cells derived from silkworm ovaries, etc.

*Spodoptera frugiperda* ovarian cells include Sf9 and Sf21 (Baculovirus Expression Vectors, A Laboratory Manual); *Trichoplusia ni* ovarian cells include High 5 and BTI-TN-5B1-4 (a product of Invitrogen); and the cultured cells derived from silkworm ovaries include *Bombyx mori* N4.

As cotransfection methods of the aforesaid recombinant gene transfer vector and the aforesaid baculovirus into insect cells to prepare the recombinant virus, the calcium phosphate method (Japanese Published Unexamined Patent Application No. 227075/90), and the lipofection method [Proc. Natl. Acad. Sci. USA, 84, 7413 (1987)] can be exemplified.

The same method as for introducing DNA into animal cells can be used for introducing DNA into insect cells. For example, mention can be made of the electroporation method [Cytotechnology, 3, 133 (1990)], the calcium phosphate method (Japanese Published Unexamined Patent Application No. 227075/90), and the lipofection method [Proc. Natl. Acad. Sci. USA, 84, 7413 (1987)].

When plant cells or plants are used as the host, the polypeptide can be produced according to known methods [Soshiki Baiyo (Tissue Culture), 20 (1994); Soshiki Baiyo (Tissue Culture), 21 (1995); Trends in Biotechnology, 15, 45 (1997)].

The expression vector includes, e.g., Ti plasmid and tobacco mosaic virus vector.

Any promoter capable of working in plant cells can be used as the promoter for the gene expression, and examples include 35S promoter of cauliflower mosaic virus (CaMV), and rice actin 1 promoter. Furthermore, the efficiency of expression of the gene can also be raised by inserting, e.g. intron 1 of the maize alcohol dehydrogenase gene into a region between the promoter and the gene to be expressed.

The host cells include cells of plants such as potato, tobacco, maize, rice, rape, soybean, tomato, carrot, wheat, barley, rye, alfalfa, flax, etc.

The method of introducing the recombinant vector may be any method of introducing DNA into plant cells. For example, it is possible to use a method using *Agrobacterium* (Japanese Published Unexamined Patent Application No. 140885/84, Japanese Published Unexamined Patent Application No. 70080/85, WO94/00977), the electroporation method (Japanese Published Unexamined Patent Application No. 251887/85) or a method using a particle gun (gene gun) (Japanese Patents Nos. 2606856 and 2517813).

The plant cells or organs to which the gene is introduced can be subjected to mass culture using a jar fermentor.

The medium used in culturing includes generally employed media such as Murashige & Skoog (MS) medium and White medium, and media prepared by adding phytohormones such as auxin and cytokinin to these media.

The culturing is conducted usually at pH 5 to 9 at 20 to 40° C. for 3 to 60 days.

If necessary, antibiotics such as kanamycin and hygromycin may be added to the medium during the culturing.

Further, plant cells to which the gene is introduced can be re-differentiated to produce a plant (transgenic plant) having the introduced gene.

An animal can also be used to produce the polypeptide of the present invention. For example, the polypeptide of the present invention can be produced according to known methods [American Journal of Clinical Nutrition, 63, 639S (1996), American Journal of Clinical Nutrition, 63, 627S (1996), Bio/Technology, 9, 830 (1991)] in an animal to which the gene was introduced.

The promoter used may be any promoter capable of working in an animal. For example, mammary gland cell-specific promoters such as α-casein promoter, β-casein promoter, β-lactoglobulin promoter, and whey acidic protein promoter are preferably used.

A transformant derived from a microorganism, animal cells or plant cells harboring a recombinant vector containing DNA coding for the polypeptide of the present invention is cultured in a usual culture method until the polypeptide is formed and accumulated, and the polypeptide is collected from the culture whereby said polypeptide can be produced.

When the transformant is an animal or plant, it is raised or cultured in a usual manner until the polypeptide is formed and accumulated, and the polypeptide is recovered from the animal or plant whereby said polypeptide can be produced.

That is, in the case of an animal, for example, a non-human transgenic animal harboring the DNA of the present invention is raised until the novel polypeptide having β1,3-galactosyltransferase activity, encoded by said recombinant DNA, is formed and accumulated in the animal, and the polypeptide is collected from the animal whereby the novel polypeptide having β1, 3-galactosyltransferase activity can be produced. The place where the polypeptide is formed and accumulated in the animal is, for example, milk and egg of the animal.

In the case of the plant, for example, a transgenic plant harboring the DNA of the present invention is cultured until the novel polypeptide having β1,3-galactosyltransferase activity, encoded by said recombinant DNA, is formed and accumulated in the plant, and the polypeptide is recovered from the plant whereby the novel polypeptide having β1,3-galactosyltransferase activity can be produced.

When the transformants for producing the polypeptide of the present invention are prokaryotes such as *E. coli*, etc. or eucaryotes such as yeast, etc., the polypeptide of the present invention can be produced by culturing the transformants of the present invention in a medium to thereby form and accumulate the polypeptide of the present invention in the culture, and collecting said polypeptide from said culture.

The transformant of the present invention in the medium can be cultured according to conventional methods used for culturing the host.

The medium for culturing the transformant obtained by using prokaryotes such as *E. coli* or eucaryotes such as yeast may be natural or synthetic medium insofar as the medium contains a carbon source, a nitrogen source, inorganic salts, etc. which can be assimilated by the organisms and in which the transformants can be efficiently cultured.

Any carbon source can be used insofar as it can be assimilated by the microorganisms, and the following can be used: carbohydrates such as glucose, fructose, sucrose, molasses containing them, starch and starch hydrolyzates; organic acids such as acetic acid and propionic acid; alcohols such as ethanol and propanol, and the like.

As the nitrogen source, the following can be used: ammonia; ammonium salts of various inorganic acids or organic acids, such as ammonium chloride, ammonium sulfate, ammonium acetate, and ammonium phosphate; other nitrogen-containing compounds; peptone; meat extracts; yeast extracts; corn steep liquor; casein hydrolyzates; soy bean meal; soy bean meal hydrolyzates; various fermented cells and hydrolyzates thereof; and the like.

As the inorganic salts, the following can be used: potassium dihydrogenphosphate, dipotassium hydrogenphosphate, magnesium phosphate, magnesium sulfate, sodium chloride, ferrous sulfate, manganese sulfate, copper sulfate, calcium carbonate, and the like.

The culturing is conducted under aerobic conditions using, e.g., shaking culture or submerged spinner culture under aeration.

The culturing temperature is preferably 15 to 40° C., and the culturing period is usually 5 hours to 7 days.

During the culturing, pH is maintained at 3.0 to 9.0. Adjustment of the medium pH is conducted using an inorganic or organic acid, an alkaline solution, urea, calcium carbonate, ammonia, and the like.

If necessary, antibiotics such as ampicillin and tetracycline may further be added to the medium during the culturing.

For culturing a microorganism transformed with an expression vector using an inducible promoter as a promoter, an inducer may be added to the medium, if necessary. For example, for culturing a microorganism transformed with an expression vector using lac promoter, isopropyl-β-D-thiogalactopyranoside, or the like, may be added to the medium; for culturing a microorganism transformed with an expression vector using trp promoter, indole acrylic acid, or the like, may be added to the medium.

When the transformants for producing the polypeptide of the present invention are animal cells, the medium for culturing the cells is a generally employed medium such as RPMI1640 medium [The Journal of the American Medical Association, 199, 519 (1967)], Eagle's MEM medium [Science, 122, 501 (1952)], DMEM medium [Virology, 8, 396 (1959)], 199 medium [Proceeding of the Society for the Biological Medicine, 73, 1 (1950)] or any of these media further supplemented with fetal calf serum.

The culturing is conducted usually at pH 6 to 8 at 25 to 40° C. for 1 to 7 days in the presence of 5% $CO_2$.

If necessary, antibiotics such as kanamycin, penicillin and streptomycin may be added to the medium during the culturing.

When the transformants for producing the polypeptide of the present invention are insect cells, the medium for culturing said cells may be a generally employed medium such as TNM-FH medium (a product of Pharmingen), Sf-900 II SFM medium (a product of GIBCO BRL), ExCell 400 and ExCell 405 [both are products of JRH Biosciences] and Grace's Insect Medium [Nature, 195, 788 (1962)].

The culturing is conducted usually at pH 6 to 7 at a temperature of 25 to 30° C. for 1 to 5 days.

If necessary, antibiotics such as gentamycin may be added to the medium during the culturing.

The method of expressing the gene includes a method of expressing a partial polypeptide containing a region having β1,3-galactosyltransferase activity besides the full-length polypeptide. Generally, glycosyltransferase has the topology of type 2 transmembrane protein and consists of a cytoplasmic region consisting of a few to decades of N-terminal amino acids, a membrane-binding region containing highly hydrophobic amino acids, a stem region consisting of a few to decades of amino acids, and a large C-terminal region containing a catalytic domain. It is estimated that the stem region and the large C-terminal region containing a catalytic domain are exposed to the lumen of the Golgi body. The border between the stem region and the catalytic domain can be experimentally determined by examining the disappearance of the activity of the polypeptide while deleting its N-terminal region. The stem region and the catalytic domain can also be estimated by comparison with the amino acid sequence of analogous glycosyltransferase whose stem region and catalytic domain have been revealed.

The structure of the novel β1,3-galactosyltransferase of the present invention also has similar structure to those of other glycosyltransferases.

For example, the polypeptide of the present invention having the amino acid sequence represented by SEQ ID NO: 1 consists of a cytoplasmic region consisting of N-terminal seven amino acids, a highly hydrophobic membrane-binding region consisting of 19 amino acids, a stem region consisting of at least 4 amino acids, and a large C-terminal region containing a catalytic domain. On the basis of comparison of its homology in amino acid sequence to other β1,3-galactosyltransferases and information on the stem region and catalytic domain of other β1,3-galactosyltransferases [Japanese Published Unexamined Patent Application No. 181759/94], it is estimated that the stem region consists of at least 4 amino acids. Accordingly, a partial polypeptide containing the amino acid sequence of 31 to 310 is considered to contain the catalytic domain.

The full-length polypeptide described above or the partial polypeptide containing the region having β1,3-galactosyltransferase activity (catalytic domain) can be expressed directly or as a secreted protein or fusion protein in accordance with the methods described in Molecular Cloning, 2nd edition. The protein to be fused includes β-galactosidase, protein A, IgG-binding region of protein A, chloramphenicol acetyltransferase, poly(Arg), poly(Glu), protein G, maltose-binding protein, glutathione S-transferase, polyhistidine chain (His-tag), S peptide, DNA-binding protein domain, Tac antigen, thioredoxin, green fluorescence protein, and any antibody epitope [Akio Yamakawa: Jikken Igaku (Experimental Medicine), 13, 469–474 (1995)].

The method of producing the polypeptide of the present invention includes intracellular production by host cells, extracellular secretion by host cells or production on outer membranes by host cells, and the method can be selected depending on the host cells used or on alteration of the structure of the polypeptide to be produced.

When the polypeptide of the present invention is produced in host cells or on outer membranes of host cells, it is possible to force the polypeptide to be secreted outside the host cells by use of the method of Paulson, et al. [J. Biol. Chem., 264, 17619 (1989)], the method of Lowe, et al. [Proc. Natl. Acad. Sci., USA, 86, 8227 (1989), Genes Develop., 4, 1288 (1990)] or methods described in Japanese Published Unexamined Patent Application No. 336963/93, WO94/23021, etc.

That is, the polypeptide of the present invention can be secreted outside the host cells by expressing it as a form in which a signal peptide is added upstream of a polypeptide portion containing the active site of the polypeptide of the present invention, which can be achieved using gene manipulation techniques.

Specifically, it is possible to force the polypeptide of the present invention to be secreted outside the host cells by expressing it in the form in which a signal peptide is added upstream of a polypeptide portion containing the amino acid sequence of 31 to 310 considered to contain the catalytic site. Further, a tag for purification and detection can also be added between the signal peptide and the polypeptide containing the catalytic domain or to the C-terminus of the polypeptide containing the catalytic domain. The tag for purification and detection includes β-galactosidase, protein A, IgG-binding region of protein A, chloramphenicol acetyltransferase, poly(Arg), poly(Glu), protein G, maltose-binding protein, glutathione S-transferase, polyhistidine chain (His-tag), S peptide, DNA-binding protein domain, Tac antigen, thioredoxin, green fluorescence protein, and any antibody epitope [Akio Yamakawa: Jikken Igaku (Experimental Medicine), 13, 469–474 (1995)].

The amount of the polypeptide produced can be increased by a gene amplification system using a dihydrofolate reductase gene, or the like, according to the method described in Japanese Published Unexamined Patent Application No. 227075/90.

For isolation and purification of the polypeptide of the present invention from a culture of the transformant for producing the polypeptide of the present invention, conventional methods for the isolation and purification of enzymes can be used.

For example, when the polypeptide of the present invention is accumulated in a soluble form in the transformant cells for producing the polypeptide of the present invention, the cells are recovered from the culture by centrifugation, then washed and disrupted with a sonicator, French Press, Manton-Gaulin homogenizer, Dynomill, or the like, to obtain a cell-free extract.

A purified preparation can be obtained by centrifuging the cell-free extract to obtain the supernatant and then by subjecting the supernatant to extraction with a solvent, salting-out with ammonium sulfate, etc., desalting, precipitation with organic solvent, anion-exchange chromatography on resin such as diethylaminoethyl (DEAE)-Sepharose, DIAION HPA-75 (a product of Mitsubishi Chemical Industries Ltd.), or the like, cation-exchange chromatography on resin such as S-Sepharose FF (a product of Pharmacia), or the like, hydrophobic chromatography on resin such as butyl Sepharose, phenyl Sepharose, or the like, gel filtration using molecular sieve, affinity chromatography, chromatofocusing, and electrophoresis such as isoelectric focusing, or the like.

When said polypeptide is expressed as an inclusion body in cells, the cells are similarly recovered, disrupted and centrifuged to obtain a precipitate fraction. From the fraction, the polypeptide is then recovered in a usual manner, and the inclusion body of the polypeptide is solubilized with a polypeptide denaturating agent. The solubilized solution is then diluted with, or dialyzed against, a solution not containing the polypeptide-denaturating agent or a solution containing the polypeptide-denaturating agent at such a low concentration that denaturation of the polypeptide is not caused, whereby the solubilized polypeptide is renatured to have normal higher-order structure, and its purified preparation can be obtained by use of the same isolation and purification methods as described above.

When said polypeptide is extracellularly secreted, the culture is subjected to means such as centrifugation to give a soluble fraction. From the soluble fraction, a purified preparation of said polypeptide can be obtained in the same manner as for isolation and purification from the cell-free extract as described above.

Further, the polypeptide of the present invention can be purified in accordance with a usual method of purifying transferase [Methods in Enzymology, 83, 458].

Furthermore, it is possible to produce the polypeptide of the present invention as a fusion protein with another protein and to purify it by affinity chromatography using a substance having affinity for the fused protein [Akio Yamakawa: Jikken Igaku (Experimental Medicine), 13, 469–474 (1995)].

For example, according to the method of Lowe, et al. [Proc. Natl. Acad. Sci., USA, 86, 8227 (1989), Genes Develop., 4, 1288 (1990)] or the methods described in Japanese Published Unexamined Patent Application No. 336963/93 and WO94/23021, the polypeptide of the present invention can be produced as a fusion protein with protein A and can be purified by affinity chromatography using immunoglobulin G.

Further, it is possible to produce the polypeptide of the present invention as a fusion protein with a FLAG peptide and to purify it by affinity chromatography using anti-FLAG antibody [Proc. Natl. Acad. Sci., USA, 86, 8227 (1989), Genes Develop., 4, 1288 (1990)].

Furthermore, the polypeptide can also be purified by affinity chromatography using an antibody against said polypeptide itself.

The polypeptide of the present invention can be produced by in vitro transcription-translation system in accordance with known methods [J. Biomolecular NMR, 6, 129–134, Science, 242, 1162–1164, J. Biochem., 110, 166–168 (1991)].

On the basis of the amino acid information on the polypeptide obtained above, the polypeptide of the present invention can also be produced by chemical synthetic methods such as the Fmoc method (the fluorenylmethyloxycarbonyl method), the tBoc method (the t-butyloxycarbonyl method), etc. The polypeptide can also be chemically synthesized by a peptide synthesizer from Advanced ChemTech, Perkin Elmer, Pharmacia Biotech, Protein Technology Instrument, Synthecell-Vega, PerSeptive, Shimadzu Corporation, etc.

The structural analysis of the purified polypeptide of the present invention can be carried out according to the method described in, e.g., Structural Analysis of Protein for Gene Cloning (written by Hisashi Hirano and published by Tokyo Kagaku Dojin, 1993).

The β1,3-galactosyltransferase activity of the polypeptide of the present invention can be measured according to a known measuring method [J. Biol. Chem., 258, 9893–9898 (1983), J. Biol. Chem., 262, 15649–15658 (1987), Archi. Biochem. Biophys., 270, 630–646 (1989), Archi. Biochem. Biophys., 274, 14–25 (1989), Japanese Published Unexamined Patent Application No. 181759/94, J. Biol. Chem., 273, 58–65 (1998), J. Biol. Chem., 273, 433–440 (1998), J. Biol. Chem., 273, 12770–12778 (1998)].

(3) Production of Sugar Chains Having Galactose Transferred via β1,3-linkage to N-acetylglucosamine, N-acetylglucosamine Residue, Glucose, or Glucose Residue Thereof or Complex Carbohydrates Containing said Sugar Chains.

Sugar chains having galactose transferred via β1,3-linkage to N-acetylglucosamine, N-acetylglucosamine residue, glucose or glucose residue thereof or complex carbohydrates containing said sugar chains can be produced by culturing in a medium a transformant selected from the group consisting of the transformants derived from microorganisms, animal cells, plant cells and insect cells obtained in item (2) above, to thereby form and accumulate said sugar chains or said complex carbohydrates in the culture, and collecting said sugar chains or said complex carbohydrates from the culture.

The sugar chains having galactose transferred via β1,3-linkage to N-acetylglucosamine residue thereof include sugar chains having sialyl-Lewis a structure, sugar chains having sialyl-Lewis c structure, sugar chains having Lewis a structure, sugar chains having Lewis b structure, sugar chains having Galα1-3Galβ1-3GlcNAc structure, sugar chains having Galα1-3(Fucα1-2)Galβ1-3GlcNAc structure and sugar chains having GalNAcα1-3(Fucα1-2)Galβ1-3GlcNAc structure.

The culturing can be conducted in accordance with item (2) above.

By producing the polypeptide of the present invention and any recombinant glycoprotein (e.g., pharmaceutical recombinant glycoprotein) simultaneously in the transformant described above, sugar chains having galactose transferred via β1,3-linkage to N-acetylglucosamine, N-acetylglucosamine residue, glucose or glucose residue thereof can be added to the recombinant glycoprotein.

Further, the sugar chains having galactose transferred via β1,3-linkage to N-acetylglucosamine, N-acetylglucosamine residue, glucose or glucose residue thereof, or complex carbohydrates containing said sugar chains added thereto, can be produced in accordance with the method described in item (2) above by using the animal or plant obtained in item (2) above.

That is, in the case of the animal, for example, a non-human transgenic animal harboring the DNA of the present invention is raised so that sugar chains having galactose transferred via β1,3-linkage to N-acetylglucosamine, N-acetylglucosamine residue, glucose or glucose residue thereof, or complex carbohydrates containing said sugar chains added thereto, are formed and accumulated in the animal, and said products are recovered from the animal whereby the sugar chains having galactose transferred via β1,3-linkage to N-acetylglucosamine, N-acetylglucosamine residue, glucose or glucose residue thereof, or complex carbohydrates containing said sugar chains added thereto, can be produced.

The place where these products are formed and accumulated in the animal is, for example, milk and egg of the animal.

In the case of the plant, for example, a transgenic plant harboring the DNA of the present invention is cultured so that sugar chains having galactose transferred via β1,3-linkage to N-acetylglucosamine, N-acetylglucosamine residue, glucose or glucose residue thereof, or complex carbohydrates containing said sugar chains added thereto, are formed and accumulated in the plant, and said products are recovered from the plant whereby the sugar chains having galactose transferred via β1,3-linkage to N-acetylglucosamine, N-acetylglucosamine residue, glucose or glucose residue thereof, or complex carbohydrates containing said sugar chains added thereto, can be produced.

Reaction products having galactose transferred via β1,3-linkage to N-acetylglucosamine residues present at the non-reducing termini of sugar chain thereof or to N-acetylglucosamine monosaccharides can be produced in an aqueous medium in the following method using the polypeptide of the present invention obtained in the method described in item (2) above as the enzyme source.

That is, N-acetylglucosamine monosaccharides, oligosaccharides having N-acetylglucosamine residue at the non-reducing termini thereof, or complex carbohydrates having N-acetylglucosamine residue at the non-reducing termini of sugar chains thereof, are used as the acceptor substrate while the polypeptide of the present invention obtained in the method described in item (2) above is used as the enzyme source, and reaction products having galactose transferred via β1,3-linkage to N-acetylglucosamine monosaccharide or N-acetylglucosamine residue of the acceptor substrate can be produced by allowing said receptor substrate, said enzyme source and uridine-5'-diphosphate galactose (UDP-Gal) to be present in an aqueous medium to thereby form and accumulate said reaction products in said aqueous medium and collecting said reaction products from said aqueous medium.

Reaction products having galactose transferred via 1,3-linkage to glucose residues present at the non-reducing termini of sugar chains thereof or to glucose monosaccharides can be produced in an aqueous medium in the following method using the polypeptide of the present invention obtained in the method described in item (2) above as the enzyme source.

That is, glucose monomers, oligosaccharides having glucose residue at the non-reducing termini thereof, or complex carbohydrates having glucose residue at the non-reducing termini of sugar chains thereof are used as the acceptor substrate while the polypeptide of the present invention obtained in the method described in item (2) above is used as the enzyme source, and reaction products having galactose transferred via β1,3-linkage to glucose monomers or glucose residues of the receptor substrate can be produced by allowing said acceptor substrate, said enzyme source and UDP-Gal to be present in an aqueous medium to thereby form and accumulate said reaction products in said aqueous medium and collecting said reaction products from said aqueous medium.

The enzyme source is used at a concentration of 0.1 mU/l to 10,000 U/l, preferably 1 mU/l to 1,000 U/l where 1 U refers to the activity by which 1 μmol lacto-N-tetraose, Galβ1-3GlcNAcβ1-3Galβ1-4Glc can be formed at 37° C. for 1 minute from agalact lacto-N-neotetraose, GlcNAcβ1-3Galβ1-4Glc as the substrate.

The aqueous medium includes water, buffers such as phosphates, carbonates, acetates, borates, citrates and Tris, alcohols such as methanol and ethanol, esters such as ethyl acetate, ketones such as acetone, and amides such as acetamide. Further, the culture solution of the microorganism used as the enzyme source can be used as the aqueous medium. A transformant's culture solution obtained by the culturing described in item (2) above, or milk obtained from the non-human transgenic animal described in item (2) above, can also be used as the aqueous medium.

A surfactant or an organic solvent may be added as necessary to the aqueous medium.

The surfactant may be any one capable of promoting formation of Gal-containing sugars, and examples of such surfactants include nonionic surfactants such as polyoxyethylene octadecylamine (e.g., Nimean S-215, a product of Nippon Oil and Fats Co., Ltd.), cationic surfactants such as cetyl trimethyl ammonium bromide and alkyl dimethyl benzyl ammonium chloride (e.g., Cation F2-40E, a product of Nippon Oil and Fats Co., Ltd.), anionic surfactants such as lauroyl sarcosinate, tertiary amines such as alkyl dimethyl amine (e.g., tertiary amine FB, a product of Nippon Oil and Fats Co., Ltd.), and these can be used alone or in combination thereof.

The surfactant is used usually at a concentration of 0.1 to 50 g/l.

The organic solvent includes xylene, toluene, fatty alcohol, acetone and ethyl acetate, and is used usually at a concentration of 0.1 to 50 ml/l.

As UDP-Gal, a commercial product or a reaction solution formed by the activity of a microorganism, etc. or a purified product from the reaction solution can be used. The UDP-Gal can be used at a concentration of 0.1 to 500 mmol/l.

The oligosaccharides having N-acetylglucosamine residue at the non-reducing termini thereof include GlcNAcβ1-

3Galβ1-4Glc, GlcNAcβ1-3Galβ1-4GlcNAc, GlcNAcβ1-3 (GlcNAcβ1-6)Galβ1-4Glc, GlcNAcβ1-3(GlcNAcβ1-6) Galβ1-4GlcNAc, GlcNAcβ1-3GalNAc, GlcNAcβ1-6GalNAc, and oligosaccharides having one of said oligosaccharide structures at the non-reducing termini of sugar chains thereof.

The complex carbohydrates having N-acetylglucosamine residue at the non-reducing termini of sugar chains thereof include complex carbohydrates having one of said oligosaccharide structures at the non-reducing termini of sugar chains thereof, or complex carbohydrates containing asialogalacto complex N-linked sugar chains.

The acceptor substrate can be used at a concentration of 0.01 to 500 mmol/l.

In said formation reaction, inorganic salts such as $MnCl_2$, etc., β-mercaptoethanol, polyethylene glycol, etc. can be added as necessary.

The formation reaction is carried out at 20 to 50° C. for 1 to 96 hours in an aqueous medium, pH 5 to 10, preferably pH 6 to 8.

From the sugar chains or complex carbohydrates produced by the method described above, a part of the sugar chains can be cleaved off by conventional enzymatic or chemical means ["Zoku Seikagaku Jikken Koza" (Sequel to Lecture of Experiments in Biochemistry), Vol. 4, "Fukugotoshitsu Kenkyuho I & II" (Method for Study of Complex Carbohydrates), ed. by Japanese Biochemistry Society and published by Tokyo Kagaku Dojin K. K. (1986); N. Taniguchi, A. Suzuki, K. Furukawa, K. Sugawara: Experimental Protocol in Glycobiology, published by Shujunsha (1996)].

(4) Preparation of an Antibody Recognizing the Polypeptide of the Present Invention (i) Preparation of a Polyclonal Antibody A polyclonal antibody can be prepared by using a purified product of the full-length polypeptide or a partial fragment of the polypeptide obtained by the method described in item (2) above as the antigen and administering the antigen to an animal.

The animals to which the antigen is administered include rabbits, goats, rats, mice and hamsters.

Preferable dosage of antigen is 50 to 100 μg per animal.

When a peptide is used as the antigen, it is preferred to use the peptide as the antigen after binding it covalently to a carrier protein such as keyhole limpet hemocyanin, bovine thyroglobulin, or the like. The peptide used as the antigen can be synthesized by a peptide synthesizer.

Administration of the antigen is carried out 3 to 10 times at one- to two-week intervals after the first administration. A blood sample is recovered from the fundus oculi veniplex of the eye on the third to seventh day after each administration, and the serum is examined for reactivity to the antigen used for immunization, for example, by enzyme immunoassay [Enzyme-linked Immunosorbent Assay (ELISA), published by Igaku Shoin (1976); Antibodies—A Laboratory Manual, Cold Spring Harbor Laboratory (1988)].

A polyclonal antibody can be prepared by obtaining the serum from a non-human mammal whose serum shows a sufficient antibody titer against the antigen used for immunization, isolating and purifying it from the serum.

With regard to the method for isolation and purification of the polyclonal antibody, centrifugation, salting-out method with 40 to 50% saturated ammonium sulfate, caprylic acid precipitation method [Antibodies, A Laboratory manual, Cold Spring Harbor Laboratory (1988)], or chromatographic methods using a DEAE-Sepharose column, an anion exchange column, a protein A or G column, a gel filtration column, and the like, may be employed alone or in combination.

(ii) Preparation of a Monoclonal Antibody (a) Preparation of Antibody-Producing Cells The non-human mammal whose serum shows adequate antibody titer against a partial fragment of the polypeptide of the present invention used in immunization is used as a source of antibody-producing cells.

On the third to seventh day after the final administration of the antigen to a rat with said antibody titer, the spleen is excised from the rat. The spleen is cut into pieces in MEM medium (a product of Nissui Pharmaceuticals, Co.) and the pieces are then loosened with tweezers, followed by centrifugation at 1,200 rpm for 5 minutes, to discard the resulting supernatant.

The spleen cells in the resulting precipitated fraction are treated with a Tris-ammonium chloride buffer (pH 7.65) for 1 to 2 minutes to remove erythrocytes, followed by washing 3 times with MEM medium to give spleen cells as antibody-producing cells.

(b) Preparation of Myeloma Cells

As myeloma cells, cell lines obtained from mice or rats are used. For example, 8-azaguanine-resistant mice (BALB/c-derived) myeloma cell line P3-X63Ag8-U1 (hereinafter abbreviated to P3-U1) [Curr. Topics. Microbiol. Immunol., 81, 1 (1978), Europ. J. Immunol., 6, 511 (1976)], SP2/0-Ag14 (SP-2) [Nature, 276, 269 (1978)], P3-X63-Ag8653 (653) [J. Immunol., 123, 1548 (1979)] and P3-X63-Ag8 (X63) [Nature, 256, 495 (1975)] can be used. These cell lines are further subjected to subculture in 8-azaguanine medium [medium prepared by adding 8-azaguanine (15 μg/ml) to a medium (referred to hereinafter as normal medium) having glutamine (1.5 mmol/l), 2-mercaptoethanol ($5 \times 10^{-5}$ mol/l), gentamicin (10 μg/ml) and fetal calf serum (FCS) (a product of CSL Ltd.; 10%) added to RPMI-1640 medium], and 3 to 4 days before cell fusion, they are cultured in the normal medium and at least $2 \times 10^7$ cells are used for fusion.

(c) Preparation of Hybridoma

The antibody-producing cells obtained in item (a) above and myeloma cells obtained in item (b) above are washed well with MEM medium or PBS (1.83 g of disodium phosphate, 0.21 g of monopotassium phosphate, 7.65 g of common salt, 1 L of distilled water, pH 7.2) and mixed such that the ratio of the antibody-producing cells/myeloma cells ranges from 5/1 to 10/1, and the mixture is centrifuged at 1,200 rpm for 5 minutes and the supernatant is discarded.

The cell pellet obtained as the precipitated fraction is well loosened, and a mixture containing 2 g of polyethylene glycol-1000 (PEG-1000), 2 ml of MEM and 0.7 ml of dimethyl sulfoxide (DMSO) is added to the cells in a volume of 0.2 to 1 ml/$10^8$ antibody-producing cells with stirring at 37° C., and 1 to 2 ml of MEM medium is added thereto several times at 1 to 2-minute intervals.

After addition, MEM medium is added to adjust the total volume to 50 ml. The solution thus prepared is centrifuged at 900 rpm for 5 minutes, and the supernatant is discarded.

The cells obtained in the precipitated fraction are gently loosened and suspended by pipetting in 100 ml of HAT medium [the medium prepared by adding hypoxanthine ($10^{-4}$ mol/l), thymidine ($1.5 \times 10^{-5}$ mol/l) and aminopterin ($4 \times 10^{-7}$ mol/l) to the normal medium].

The suspension is put to each well on a 96-well culture plate (100 µl/well) and cultured at 37° C. in a 5% $CO_2$ incubator for 7 to 14 days.

After culturing, an aliquot of the supernatant is sampled and a hybridoma reacting specifically with a partial fragment of the polypeptide of the present invention is selected by enzyme immunoassays described in, e.g., "Antibodies" [Antibodies, A Laboratory Manual, Cold Spring Harbor Laboratory, Chapter 14 (1988)].

Specifically, enzyme immunoassays are conducted as follows:

An appropriate plate is coated with a partial fragment of the polypeptide of the present invention, which is used as an antigen for immunization, followed by reaction with a culture supernatant of the hybridoma or with the purified antibody obtained in (d) below as a first antibody and then with anti-rat or anti-mouse immunoglobulin antibody as a second antibody labeled with biotin, an enzyme, a chemiluminescent substance or a radioisotope. Then, reaction depending on the labeling substance is conducted, and a hybridoma reacting specifically with the polypeptide of the present invention is selected as a hybridoma producing the monoclonal antibody of the present invention.

Using the hybridoma, cloning is repeated twice by limiting dilution [for first dilution, HT culture medium (aminopterin-free HAT medium) is used; for second dilution, the normal medium is used]. A hybridoma showing a stable and strong antibody titer is selected as the hybridoma producing an antibody against the polypeptide of the present invention.

(d) Preparation of a Monoclonal Antibody

The hybridoma cells producing a monoclonal antibody against the polypeptide of the present invention, obtained in item (c) above, are injected at a dose of 5 to 20×10$^6$ cells/animal into the abdomens of 8 to 10-week-old mice or nude mice treated with 0.5 ml Pristane [animals raised for 2 weeks after intraperitoneal administration of 2,6,10,14-tetramethylpentadecane (Pristane)]. The hybridoma forms ascites tumor in 10 to 21 days.

From the mouse with the ascites tumor, the ascites is collected and centrifuged at 3,000 rpm for 5 minutes, to remove the solid matters from the fluid.

From the resulting supernatant, the monoclonal antibody can be purified and obtained according to the same method as used for the polyclonal antibody.

The class and subclass of the antibody are determined using a mouse monoclonal antibody typing kit or a rat monoclonal antibody typing kit. The class of the antibody means isotype of the antibody, and for example, mention can be made of IgG, IgA, IgM, IgD and IgE in human. The subclass of the antibody means isotype in the class, and for example, mention can be made of IgG1, IgG2a, IgG2b and IgG3 in mouse, and IgG1, IgG2, IgG3 and IgG4 in human.

The amount of protein of the antibody is calculated by the Lowry method or from its absorbance at 280 nm.

(5) Application of the DNA or Oligonucleotide of the Present Invention to Treatment, Diagnosis, etc. of Diseases The DNA of the present invention can be applied to treatment of diseases, such as inhibition of cancer metastasis, etc., by use of antisense RNA/DNA technology [Bioscience and Industry, 50, 322 (1992); "Kagaku" (Chemistry), 46, 681 (1991); Biotechnology, 9, 358 (1992); Trends in Biotechnology, 10, 87 (1992); Trends in Biotechnology, 10, 152 (1992); "Saibo Kogaku" (Cell Engineering), 16, 1463 (1997)] or by use of triple helix technology [Trends in Biotechnology, 10, 132 (1992)] as well as to diagnosis of such diseases by use of Northern hybridization or PCR techniques.

For example, production of the polypeptide of the present invention can be inhibited by administering the DNA or oligonucleotide of the present invention described in item (1) above or its derivative.

That is, the DNA or oligonucleotide of the present invention or a derivative thereof can be used for inhibition of transcription of DNA coding for the polypeptide of the present invention or for inhibition of translation of mRNA coding for the polypeptide of the present invention.

Furthermore, expression level of DNA coding for the polypeptide of the present invention can be determined by Northern hybridization or PCR using the DNA of the present invention or the above oligonucleotide prepared from the DNA.

A promoter region of said gene can be obtained by using the DNA of the present invention as a probe in a known method ["Shin Saibo Kogaku Jikken Protocol" (New Experimental Protocol in Cell Engineering), edited by Department of Anticancer Research, Medical Research Institute, Tokyo University and published by Shujunsha (1993)].

At present, the sequences of many human chromosomal genes whose functions are not known are registered in a database. Accordingly, by comparing the sequence of human cDNA coding for the polypeptide of the present invention with the sequences of human chromosomal genes registered in a database, the human chromosomal gene coding for the polypeptide of the present invention may be identified to reveal the structure of said gene. If a chromosomal gene sequence consistent with the sequence of said cDNA is registered, the promoter region and exon and intron structures in the chromosomal gene coding for the polypeptide of the present invention can be determined by comparing the sequence of the cDNA with the sequence of the above consistent chromosomal gene.

The promoter region may be any promoter region participating in transcription of the gene coding for the polypeptide of the present invention in mammalian cells. For example, mention can be made of promoter regions participating in transcription of the gene coding for the polypeptide of the present invention in human colon cancer cells or human pancreatic cancer cells. For example, mention can be made of a promoter DNA having a consecutive 50- to 5000-bp sequence in the nucleotide sequence of 1 to 5000 in the nucleotide sequence represented by SEQ ID NO: 3. Said promoter can be used in the screening method described below.

It is known that polymorphism and mutations occur in a glycosyltransferase gene. With respect to glycosyltransferase involved in determination of ABO blood type, for example, the following 3 enzymes are formed according to the difference in amino acid sequence based on gene polymorphism:

α1,3-N-acetylgalactosaminyltransferase involved in synthesis of A type antigen, α1,3-galactosyltransferase involved in synthesis of B type antigen, and an enzyme having no activity, which is involved in formation of O(H) type sugar chains [Nature, 345, 229–233 (1990)].

It is also known that the activity of α1,3-fucosyltransferase (Fuc-TIII) involved in determination of Lewis blood type is reduced or disappears depending on the difference in amino acid sequence based on gene polymorphism [J. Biol. Chem., 269, 29271–29278 (1994), Blood, 82, 2915–2919

(1993), J. Biol. Chem., 269, 20987–20994 (1994), J. Biol. Chem., 272, 21994–21998 (1997)].

It is known that the polymorphism of Fuc-TIII gene has a close relationship with expression of sialyl-Lewis a sugar chains that are cancer-related sugar chain antigens in colon cancers [Cancer Res., 56, 330–338 (1996), Cancer Res., 58, 512–518 (1998)].

Accordingly, it is considered that diagnosis of diseases or prediction of prognosis can be performed by examining the polymorphism of Fuc-TIII.

Since the novel β1,3-galactosyltransferase of the present invention is involved in the synthesis of sialyl-Lewis a sugar chains or sialyl-Lewis c sugar chains in colon cancers or pancreatic cancers, diagnosis of colon cancers and pancreatic cancers or prediction of prognosis can be performed by examining the polymorphism of this gene.

Further, diagnosis of other diseases can also be performed by examining the relationship of the polymorphism of this gene with organs (stomach, jejunum, colon, pancreas, etc.) expressing this gene.

Analysis of the polymorphism of this gene can be performed using the sequence information on this gene. Specifically, the polymorphism of the gene can be analyzed by Southern blotting, direct sequencing, PCR, a DNA chip method, etc. [Rinsho Kensa (Clinical Examination), 42, 1507–1517 (1998); Rinsho Kensa, 42, 1565–1570 (1998)].

(6) Use of the Polypeptide of the Present Invention (a) Use Thereof for Preparation of the Antibody of the Present Invention The polypeptide of the present invention can be used to prepare the antibody of the present invention by the method described in item (4) above.

(b) Use of the Polypeptide of the Present Invention for Production of Sugar Chains and Complex Carbohydrates The polypeptide of the present invention can be used to produce sugar chains having galactose transferred via β1,3-linkage to N-acetylglucosamine, N-acetylglucosamine residue, glucose or glucose residue thereof, or complex carbohydrates having said sugar chains added thereto.

(c) Use Thereof for Screening a Substance Participating in the Activity of the Polypeptide of the Present Invention The polypeptide of the present invention can be used for screening a compound enhancing or inhibiting the activity of said polypeptide by the method (a) described in item (8) below.

(7) Use of the Antibody of the Present Invention (a) Immunological Detection and Quantification of the Polypeptide of the Present Invention by the Antibody of the Present Invention The method for immunological detection of the polypeptide of the present invention includes ELISA using a microtiter plate, fluorescence antibody technique, Western blotting, immunohistostaining, etc.

The immunological quantification method includes the sandwich ELISA using two monoclonal antibodies which react different epitopes of the polypeptide of the present invention in a liquid phase and the radioimmunoassay using the polypeptide of the present invention labeled with radioisotopes such as $^{126}I$ and the antibody recognizing the polypeptide of the present invention.

The detection method or quantification method described above can be applied to diagnosis of colon cancers, pancreatic cancers, etc.

(b) Pharmaceutical Preparation Containing the Antibody of the Present Invention

The antibody of the present invention can be used as an agent for treating diseases such as colon cancers, pancreatic cancers, etc.

As the pharmaceutical preparation comprising the antibody of the present invention, said compound can be administered alone as a therapeutic agent, but usually it is mixed with pharmacologically acceptable, one or more carriers and provided as a pharmaceutical preparation produced by a well-known method in the technical field of pharmaceutical manufacturing.

The administration route is preferably the most effective route for treatment, and includes oral administration and parenteral administration such as intra-oral cavity administration, intratracheal administration, intrarectal administration, subcutaneous administration, intramuscular administration and intravenous administration. The administration form includes sprays, capsules, tablets, granules, syrups, emulsions, suppositories, injections, ointments and tapes.

The pharmaceutical preparation suitable for oral administration includes emulsions, syrups, capsules, tablets, powders and granules. For example, liquid preparations such as emulsions and syrups can be produced by using water, saccharides such as sucrose, sorbitol and fructose, glycols such as polyethylene glycol and propylene glycol, oils such as sesame oil, olive oil and soybean oil, preservatives such as p-hydroxybenzoate and flavors such as strawberry flavor and peppermint as additives. The capsules, tablets, powders and granules can be produced by using excipients such as lactose, glucose, sucrose and mannitol, disintegrating agents such as starch and sodium alginate, lubricants such as magnesium stearate and talc, binders such as polyvinyl alcohol, hydroxypropyl cellulose and gelatin, surfactants such as fatty acid esters and plasticizers such as glycerin as additives.

The pharmaceutical preparation suitable for parenteral administration includes injections, suppositories and sprays. For example, the injections are prepared by using carriers such as a salt solution, glucose solution or a mixture of the two. The suppositories are produced by using carriers such as cocoa butter, hydrogenated fats and carboxylic acids. The sprays are prepared from said compound alone or by using carriers for dispersing said compound as fine particles to facilitate absorption thereof without stimulating the oral cavity or tracheal mucous membrane of a recipient. Specific examples of such carriers include lactose and glycerin. Depending on said compound and the properties of the carriers used, preparations such as aerosols and dry powders can be manufactured. In these parenteral preparations, the ingredients exemplified as additives in the oral preparations can also be added.

The dose and administration frequency are varied depending on the desired therapeutic effect, administration method, period of treatment, age, body weight, etc., but the dose is usually 10 μg/kg to 8 mg/kg per day in an adult.

(8) Application to Screening Methods

The novel β1,3-galactosyltransferase polypeptide of the present invention is involved in the synthesis of type 1 sugar chains such as sialyl-Lewis a sugar chain, sialyl-Lewis c sugar chain, Lewis a sugar chain and Lewis b sugar chain in cancer cells in the digestive system, such as colon cancer cells and pancreatic cancer cells, and thus a compound enhancing or inhibiting the activity of said polypeptide can be used to increase or decrease the amount of the type 1 sugar chains synthesized in the cells.

Further, a compound promoting or suppressing the transcription process for the gene coding for said polypeptide or the translation process from the transcript to the protein can regulate expression of said polypeptide, to regulate the amount of type 1 sugar chains synthesized in the cells.

The compound suppressing the amount of type 1 sugar chains synthesized is considered to be useful for suppression of cancer metastasis. On the other hand, the compound increasing the amount of type 1 sugar chains synthesized is considered to be useful for synthesis of type 1 sugar chains.

The compounds described above can be obtained by the following methods (a) to (e):

(a) The novel polypeptide of the present invention having $\beta$1,3-galactosyltransferase activity prepared by the method described in item (2) above (purified product, a cell extract or a culture supernatant from a transformant expressing said polypeptide) is used as the enzyme, and in the presence of a test sample, its $\beta$1,3-galactosyltransferase activity is measured according to known methods [J. Biol. Chem., 258, 9893–9898 (1983), J. Biol. Chem., 262, 15649–15658 (1987), Archi. Biochem. Biophys., 270, 630–646 (1989), Archi. Biochem. Biophys., 274, 14–25 (1989), Japanese Published Unexamined Patent Application No. 181759/94, J. Biol. Chem., 273, 58–65 (1998), J. Biol. Chem., 273, 433–440 (1998), J. Biol. Chem., 273, 12770–12778 (1998)], whereby a test compound having the activity of increasing or decreasing the $\beta$1,3-galactosyltransferase activity is selected and obtained.

(b) Cells expressing the polypeptide of the present invention or the transformant described in item (2) above are cultured for 2 hours to 1 week in the presence of a test sample by the culturing method described in item (2) above, and the amount of type 1 sugar chains such as sialyl-Lewis a sugar chain, sialyl-Lewis c sugar chain, Lewis a sugar chain and Lewis b sugar chain on the cell surface is determined using an antibody against each sugar chain, whereby a test compound having the activity of increasing or decreasing the amount of said sugar chains is selected and obtained.

The determination method using the antibody includes, e.g., detection methods such as ELISA using a microtiter plate, fluorescence antibody technique, Western blotting and immunohistostaining.

(c) Cells expressing the polypeptide of the present invention are cultured for 2 hours to 1 week in the presence of a test sample by the culturing method described in item (2) above, and then the amount of said polypeptide in the cells is determined using the antibody of the present invention described in item (4) above, whereby a test compound having the activity of increasing or decreasing the amount of said polypeptide is selected and obtained.

The determination method using the antibody of the present invention includes, e.g., detection methods such as ELISA using a microtiter plate, fluorescence antibody techniques, Western blotting and immunohistostaining.

(d) Cells expressing the polypeptide of the present invention are cultured for 2 hours to 1 week in the presence of a test sample by the culturing method described in item (2) above, and then the amount of transcripts produced from the gene coding for said polypeptide in the cells is determined by the method described in item (5) above such as Northern hybridization, PCR or the like, whereby a test compound having the activity of increasing or decreasing the amount of the transcripts is selected and obtained.

(e) A plasmid carrying the DNA to which a reporter gene is ligated downstream of a promoter obtained in item (4) above is prepared in the known method, and the plasmid is introduced into the animal cells described in item (2) above by the method described in item (2) above whereby a transformant is obtained. The transformant is cultured for 2 hours to 1 week in the presence of a test sample by the culturing method described in item (2) above, and the expression level of the reporter gene in the cells is determined by the known method ["Shin Saibo Kogaku Jikken Protocol" (New Experimental Protocol in Cell Engineering), edited by Department of Anticancer Research, Medical Research Institute, Tokyo University and published by Shujunsha (1993); Biotechniques, 20, 914 (1996); J. Antibiotics, 49, 453 (1996); Trends in Biochemical Sciences, 20, 448 (1995); "Saibo Kogaku" (Cell Engineering), 16, 581 (1997)], whereby a test compound having the activity of increasing or decreasing the expression level is selected and obtained.

Examples of reporter genes include chloramphenicol acetyltransferase gene, $\beta$-glucuronidase gene, $\beta$-galactosidase gene, $\beta$-lactamase gene, luciferase gene, aequorin gene and green fluorescent protein (GFP) gene.

(9) Creation of Knockout Non-Human Animals

Using a vector containing the DNA of the present invention, mutant clones in which the DNA coding for the polypeptide of the present invention on the chromosome is inactivated or replaced by an arbitrary sequence by known homologous recombination techniques [e.g., Nature, 326, 6110, 295 (1987), Cell, 51, 3, 503 (1987), etc.] can be produced from embryonic stem cells in objective non-human animals such as cattle, sheep, goats, pigs, horses, chickens, mice, etc. [e.g., Nature, 350, 6315, 243 (1991)].

The embryonic stem cell clones thus produced and blastocyst of fertilized eggs of non-human animals can be used for producing chimeras composed of embryonic stem cell clones and normal cells by techniques such as injection chimera method, aggregation chimera method, etc.

By crossing said chimeras with normal individuals, individuals in which the DNA coding for the polypeptide of the present invention on the chromosome in cells in the whole body is arbitrarily mutated can be obtained, and by crossing said individuals, homozygotes (knockout non-human animals) having the mutation on both homologous chromosomes can be obtained.

In this manner, the DNA coding for the polypeptide of the present invention on the chromosome in the animals can be mutated in an arbitrary position. For example, the translational region of the DNA coding for the polypeptide of the present invention on the chromosome can be mutated by base substitution, deletion, insertion, etc. to alter the activity of its product.

Further, by similar mutation of its expression-regulating region, the degree of expression, stage, tissue specificity, etc. can also be modified. Furthermore, by combination with the Cre-loxP system, the expression stage, expression site, expression level, etc. can also be regulated highly.

By way of example, it is known that by using a promoter to be expressed in a specific region in the brain, an objective gene is deleted in only that region [Cell, 87, 7, 1317 (1996)], or by using adenovirus expressing Cre, an objective gene is deleted in an organ-specific manner at a desired stage [Science, 278, 5335 (1997)].

It is, therefore, possible to create knockout non-human animals in which expression of the DNA coding for the polypeptide of the present invention on the chromosome can be regulated at an arbitrary stage or in a specific organ as described above, or the translational region or expression-regulating region contains arbitrary insertion, deletion or substitution.

In such knockout non-human animals, various diseases attributable to the polypeptide of the present invention can be induced at an arbitrary stage, at an arbitrary degree or in an arbitrary site.

Accordingly, the knockout non-human animal of the present invention can serve as a very useful animal model in treating or preventing various diseases attributable to the polypeptide of the present invention. In particular, the animal is very useful as a model for evaluation of agents for treating or preventing the diseases, functional foods, health foods, etc.

BRIEF DESCRIPTION OF DRAWINGS

FIG. 1, B shows the results of determination of the amount of transcripts of human β3Gal-T1, human β3Gal-T2, human β3Gal-T3 and human β3Gal-T4 in various human cancer cell lines by the quantitative PCR method. The amounts of the respective β1,3-galactosyltransferase gene transcripts in various cell lines are expressed as values relative to the amount (=1000) of the β-actin transcript considered to be expressed at a similar degree in any cells.

FIG. 3, B shows the results of indirect fluorescent antibody staining with anti-sialyl-Lewis a sugar chain antibody (19-9), anti-sialyl-Lewis c sugar chain antibody (DU-PAN-2), anti-Lewis a sugar chain antibody (7LE) or anti-Lewis b sugar chain antibody (TT42) and subsequent FACS analysis of HCT-15 cells (HCT-mock) having the control plasmid (pAMo) introduced therein, or HCT-15 cells (HCT-3 GT5H) having human β3Gal-T5 expression plasmid (pAMo-3GT5) introduced therein. The shaded histogram shows the result of analysis using A-PBS in place of DU-PAN-2.

FIG. 4, B shows the results of examination of expression of CA19-9 antigen-containing proteins in various human cancer cell lines by Western blotting analysis.

FIG. 6, B shows the structure of isoforms of human β3Gal-T5 cDNA. Their proportion is shown in percentage of the amount of each isoform expressed in Colo205 cells.

FIG. 6, C shows the results of examination of the expression level of each isoform of human β3Gal-T5 cDNA in Colo205 cells by the RT-PCR method. After RT-PCR was conducted with the combination of primers shown in FIG. 6, A, the reaction product was cleaved with a restriction enzyme (XbaI or BsmI) shown in FIG. 6, to specify the isoform. (−) means that the restriction enzyme treatment was not conducted. The left line shows molecular markers (100 bp ladder).

BEST MODE FOR CARRYING OUT THE INVENTION

Examples are shown below. Unless otherwise specified, the methods described in Molecular Cloning, 2nd edition were used as techniques in gene manipulation.

Example 1

Measurement of the Expression Levels of Type 1 Sugar Chains and Known β1,3-Galactosyltransferase Gene in Various Cell Lines By measuring the expression levels of type 1 sugar chains (sialyl-Lewis a sugar chain, Lewis a sugar chain, Lewis b sugar chain) and the known human β1,3-galactosyltransferase genes in various human cancer cell lines, an attempt was made to identify the β1,3-galactosyltransferase involved in the synthesis of type 1 sugar chains in colon cancer cell lines or pancreatic cancer cell lines.

Figure 1:
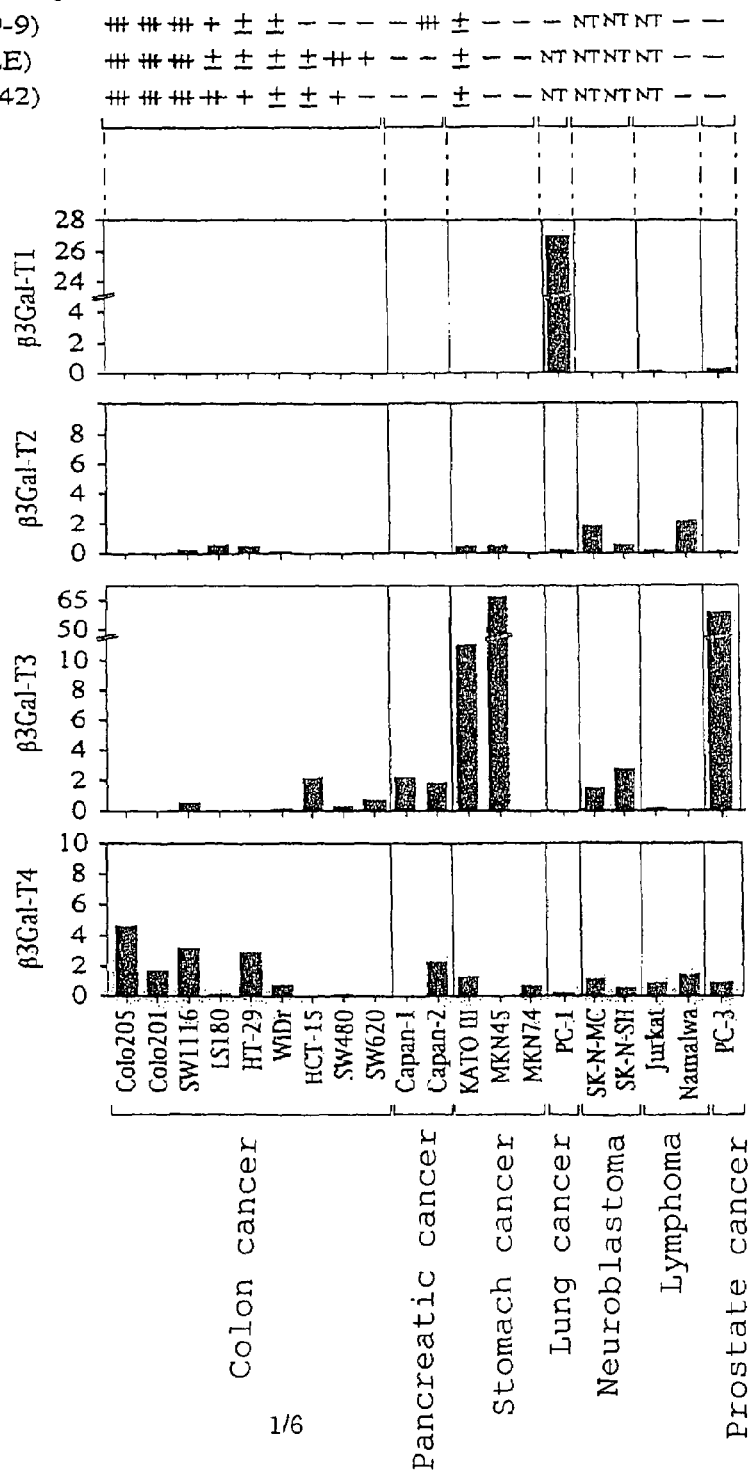
FIG. 1, A shows the results of measurement of the expression levels of type 1 sugar chains (sialyl-Lewis a sugar chain, Lewis a sugar chain, Lewis b sugar chain) in a wide variety of human cancer cell lines. Each kind of cell was stained with a fluorescent antibody using anti-sialyl-Lewis a sugar chain antibody (19-9), anti-Lewis a sugar chain antibody (7LE) or anti-Lewis b sugar chain antibody (TT42) and then analyzed by FACS. The reactivity with each antibody is shown as +++, ++, +, ±, and −, in the order of decreasing reactivity. − means the absence of reactivity with the antibody. NT means that the analysis was not conducted.

Measurement of the expression levels of type 1 sugar chains (sialyl-Lewis a sugar chain, Lewis a sugar chain, Lewis b sugar chain) in various cell lines was conducted by fluorescent antibody staining with anti-sialyl-Lewis a sugar chain antibody, anti-Lewis a sugar chain antibody or anti-Lewis b sugar chain antibody, followed by analysis by FACS (FIG. 1, A).

Quantification of transcripts from the known β1,3-galactosyltransferase (β3Gal-T1, β3Gal-T2, β3Gal-T3, β3Gal-T4) genes in various human cell lines was conducted using the RT-PCR method [Proc. Natl. Acad. Sci. USA., 87, 2725 (1990), J. Biol. Chem., 269, 14730 (1994), Japanese Published Unexamined Patent Application No. 181759/94, J. Biol. Chem., 273, 26729 (1998)]. The amounts of transcripts from the respective β1, 3-galactosyltransferase genes in the respective cell lines are shown as values relative to the amount (=1000) of the β-actin transcript considered to be expressed at a similar degree in any cells (FIG. 1, B).

(1) Measurement of the Expression Levels of Type 1 Sugar Chains (Sialyl-Lewis a Sugar Chain, Lewis a Sugar Chain, Lewis b Sugar Chain) in Various Cell Lines The cell lines used were colon cancer cell lines (Colo205, Colo201, SW1116, LS180, HT29, WiDr, HCT-15, SW480, SW620), pancreatic cancer cell lines (Capan-1, Capan-2), stomach cancer cell lines (KATOIII, MKN45, MKN74), a lung cancer cell line (PC-1), neuroblastoma cell lines (SK-N-MC, SK-N-SH), lymphoma cell lines (Namalwa, Jurkat) and a prostate cancer cell line (PC-3).

Colo205, Colo201, LS180, HT29, WiDr, HCT-15, SW480, SW620, Capan-1, Capan-2, KATOIII, MKN45, MKN74, PC-1, SK-N-MC, SK-N-SH, Namalwa and PC-3 were obtained from American Type Culture Collection (ATCC). Further, SW1116 (available from ATCC) and Jurkat (available from RIKEN GENE BANK) were obtained from Dr. Takahashi, Aichi Cancer Center, JP.

The cells described above were cultured in a medium suitable for the respective cells, and then the cells were subjected to fluorescent antibody staining with anti-sialyl-Lewis a sugar chain antibody (19-9), anti-Lewis a sugar chain antibody (7LE) or anti-Lewis b sugar chain antibody (TT42) and analyzed by FACS.

The specific method is as follows:

About $1 \times 10^6$ cells were placed in a microtube (1.5 ml, produced by Eppendorf) and the cells were collected by centrifugation (550×g, 7 minutes).

The cells were washed with 0.9 ml of phosphate buffer solution containing 0.1% sodium azide (A-PBS: 8 g/l NaCl, 0.2 g/l KCl, 1.15 g/l $Na_2HPO_4$ (anhydride), 0.2 g/l $KH_2PO_4$, 0.1% sodium azide). After 20 µl of anti-sugar chain antibody previously diluted to about 10 µg/ml with A-PBS was added to the washed cells, the cells were suspended and reacted at 4° C. for 1 hour.

After the reaction, the cells were washed once with 0.9 ml of A-PBS and then suspended in 20 µl of a solution previously prepared by diluting anti-mouse IgM/IgG antibodies labeled with fluorescein isothiocyanate (FITC) (a product of Bio-Rad) 16-fold with A-PBS, followed by reaction at 4° C. for 30 minutes.

After the reaction, the cells were washed once with 0.9 ml of A-PBS, then suspended in 0.6 ml of A-PBS and analyzed by a fluorescence activated cell sorter (EPICS Elite Flow Cytometer manufactured by COULTER). In a control experiment, the same analysis was conducted by use of A-PBS in place of the anti-sugar chain antibody.

The results are shown in FIG. 1, A. It was confirmed that in the colon cancer cell lines, Colo205, Colo201 and SW1116 and pancreatic cancer cell line, Capan-2, type 1 sugar chains are expressed in larger amounts.

(2) Quantification of Transcripts From Known β1,3-galactosyltransferase (β3Gal-T1, β3Gal-T2, β3Gal-T3, β3Gal-T4) Genes in Various Human Cell Lines (a) Preparation of Single-Stranded cDNA Derived from Various Cell Lines From the cell lines described in item (1) above, total RNAs were extracted by the acid guanidium thiocyanate phenol-chloroform method [Anal. Biochem., 162, 156–159].

Deoxyribonuclease I (a product of Life Technologies Ltd.) (5 U/ml) was added to 6 µg each of total RNAs and reacted at room temperature for 5 minutes. After the reaction, the mixture was heated at 65° C. for 15 minutes to inactivate the enzyme.

From each of the resulting total RNAs, cDNA was synthesized using an oligo(dT)primer by SUPERSCRIPT™ Preamplification System for First Strand cDNA System (a product of Life Technologies Ltd.). The reaction was conducted in 20 µl solution, and the solution after the reaction was diluted 50-fold with water and stored at −80° C. until use.

(b) Preparation of Standards and Internal Controls

As the standards used for preparation of a calibration curve, linear DNAs were prepared by integrating cDNAs of human β3Gal-T1, human β3Gal-T2, human β3Gal-T3 and human β33Gal-T4 into pUC119 or pBluescript SK(−) and cleaving the resulting plasmids (pUC119-3GT1, pBS-3GT2, pBS-3GT3, pBS-3GT4) with suitable restriction enzymes to take the cDNA inserts.

pUC119-3GT1 is identical with plasmid pUC119-WM1 (FERM BP-4011) described in Japanese Published Unexamined Patent Application No. 181759/94. The cDNAs of human β3Gal-T2, human β3Gal-T3 and human β3Gal-T4 were obtained in the following manner.

A fragment of each cDNA was obtained by PCR using primers specific to the sequence of each cDNA.

By colony hybridization or plaque hybridization using each cDNA fragment thus obtained as a probe, each cDNA was obtained. The nucleotide sequences of human β3Gal-T2, human β3Gal-T3 and human β3Gal-T4 were determined by DNA sequencer model 4000L (a product of LI-COR Ltd.) or DNA sequencer 377 (a product of Perkin Elmer) using a reaction kit for each sequencer and it was confirmed that each cDNA codes for human β3Gal-T2, human β3Gal-T3 and human β3Gal-T4, respectively. Each cDNA could also be obtained by PCR on the basis of its known sequence.

As the standard for quantification of the β-actin transcript, a linear DNA was prepared by cleaving pUC119-ACT with restriction enzymes (HindIII and Asp718) to take the cDNA insert [J. Biol. Chem., 269, 14730 (1994), Japanese Published Unexamined Patent Application No. 181759/94].

As the internal controls, linear DNAs were prepared by cleaving plasmids prepared below (pUC119-3GT1d, pBS-3GT2d, pBS-3GT3d, pBS-3GT4d) with suitable restriction enzymes to take the cDNA inserts.

By deleting a 212-bp sequence between BanII-EcoRV in human β3Gal-T1, cDNA in pUC119-3GT1, pUC119-3GT1d was prepared.

By deleting a 258-bp sequence between AflII-BstEII in human β3Gal-T2 cDNA in pBS-3GT2, pBS-3GT2d was prepared.

By deleting a 183-bp sequence between StyI—StyI in human β3Gal-T3 cDNA in pBS-3GT3, pBS-3GT3d was prepared.

By deleting a 253-bp sequence between AccIII-StyI in human β3Gal-T4 cDNA in pBS-3GT4, pBS-3GT4d was prepared.

As the internal control for quantification of the β-actin transcript, a linear DNA was prepared by cleaving pUC119-ACTd with restriction enzymes (HindIII and Asp718) to take the cDNA insert [J. Biol. Chem., 269, 14730 (1994), Japanese Published Unexamined Patent Application No. 181759/94].

(c) Quantification of Transcripts by RT-PCR

Reaction solution [10 mmol/l Tris-HCl (pH8.3), 50 mmol/l KCl, 1.5 mmol/l $MgCl_2$, 0.2 mmol/l dNTP, 0.001% (w/v) gelatin, 0.2 µmol/l gene-specific primers] (50 µl) containing 10 µl of each tissue-derived cDNA and 10 µl (10 fg) of each internal control plasmid described above was subjected to PCR with DNA polymerase AmpliTaq Gold™ (a product of Perkin Elmer).

The nucleotide sequence of each gene-specific primer is shown in Table 1. Further, the nucleotide sequences of β3Gal-T1 gene-specific primers are represented by SEQ ID NOS: 4 and 5, the nucleotide sequences of β3Gal-T2 gene-specific primers by SEQ ID NOS: 6 and 7, the nucleotide sequences of β3Gal-T3 gene-specific primers by SEQ ID NOS: 8 and 9, the nucleotide sequences of β3Gal-T4 gene-specific primers by SEQ ID NOS: 10 and 11, and the nucleotide sequences of the β-actin specific primers by SEQ ID NOS: 12 and 13. The nucleotide sequences of β3Gal-T5 gene-specific primers are represented by SEQ ID Nos: 20 and 21.

TABLE 1

Conditions and Primers Used in Quantitative PCR

| Target gene | *Primer set | Size of PCR product (bp) Target | Competitor | Annealing temp. (° C.) |
|---|---|---|---|---|
| β3Gal-T1 | F:5'-TTCAGCCACCTAACAGTTGCCAGG-3'<br>R:5'-ATACCTTCTTCGTGGCTTGGTGGAG-3' | 495 | 283 | 60 |
| β3Gal-T2 | F:5'-TAGAAGCTAGAAGAGCTATTCGGC-3'<br>R:5'-ACTCGCCAGTGATTGAACACAAAC-3' | 616 | 358 | 60 |
| β3Gal-T3 | F:5'-CCCAATGCCAAGTACGTAATGAAG-3'<br>R:5'-TGTGGTGTTCCTTAGCATGACCTG-3' | 474 | 291 | 60 |
| β3Gal-T4 | F:5'-TTGATCCCCAACCAGGAAGCTTGC-3'<br>R:5'-TGAGGCCACTGCTCCTCTGATACG-3' | 590 | 337 | 68 |
| β3Gal-T5 | F:5'-ACCACCAGCAGTGCAGCGGAAAC-3'<br>R:5'-GCCACGATCCTCCTGAAGAGGCA-3' | 554 | 410 | 65 |
| β-Actin | F:5'-GATATCGCCGCGCTCGTCGTCGAC-3'<br>R:5'-CAGGAAGGAAGGCTGGAAGAGTGC-3' | 789 | 639 | 60 |

*F: forward primer, R: reverse primer

By the primer sets shown above, DNA fragments of sizes shown in target in Table 1 can be amplified from the respective gene transcripts and the respective standards. By the primer sets shown above, DNA fragments of sizes shown in competitor in Table 1 can be amplified from the respective internal controls.

After heating at 95° C. for 11 minutes, PCR was conducted using 42-cycle reaction for the β1,3-galactosyltransferase gene group and 24-cycle reaction for the β-actin, each cycle consisting of reaction at 95° C. for 1 minute, at an annealing temperature shown in Table 1 suitable for each gene for 1 minute, and at 72° C. for 2 minutes.

Each solution (10 μl) after PCR was electrophoresed on 1% agarose gel, stained by ethidium bromide and photographed. By scanning each photograph by an NIH image system, the density of staining of each amplified fragment was determined as the amplification amount.

PCR was conducted similarly using 1.25 fg, 2.5 fg, 5 fg, 10 fg, 20 fg and 40 fg of standard plasmid prepared above in place of the cell-derived cDNA, to determine the amount of the amplified fragment, and by plotting the amount of the amplified fragment vs. the amount of the cDNA, a calibration curve was prepared.

From this calibration curve and the amounts of the fragments amplified from cDNAs derived from various cells, the amounts of the cDNAs in various cells were calculated and assumed to be the amounts of mRNAs transcribed in the various cells, that is, the expression levels of the genes. Because the β-actin gene is considered to be a gene expressed universally in various cells, its expression level is considered similar in any cells. Accordingly, a difference in the expression level of the β3-actin gene among the respective cells is considered attributable to the difference of efficiency of cDNA synthesis reaction, and thus when the expression levels of the β1,3-galactosyltransferase genes were compared, the expression level of the β-actin gene was also taken into consideration.

The amounts of the respective β1,3-galactosyltransferase gene transcripts in various cell lines are shown as values relative to the amount (=1000) of the β-actin transcript (FIG. 1, B).

β3Gal-T1, β3Gal-T2 and β3Gal-T3 have the activity of synthesizing Galβ1-3GlcNAc structure, but they were hardly expressed in the colon cancer cell lines (Colo205, Colo201, SW1116) and pancreatic cancer cell line (Capan-2) expressing large amounts of type 1 sugar chains. On the other hand, β3Gal-T4 was expressed in the colon cancer cell lines (Colo205, Colo201, SW1116) and pancreatic cancer cell line (Capan-2), but it has been revealed that this enzyme has no activity of synthesizing Galβ1-3GlcNAc structure.

From these results, it was revealed that β1,3-galactosyltransferase involved in the synthesis of type 1 sugar chains in these cell lines is a novel enzyme.

Example 2

Cloning of a Gene (cDNA) Coding for the Novel Polypeptide Having β1,3-Galactosyltransferase Activity, Participating in the Synthesis of Type 1 Sugar Chains such as Sialyl-Lewis a Sugar Chain in Cancer Cells in the Digestive System, such as Colon Cancer Cells or Pancreatic Cancer Cells (1) Acquisition of mRNA from Human Colon Cancer Cell Line Colo205

About 30 μg of mRNA was obtained from human colon cancer cell line Colo205 by use of a mRNA extraction kit, Oligotex™-dT30<super> (a product of Roche).

The reagents and method employed are those described in instructions attached to the kit.

(2) Preparation of a cDNA Library Derived from Human Colon Cancer Cell Line Colo205

Eight micrograms of the mRNA derived from human colon cancer cell line Colo205, obtained in item (1) above, and a kit from Gibco BRL (SUPERSCRIPT Choice System for cDNA Synthesis) were used to synthesize double-stranded cDNA by use of oligo-dT as a primer.

Sfi I linkers were added to both termini of the double-stranded cDNA in the following manner.

[Addition of Sfi I Linkers]

The single-stranded DNA represented by SEQ ID NO:14 and the single-stranded DNA represented by SEQ ID NO:15 were synthesized by 380A•DNA synthesizer (a product of Applied Biosystems).

Each of the synthesized single-stranded DNAs (50 µg) was separately dissolved in 50 µl of a buffer containing 50 mmol/l Tris-HCl buffer (pH 7.5), 10 mmol/l MgCl$_2$, 5 mmol dithiothreitol (abbreviated hereinafter to DTT), 0.1 mmol/l EDTA and 1 mmol/l ATP (this buffer is referred hereinafter to T4 kinase buffer), followed by addition of 30 U of T4 polynucleotide kinase (a product of Takara Shuzo Co., Ltd.) to allow phosphorylation reaction at 37° C. for 16 hours whereby 11-bp and 8-bp linkers were obtained, respectively.

Four micrograms of the 11-bp linker, 2.9 µg of the 8-bp linker and the double-stranded cDNAs synthesized above were dissolved in 45 µl of T4 ligase buffer, and 1050 U of T4 DNA ligase was added thereto followed by reaction at 16° C. for 16 hours, and the Sfi I linkers were added to each of the double-stranded cDNAs.

The resulting reaction mixture was subjected to agarose gel electrophoresis and about 1.5-kb or more DNA fragment was recovered.

Twenty-four micrograms of expression cloning vector pAMo (J. Biol. Chem., 268, 22782 (1993), also called pAMo PRC3Sc (Japanese Published Unexamined Patent Application No. 336963/93)] was dissolved directly in 590 µl of a buffer containing 10 mmol/l Tris-HCl (pH 7.5), 6 mmol/l MgCl$_2$, 50 mmol/l NaCl and 6 mmol/l 2-mercaptoethanol (this buffer is referred to hereinafter as Y-50 buffer), and 80 U of restriction enzyme Sfi I (a product of Takara Shuzo Co., Ltd.; all restriction enzymes used hereinafter are products of Takara Shuzo Co., Ltd. unless otherwise specified) was added to allow digestion reaction at 37° C. for 16 hours.

Forty units of BamHI was added to the reaction mixture, followed by digestion reaction at 37° C. for 2 hours. The reaction mixture was subjected to agarose gel electrophoresis, and about 8.8-kb DNA fragments were recovered.

The DNAs prepared above (each derived from 8 µg of mRNA) having Sfi I linkers added thereto were separately dissolved in 250 µl of T4 ligase buffer, and to each mixture were added 2 µg of about 8.8-kb DNA fragments obtained above and 2000 U of T4 DNA ligase, followed by ligation reaction at 16° C. for 16 hours.

After the reaction, 5 µg of transfer RNA (tRNA) was added to each reaction mixture, and the sample was precipitated with ethanol and the obtained precipitate was dissolved in 20 µl of a buffer containing 10 mmol/l Tris-HCl buffer (pH 8.0) and 1 mmol/l EDTA (sodium ethylenediamine tetraacetate) (this buffer is referred to hereinafter as TE buffer).

The reaction solution was used to transform *E. coli* LE392 (Molecular Cloning, 2nd edition) by the electroporation method [Nucleic Acids Res., 16, 6127 (1988)], and about 1,000,000 ampicillin-resistant transformants were obtained, to prepare a cDNA library.

Using said cDNA library (*E. coli*) and a plasmid maxi kit (Product No. 41031), that is, a plasmid preparation kit produced byQiagen, a plasmid containing the cDNAwas prepared.

(3) Acquisition of a cDNA Fragment for the Novel β1,3-galactosyltransferase by Use of Degenerate Primers By comparing the amino acid sequences of known four β1,3-galactosyltransferases (β3Gal-T1, β3Gal-T2, β3Gal-T3, β3Gal-T4), three or more sites each having a well-conserved amino acid sequence in the known four β1,3-galactosyltransferases were found. Said three sites are called motifs 1, 2 and 3, respectively, from the N-terminus. The amino acid sequence of each motif in the four β1,3-galactosyltransferases and the position of the first amino acid of each motif from the N-terminus are shown in Table 2.

TABLE 2

Amino Acid Sequence Motifs Conserved in β3Gal-T Family

| | Motif 1 | Motif 2 | Motif 3 |
|---|---|---|---|
| β3Gal-T1 | A$^{99}$IRETWG | Y$^{172}$VMKTDSD | E$^{264}$DVYVGLC |
| | (SEQ. ID NO:26) | (SEQ. ID NO:27) | (SEQ. ID NO:28) |
| β3Gal-T2 | A$^{169}$IRQTWG | Y$^{247}$VMKTDSD | E$^{340}$DVYVGIC |
| | (SEQ. ID NO:29) | (SEQ. ID NO:30) | (SEQ. ID NO:31) |
| β3Gal-T3 | A$^{96}$IRVTWG | Y$^{175}$VMKTDTD | E$^{266}$DVYVGIC |
| | (SEQ. ID NO:32) | (SEQ. ID NO:33) | (SEQ. ID NO:34) |
| β3Gal-T4 | A$^{89}$IRASWG | Y$^{170}$VLKTDDD | E$^{290}$DFYVGVS |
| | (SEQ. ID NO:35) | (SEQ. ID NO:36) | (SEQ. ID NO:37) |

According to known methods [Carl W. Dieffenbach, Gabriela S. Dveksler, "PCR Primer: A Laboratory Manual", Cold Spring Harbor Lab. (1995), The Protocol Series "cDNA Cloning" edited by Jyunichiro Inoue & Kentaro Senba and published by Yodosha (1996), Science, 241, 42 (1988)], degenerate primers having a nucleotide sequence corresponding to the amino acid sequence of each motif were designed. As the forward primer, two synthetic DNAs (whose sequences are represented by SEQ ID NOS: 16 and 17, respectively) corresponding to motifs 1 and 2 were synthesized. As the reverse primer, two synthetic DNAs (whose sequences are represented by SEQ ID NOS: 18 and 19, respectively) corresponding to motifs 2 and 3 were synthesized.

PCR was conducted using the DNAs represented by SEQ ID NOS: 16 and 18 as the primers and the cDNA library (plasmid) prepared in item (2) above as the template, and the amplified DNA was blunt-ended with a DNA polymerase Klenow fragment and then subcloned into EcoRV site of pBluescript SK (−) (a product of Stratagene). In addition, PCR was conducted using the DNAs represented by SEQ ID NOS: 17 and 19 as the primers and the cDNA library (plasmid) prepared in item (2) above as the template, and the amplified DNA was blunt-ended with a DNA polymerase Klenow fragment and then subcloned into EcoRV site of pBluescript SK (−) (a product of Stratagene).

One unit of DNA polymerase AmliTaq Gold™ (a product of Perkin Elmer) was added to 50 µl of reaction solution [10 mmol/l Tris-HCl (pH 8.3), 50 mmol/l KCl, 1.5 mmol/l MgCl$_2$, 0.2 mmol/l dNTP, 0.001% (w/v) gelatin, 0.2 µmol/l primers] containing the cDNA library (100 ng plasmid) prepared in item (2) above, and the mixture was subjected to PCR.

After heating at 95° C. for 11 minutes, PCR was conducted using 45-cycle reaction, each cycle consisting of reaction at 95° C. for 30 seconds, at 35° C. for 1 minute and at 72° C. for 2 minutes.

The nucleotide sequence of the subcloned, PCR-amplified fragment was determined using a kit from EPICENTRE TECHNOLOGIES (SequiTherm EXCEL II Long-Read DNA Sequencing kit-ALF: Catalog No. SE8301A) and an ALF DNA sequencer (a product of Amersham Pharmacia Biotech).

As a result of PCR using the DNAs represented by SEQ ID NOS: 16 and 18 as the primers, one DNA fragment coding for an amino acid sequence that is homologous to, but not completely consistent with, the amino acid sequence of known β1,3-galactosyltransferase was obtained.

The sequence of said DNA fragment excluding the primer regions agreed with the nucleotide sequence of 643 to 851 in the DNA represented by SEQ ID NO: 2.

Further, one DNA fragment coding for an amino acid sequence that is homologous to, but not completely consistent with, the amino acid sequence of known β1,3-galactosyltransferase was obtained by PCR using the DNAs represented by SEQ ID NOS: 17 and 19 as the primers.

The sequence of said DNA fragment excluding the primer regions agreed with the nucleotide sequence of 876 to 1124 in the DNA represented by SEQ ID NO: 2.

(4) Acquisition of cDNA of the Novel β1,3-galactosyltransferase

The two PCR-amplified fragments obtained in item (3) were mixed and labeled with $^{32}P$ by a multi-prime DNA label system (a product of Amersham) to prepare a probe.

$5 \times 10^5$ clones in the cDNA library prepared in item (2) above was subjected to colony hybridization with said probe.

In this hybridization, the filter was washed twice at 65° C. for 10 minutes by shaking it in a buffer consisting of 2-fold conc. SSPE (pH 7.4) [1-fold conc. SSPE is composed of 180 mmol/l sodium chloride, 10 mmol/l sodium dihydrogen phosphate, 1 mmol/l ethylenediaminetetraacetic acid (EDTA)] and 0.1% SDS, then washed once at 65° C. for 15 minutes by shaking it in a buffer consisting of 1-fold conc. SSPE and 0.1% SDS, and washed twice at 65° C. for 10 minutes by shaking it in a buffer consisting of 0.2×SSPE and 0.1% SDS.

As a result of the colony hybridization, two independent plasmids hybridizing therewith were obtained.

(5) Determination of the Nucleotide Sequence of the cDNA Inserted in Plasmid pAMo-3GT5

The entire nucleotide sequence of the cDNA contained in pAMo-3GT5 that is one of the plasmids obtained in item (4) above was determined in the following method.

By using primers specific to a sequence in the pAMo vector, 5'- and 3'-terminal sequences of said cDNA were determined.

Synthetic DNAs specific to the sequences thus determined were prepared, and by using the DNAs as primers, the nucleotide sequence of a further region in said cDNA was determined.

This operation was repeatedly carried out, whereby the entire nucleotide sequence of said cDNA was determined.

For nucleotide sequencing, DNA sequencer model 4000L (a product of LI-COR Ltd.) and a reaction kit (Sequitherm EXCEL II™ Long-Read™ DNA-sequencing kit-Lc: a product of Air Brown) or DNA sequencer 377 (a product of Perkin Elmer) and a reaction kit (ABI Prism™ BigDye™ Terminator Cycle Sequencing Ready Reaction kit: a product of Applied Biosystems) were used.

The entire nucleotide sequence (2775 bp) of the cDNA contained in pAMo-3GT5 is represented by SEQ ID NO: 2.

Said cDNA coded for a polypeptide consisting of 310 amino acids having a structure characteristic of glycosyltransferase.

Said polypeptide has 28 to 37% homology at amino acid level to the four human β1,3-galactosyltransferases (β3Gal-T1, β3Gal-T2, β3Gal-T3, β3Gal-T4) cloned so far, so said polypeptide was considered to be a novel β1,3-galactosyltransferase. Homology analysis of said amino acid sequence was conducted using the sequence analysis software GENE-TYX-MAC 10.1 (a product of Software Kaihatsu Co., Ltd.).

Homology (%) was calculated by dividing the number of consistent amino acid residues by the number of amino acid residues of β3Gal-T5.

The amino acid sequence of said polypeptide is represented by SEQ ID NO: 1.

Said polypeptide was considered to consist of a cytoplasm region consisting of N-terminal seven amino acids, a highly hydrophobic membrane-binding region consisting of 19 amino acids, a stem region consisting of at least 4 amino acids, and a large C-terminal region containing a catalytic domain. On the basis of comparison of its homology in amino acid sequence to other β1,3-galactosyltransferases and information on the stem region and catalytic domain of other β1,3-galactosyltransferases [Japanese Published Unexamined Patent Application No. 181759/94], it is estimated that the stem region consists of at least 4 amino acids. Accordingly, a partial polypeptide containing the amino acid sequence of 31 to 310 is considered to contain the catalytic domain.

Hereinafter, said cDNA is referred to as human β3Gal-T5 cDNA, and the polypeptide encoded by said cDNA is referred to as human β3Gal-T5.

Figure 2:
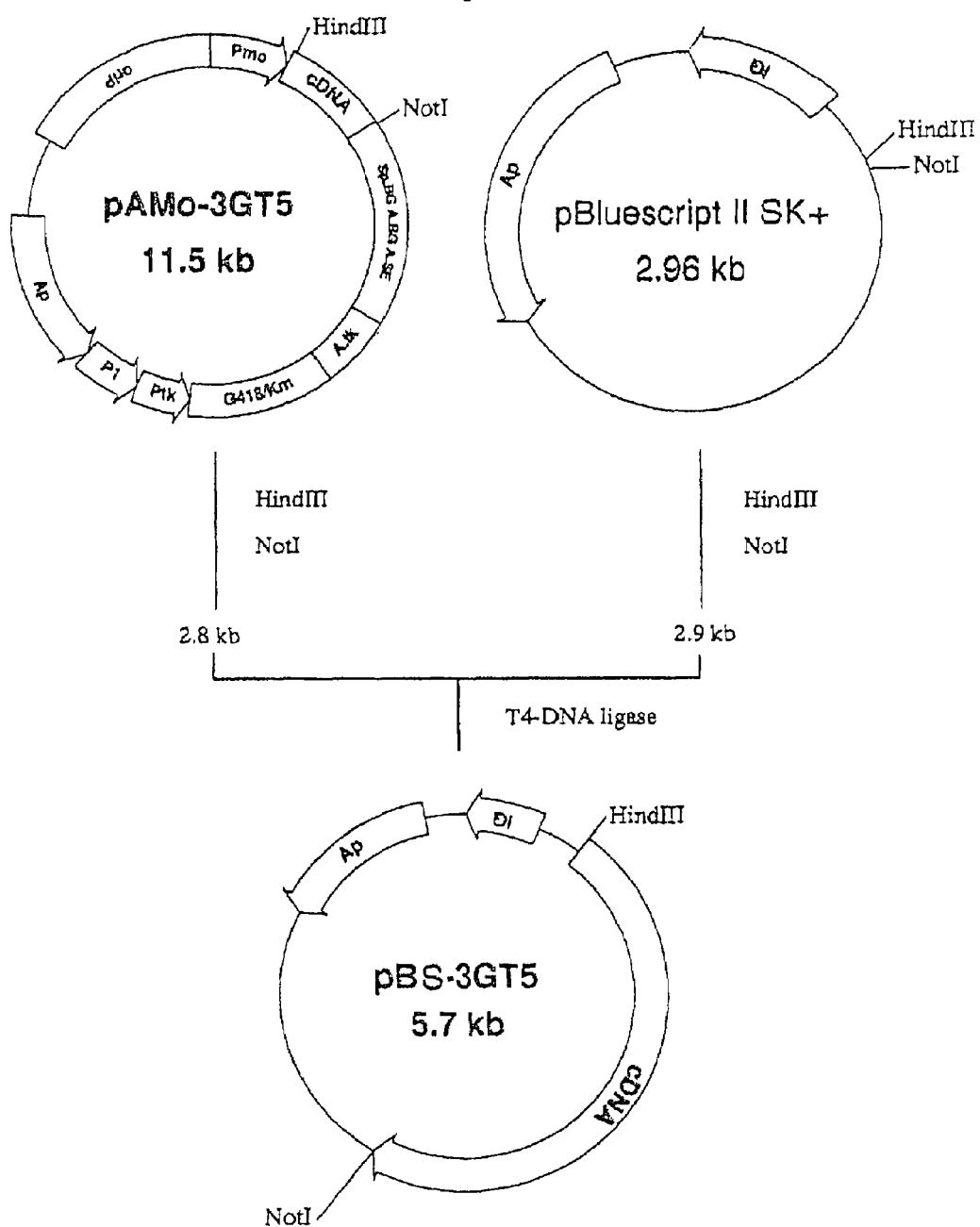
FIG. 2 shows the process of construction of plasmid pBS-3GT5.

Human β3Gal-T5 cDNA was cleaved off by cleaving pAMo-3GT5 with HindIII and NotI and inserted between HindIII and NotI sites in pBluescript II SK(+), whereby pBS-3GT5 was constructed (FIG. 2).

*Escherichia coli* MM294/pBS-3GT5 harboring pBS-3GT5 was deposited as FERMBP-6645 on Feb. 10, 1999 with the National Institute of Bioscience and Human-Technology, Agency of Industrial Science and Technology (1-3, Higashi 1-chome, Tsukuba-shi, Ibaraki, 305–8566, Japan).

(6) Synthesis of Type 1 Sugar Chains in Human Cultured Cells to which Human β3Gal-T5 Expression Plasmid was Introduced The control plasmid (pAMo) and human β3Gal-T5 expression plasmid (pAMo-3GT5) were dissolved at a concentration of 1 μg/μl, respectively, in TE buffer and introduced by the electroporation method [Cytotechnology, 3, 133 (1990)] into Namalwa cells to give transformed cells.

After introduction of 4 μg of plasmid/$1.6 \times 10^6$ cells, the cells were suspended in 8 ml of RPMI1640 medium containing 10% fetal bovine serum [RPMI1640 medium (Nissui Pharmaceuticals, Co.) containing 1/40 volume of 7.5% NaHCO$_3$, 3% of 200 mmol/l L-glutamine solution (GIBCO) and 0.5% penicillin-streptomycin solution (5000 units/ml penicillin and 5000 μg/ml streptomycin, a product of GIBCO)] and cultured at 37° C. for 24 hours in a CO$_2$ incubator.

After culturing, G418 (a product of GIBCO) was added thereto at a concentration of 0.8 mg/ml, and culturing was further continued for 14 days, whereby a stable transformant was obtained. The transformant was subcultured in RPM1640 containing 0.8 mg/ml G418.

The transformed cells were subjected to indirect fluorescent antibody staining with anti-sialyl-Lewis c sugar chain antibody (DU-PAN-2, a product of Kyowa Medex).

Figure 3:
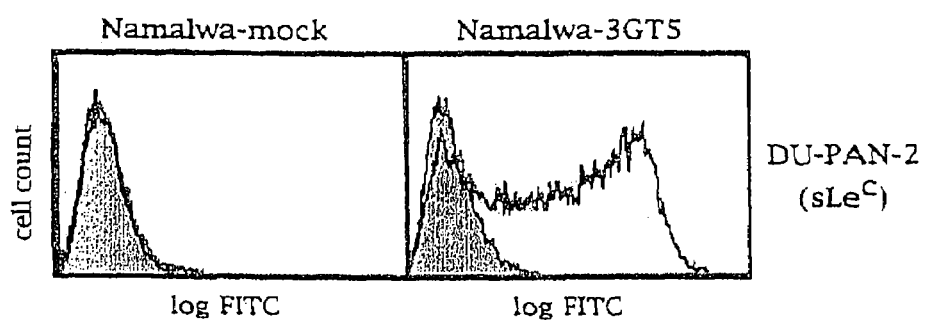
FIG. 3, A shows the results of indirect fluorescent antibody staining with anti-sialyl-Lewis c sugar chain antibody (DU-PAN-2) and subsequent FACS analysis of Namalwa cells (Namalwa-mock) having the control plasmid (pAMo) introduced therein, or Namalwa cells (Namalwa-3GT5) having human β3Gal-T5 expression plasmid (pAMo-3GT5) introduced therein. The shaded histogram shows the result of analysis using A-PBS in place of DU-PAN-2.
Figure 3:
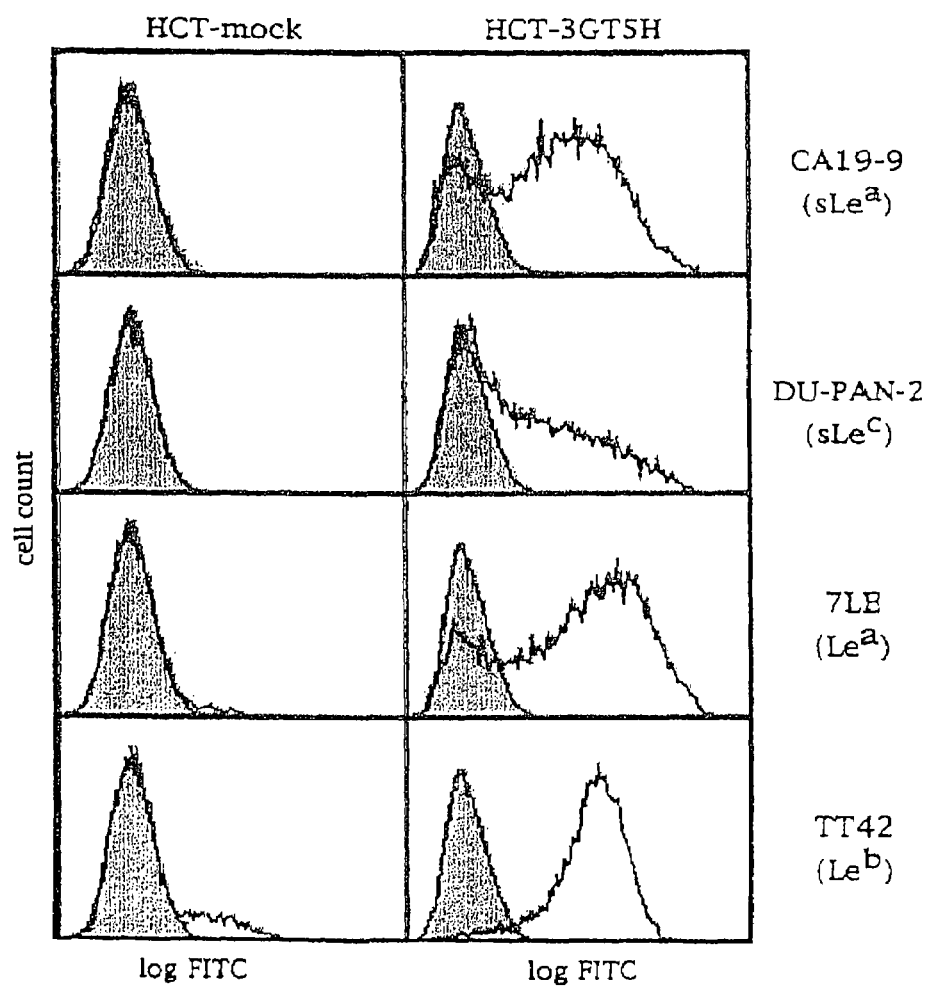

The indirect fluorescent antibody staining was conducted according to the method described in item (1) in Example 1. As a result, the cells having pAMo-3GT5 introduced therein showed significantly increased reactivity with the anti-sialyl-Lewis c sugar chain antibody (DU-PAN-2) compared with the cells having pAMo introduced therein(FIG. 3, A).

Further, the control plasmid (pAMo) and human β3Gal-T5 expression plasmid (pAMo-3GT5) were introduced in the same manner as above into the colon cancer cell line HCT-15 expressing no type 1 sugar chain, to give stable transformed cells. From the stable transformed cells, single clones (HCT-3GT5L and HCT-3GT5H) were obtained by the limiting dilution method. The amount of β3Gal-T5 transcript in HCT-3GT5L was lower than the amount of β3Gal-T5 transcript in HCT-3GT5H (see Example 4 and Table 3). Said single clones were subcultured in PRMI1640 containing 0.8 mg/ml G418.

The single clone (HCT-3GT5H) thus obtained was subjected to indirect fluorescent antibody staining with anti-sialyl-Lewis a sugar chain antibody (19-9), anti-sialyl-Lewis c sugar chain antibody (DU-PAN-2, a product of Kyowa Medex), anti-Lewis a sugar chain antibody (7LE) or anti-Lewis b sugar chain antibody (TT42).

The indirect fluorescent antibody staining was conducted according to the method described in item (1) in Example 1. As a result, it was revealed that the cells having pAMo-3GT5 introduced therein showed significantly higher reactivity with all the 4 antibodies than that of the cells having pAMo introduced therein (FIG. 3, B).

These results indicated that β3Gal-T5 is capable of synthesizing type 1 sugar chains (sialyl-Lewis a sugar chain, sialyl-Lewis c sugar chain, Lewis a sugar chain and Lewis b sugar chain) in the transformed cells.

Further, this result means that by expressing β3Gal-T5 in cells, sugar chains containing type 1 sugar chains (sialyl-Lewis a sugar chain, sialyl-Lewis c sugar chain, Lewis a sugar chain and Lewis b sugar chain) as well as complex carbohydrates containing said sugar chains can be de novo synthesized.

From the foregoing, it is evident that by secretory production of useful glycoproteins in host cells expressing β3Gal-T5, type 1 sugar chains (sialyl-Lewis a sugar chain, sialyl-Lewis c sugar chain, Lewis a sugar chain and Lewis b sugar chain, etc.) can be added to the glycoproteins to be produced and secreted.

(7) Quantification of Human β3Gal-T5 Gene Transcripts in Various Human Cell Lines Human β3Gal-T5 gene transcripts were quantified according to the method in item (2) in Example 1.

Each of the single-stranded cDNAs derived from various cell lines, prepared in item (1) in Example 1, was used as the template.

As the standard used for preparation of a calibration curve, linear DNA was prepared by cleaving the plasmid (pBS-3GT5) having human β3Gal-T5 cDNA integrated in pBluescript II SK(+) constructed in item (5), with suitable restriction enzymes to take the cDNA insert.

As the internal control, linear DNA was prepared by cleaving a plasmid (pBS-3GT5d) prepared below with suitable restriction enzymes to take the cDNA insert.

By deleting a 144-bp sequence between Eco81I-XcmI in human β3Gal-T5 cDNA in pBS-3GT5, pBS-3GT5d was prepared.

Quantification of the transcripts by RT-PCR was conducted in the same manner as in item (2) in Example 1 by use of β3Gal-T5 specific primers. The nucleotide sequences of β3Gal-T5 specific primers are shown in Table 1 and SEQ ID NOS: 20 and 21.

By the β3Gal-T5 specific primers, the DNA fragment (554 bp) shown in target in Table 1 can be amplified from 3Gal-T5 gene transcripts and the standard. By the above primers, the DNA fragment (410 bp) shown in competitor in Table 1 can be amplified from the internal control.

After heating at 95° C. for 11 minutes, PCR was carried out using 42-cycle reaction, each cycle consisting of reaction at 95° C. for 1 minute, at 65° C. for 1 minute and at 72° C. for 2 minutes.

Figure 4:
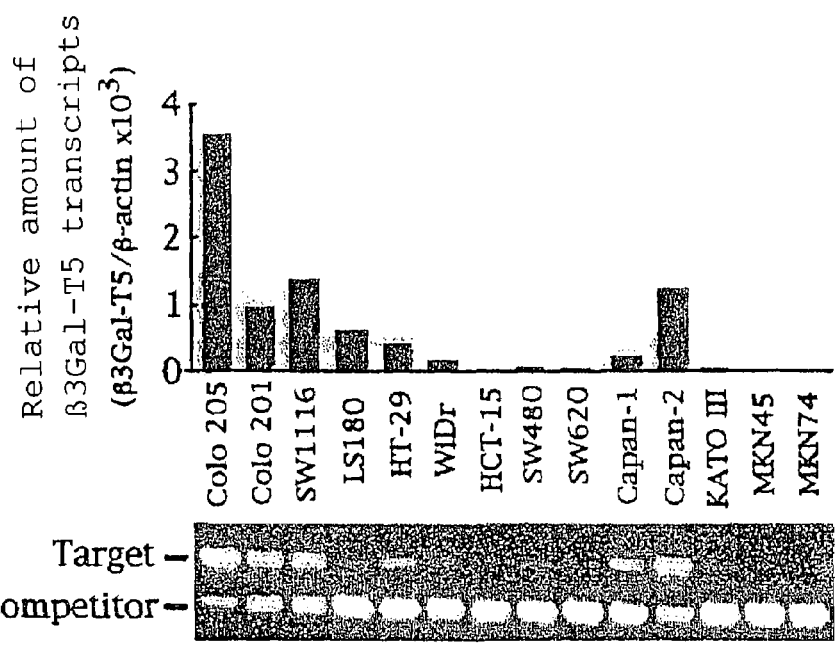
FIG. 4, A shows the results of quantification of human β3Gal-T5 transcripts in various human cancer cell lines by the quantitative PCR method. The amounts of the human β3Gal-T5 transcripts in various cell lines are expressed as values relative to the amount (=1000) of the β-actin transcript considered to be expressed at a similar degree in any cells.
Figure 4:
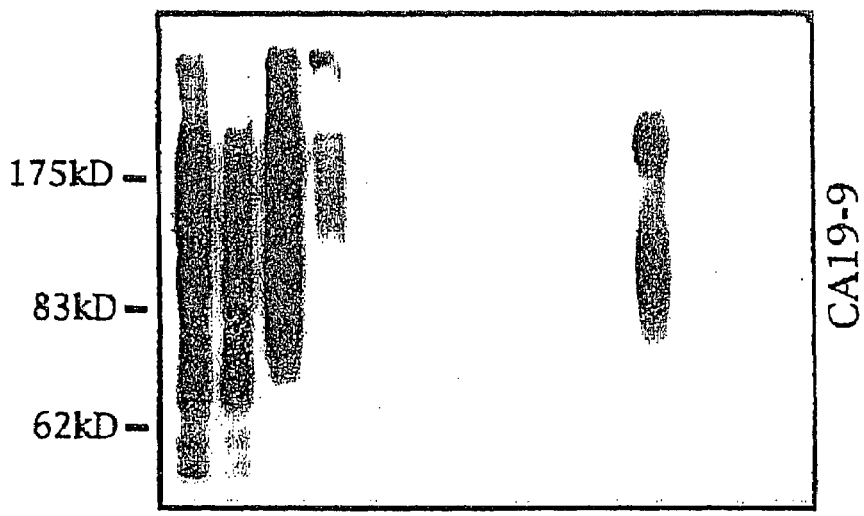

The amounts of the β3Gal-T5 gene transcripts in various cell lines are shown as values relative to the amount (=1000) of the β-actin transcript (FIG. 4, A).

It was revealed that the β3Gal-T5 transcript is expressed in the colon cancer cell lines (Colo205, Colo201, SW1116) and pancreatic cancer cell line (Capan-2) expressing large amounts of type 1 sugar chains. Further, expression of the β3Gal-T5 transcript was well correlated with expression of type 1 sugar chains (see FIG. 1).

Taking the above results in (5) and (6) into consideration, it is concluded that β3Gal-T5 is a novel β1,3-galactosyltransferase involved in the synthesis of type 1 sugar chains such as sialyl-Lewis a sugar chain and sialyl-Lewis c sugar chain in cancer cells in the digestive system, such as colon cancer cells or pancreatic cancer cells.

(8) Expression of CA19-9 Antigen-Containing Proteins in Various Human Cell Lines Expression of sialyl-Lewis a sugar chain-containing proteins in colon cancer cell lines (Colo205, Colo201, SW1116, LS180, HT29, WiDr, HCT-15, SW480, SW620), pancreatic cancer cell lines (Capan-1, Capan-2) and stomach cancer cell lines (KATOIII, MKN45, MKN74) was examined by Western blotting analysis using anti-sialyl-Lewis a antibody (19-9).

19-9 has been utilized to detect cancer-related sugar chains in colon cancers and pancreatic cancers, and the sialyl-Lewis a sugar chain antigen detected by 19-9 is called CA19-9 antigen.

The respective cells ($1 \times 10^7$ cells) were suspended in a solution [20 mmol/l HEPES (pH 7.2), 2% Triton X-100] and sonicated in a short time to prepare a cell lysate.

The protein concentration in said cell lysate was determined using a micro-BCA protein assay reagent kit (a product of PIERCE), and 10 μg of protein was subjected to SDS-polyacrylamide gel electrophoresis (SDS-PAGE).

After the electrophoresis, the protein on the gel was transferred by Transblot SD cell (a product of Bio-Rad) onto Immobilon PVDF membrane (a product of Millipore).

The membrane was blocked by treatment overnight with a blocking solution (PBS containing 5% skim milk) at 4° C.

After the blocking, said membrane was treated at room temperature for 2 hours with 10 μg/ml anti-sialyl-Lewis a antibody (19-9) diluted with the blocking solution.

After this treatment, said membrane was treated with ECL Western blotting detection reagent (a product of Amersham), to detect the proteins to which 19-9 was bound. The method employed was that described in instructions attached to the kit.

The results are shown in FIG. 4, B.

Expression of CA19-9-containing glycoproteins agreed well with expression of β3Gal-T5 transcript (see FIG. 4, A) measured in item (7) above. On the other hand, expression of other GlcNAc β11,3-galactosyltransferase (β3Gal-T1, β3Gal-T2, β1,3Gal-T3) transcripts was not correlated with expression of CA19-9-containing glycoproteins. Further, other GlcNAc β1,3-galactosyltransferases (β1,3Gal-T1, β3Gal-T2, β3Gal-T3) were not expressed in Colo205 or Colo201 highly expressing CA19-9-containing glycoproteins (see FIG. 1).

These results indicate that β3Gal-T5 is a 11,3-galactosyltransferase involved in the synthesis of cancer-related antigen CA19-9 in colon cancers, pancreatic cancers, etc., and also that β3Gal-T5 can use glycoproteins as substrates.

Example 3

In Vitro Activity of Human β3Gal-T5

The in vitro activity of human β3Gal-T5 encoded by human β3Gal-T5 cDNA obtained in Example 2 was examined in the following manner.

For comparison with the activities of other known β1,3-galactosyltransferases, expression plasmids (pAMo-3GT1, pAMo-3GT2, pAMo-3GT3 and pAMo-3GT4) having the cDNAs of human β3Gal-T1, human β3Gal-T2, human β3Gal-T3 and human β3Gal-T4 integrated therein, respectively, were constructed.

pAMo-3GT1 is identical with plasmid pAMoPRWM1 used for constructing plasmid pUC119-WM1 (FERM BP-4011) described in Japanese Published Unexamined Patent Application No. 181759/94.

The control plasmid (pAMo) or each of the five β1,3-galactosyltransferase expression plasmids (pAMo-3GT1, pAMo-3GT2, pAMo-3GT3, pAMo-3GT4 and pAMo-3GT5) was introduced in the same manner as in Example 3 into Namalwa cells to give the respective transformed cells.

In the same manner as in (2) in Example 1, total RNA was extracted from the transformed cells, and the amounts of transcripts by the five 1,3-galactosyltransferase genes were measured by quantitative RT-PCR.

The results are shown in Table 3.

Table 3. β1,3-galactosyltransferase activity toward agalacto LNnT as a substrate and expression of β3Gal-T transcripts in each kind of cells

| Cell | % activity | Expression of β3Gal-T transcripts (β3Gal-T/β-actin × $10^3$) | | | | |
|---|---|---|---|---|---|---|
| | | β3Gal-T5 | β3Gal-T1 | β3Gal-T2 | β3Gal-T3 | β3Gal-T4 |
| Namalwa-mock | <1 | <0.01 | <0.01 | 2.1 | <0.01 | 1.4 |
| Namalwa-3GT1 | <1 | <0.01 | 56 | 2.1 | <0.01 | 1.4 |
| Namalwa-3GT2 | <1 | <0.01 | <0.01 | 38 | <0.01 | 1.4 |
| Namalwa-3GT3 | <1 | <0.01 | <0.01 | 2.1 | 42 | 1.4 |
| Namalwa-3GT4 | <1 | <0.01 | <0.01 | 2.1 | <0.01 | 43 |
| Namalwa-3GT5 | 100 | 35 | <0.01 | 2.1 | <0.01 | 1.4 |
| HCT-3GT5L | 18 | 5 | <0.01 | <0.01 | 2.2 | 0.1 |
| HCT-3GT5H | 48 | 16 | <0.01 | <0.01 | 2.2 | 0.1 |
| Colo205 | 40 | 3.5 | <0.01 | <0.01 | 0.05 | 4.6 |
| SW1116 | 22 | 1.4 | <0.01 | 0.3 | 0.6 | 3.2 |
| HCT-15 | <1 | <0.01 | <0.01 | <0.01 | 2.2 | 0.1 |
| Capan-2 | 23 | 1.2 | <0.01 | <0.01 | 1.9 | 2.3 |
| MKN45 | <1 | <0.01 | 0.04 | 0.5 | 66 | <0.01 |
| PC-1 | <1 | <0.01 | 27 | 0.3 | <0.01 | 0.2 |

It was confirmed that the amounts of transcripts of corresponding β1, 3-galactosyltransferase genes are higher in the cells having the respective expression plasmids introduced therein than in the cells having only the vector introduced therein.

Said transformed cells were suspended in a solution [20 mmol/l HEPES (pH 7.2), 2% Triton X-100] and sonicated in a short time to prepare a cell lysate solution.

/The protein concentration of said cell lysate solution was determined using a micro-BCA protein assay reagent kit (a product of PIERCE).

Said cell lysate solution was used to measure 1,3-galactosyltransferase activity.

Preparation of the pyridylaminated sugar chain substrate and measurement of the activity were conducted according to known methods [Japanese Published Unexamined Patent Application Nos. 181759/94 and 823021/94, J. Biol. Chem., 269, 14730–14737 (1994)].

Specifically, the activity was measured by identifying a product by high performance liquid chromatography (HPLC) after reaction at 37° C. for 2 hours in 10 μl assay solution [14 mmol/l HEPES (pH 7.4), 75 mmol/l UDP-Gal (a product of SIGMA), 11 μmol/l $MnCl_2$, 0.01% Triton X-100, 25 μmol/l pyridylaminated sugar chain substrate, and the above cell lysate solution].

The substrate (agalacotoLNnT, GlcNAcβ1-3Galβ1-4Glc) was obtained by treatment, with β-galactosidase, of lacto-N-neotetraose (Galβ1-4GlcNAcβ1-3Galβ1-4Glc, hereinafter abbreviated to LNnT) fluorescence-labeled with aminopyridine, to remove the terminal galactose residue.

AgalactoLNnT was prepared by adding 100 mU of β-galactosidase (a product of Seikagaku Kogyo Co., Ltd.) to about 60 nmol LNnT fluorescence-labeled with aminopyridine, reacting them at 37° C. for 16 hours and heat treatment thereof at 100° C. for 5 minutes to inactivate the β-galactosidase.

As the standard, LNnT fluorescence-labeled with aminopyridine or Lacto-N-tetraose (Galβ1-3GlcNAcβ1-3Galβ1-4Glc, hereinafter abbreviated to LNT) fluorescence-labeled with aminopyridine was used. LNnT and LNT were purchased from Oxford Glico Systems Ltd. Fluorescence-labeling of the oligosaccharides was carried out in a usual manner [Agric. Biol. Chem., 54, 2169 (1990)].

After the reaction with an assay solution containing or not containing UDP-Gal (sugar donor), the reaction solution was analyzed by HPLC, and a peak appearing in only the assay solution containing UDP-Gal was assumed to be a product.

After the reaction, the assay solution was treated at 100° C. for 3 minutes and centrifuged at 10,000×g for 5 minutes to give a supernatant, and its aliquot was subjected to HPLC. HPLC was conducted at an elution temperature of 25° C. at a flow rate of 1 ml/min using a TSK-gel ODS-80Ts column (4.6×300 mm, a product of Tosoh Corporation) and 0.02 mol/l ammonium acetate buffer (pH 4.0) as an eluent.

Detection of the product was conducted using a fluorescence spectrophotometer FP-920 (a product of Nippon Bunko Co., Ltd.) (excitation wavelength, 320 nm; emission wavelength, 400 nm).

The product was identified by comparing its retention time with that of standard sugar chain.

Quantification of the product was conducted by comparing its fluorescence density with that of aminopyridylated lactose as the standard.

The activities of the respective β1,3-galactosyltransferases, relative to the activity (=100) of human β3Gal-T5 are shown in Table 3.

Apparent β1,3-galactosyltransferase activity (LNT synthesis activity) was detected in the cells expressing human β3Gal-T5, but no activity was detected in the cells expressing other β1,3-galactosyltransferases. No activity was detected either in the cells having the control plasmid (pAMo) introduced therein.

In the cells having the respective β1,3-galactosyltransferase expression plasmids introduced therein, the respective β1,3-galactosyltransferase transcripts were expressed to the same degree (Table 3), thus revealing that the GlcNAc β1,3-galactosyltransferase activity (LNT synthesis activity) of human β3Gal-T5 is stronger than those of other GlcNAc β1,3-galactosyltransferases (human β3Gal-T1, human β3Gal-T2, human β3Gal-T3). On the other hand, human β3Gal-T4 is known to have GalNAc β11,3-galactosyltransferase activity, but not GlcNAc β1,3-galactosyltransferase activity.

From the results described above, it was proven that human β3Gal-T5 is a GlcNAc β1,3-galactosyltransferase. Further, the activity of human β3Gal-T5 is stronger than the other GlcNAc β1,3-galactosyltransferases (human β3Gal-T1, human β3Gal-T2, human β3Gal-T3), thus indicating that human β3Gal-T5 is useful for synthesis of type 1 sugar chains such as LNT.

To examine whether the amount of β3Gal-T5 transcript expressed is correlated with GlcNAc β1,3-galactosyltransferase activity (LNT synthesis activity), HCT-15 cells (HCT-3GT5L and HCT-3GT5H) to which the β3Gal-T5 expression plasmid obtained in Example 2 had been introduced, and the colon cancer cell lines (Colo205, SW1116, HCT-15), the pancreatic cancer cell line (Capan-2), the stomach cancer cell line (MKN45) and the lung cancer cell line (PC-1) used in Example 1 were examined for the amount of β3Gal-T5 transcript expressed therein and for activity of GlcNAc β1,3-galactosyltransferase activity (LNT synthesis activity).

The amount of β3Gal-T5 transcript expressed in each kind of cells was measured using the method described in Example 1 or in item (7) in Example 2. GlcNAc β1,3-galactosyltransferase activity (LNT synthesis activity) was measured according to the method described above.

The results are shown in Table 3.

As a result, it was revealed that the amount of β3Gal-T5 transcript expressed is correlated with GlcNAc β1,3-galactosyltransferase activity (LNT synthesis activity). For example, the amount of β3Gal-T5 transcript expressed in HCT-3GT5H was about 3 times as high as that in HCT-3GT5L, and the GlcNAc β1,3-galactosyltransferase activity (LNT synthesis activity) in HCT-3GT5H was also about 3 times as high as that in HCT-3GT5L.

On the other hand, PC-1 expressed a large amount of β3Gal-T1, but GlcNAc β1,3-galactosyltransferase activity (LNT synthesis activity) was not detected. Further, MKN45 expressed a large amount of β3Gal-T3, but GlcNAc β1,3-galactosyltransferase activity (LNT synthesis activity) was not detected.

This result indicates that the GlcNAc β1,3-galactosyktransferase activity (LNT synthesis activity) of β3Gal-T1, and β3Gal-T3 is lower than that of β3Gal-T5, and this agrees with the result of analysis using the above Namalwa cells.

Example 4

Expression of the β3Gal-T5 Gene in Various Organs

Figure 5:
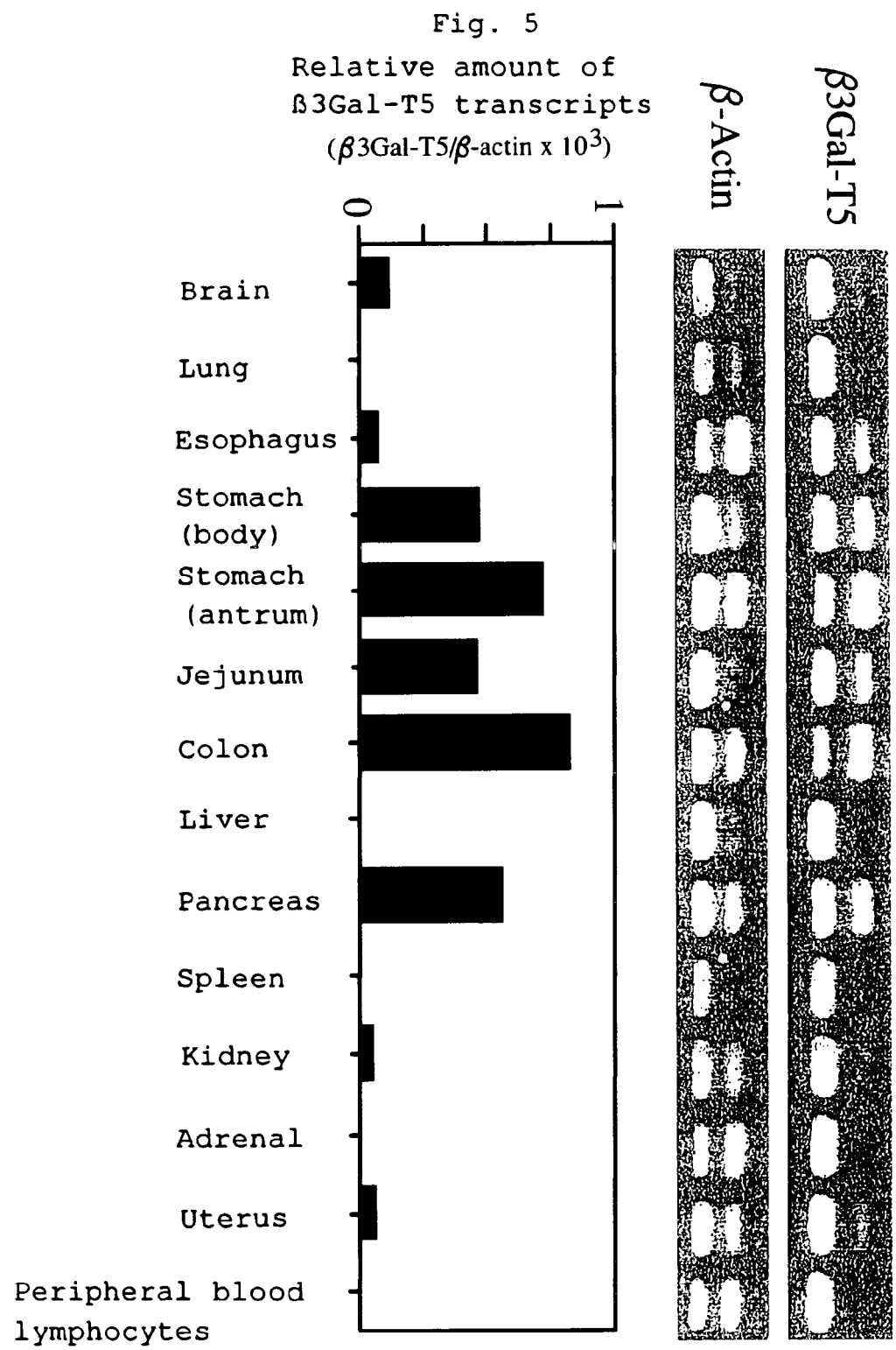
FIG. 5 shows the results of quantification of human β3Gal-T5 transcripts in various human tissues by the quantitative PCR method. The amounts of the human β3Gal-T5 transcripts in various human tissues are expressed as values relative to the amount (=1000) of the β-actin transcript considered to be expressed at a similar degree in any cells.

The β3Gal-T5 transcripts in various human tissues (brain, lung, esophagus, stomach (body), stomach (antrum), jejunum, colon, liver, pancreas, spleen, kidney, adrenal, uterus, peripheral blood lymphocytes) were quantified by RT-PCR in the same manner as in item (7) in Example 2. The amount of the β3Gal-T5 gene transcript in each kind of organs is shown as a value relative to the amount (=1000) of the β-actin transcript (FIG. 5).

It was revealed that the β3Gal-T5 transcripts are significantly expressed in the stomach (body), stomach (antrum), jejunum, colon and pancreas. Further, the β3Gal-T5 transcripts were slightly expressed in the brain, esophagus, kidney and uterus. On the other hand, the β3Gal-T5 transcripts were not expressed in the lung, liver, spleen, adrenal and peripheral blood lymphocytes.

Example 5

Structural Analysis of the βGal-T5 Chromosomal Gene

At present, a large number of human chromosomal genes whose functions are not known are registered in a database. Accordingly, by comparing the sequence of the human cDNA coding for the polypeptide of the present invention with the sequences of human chromosomal genes registered in a database, the human chromosomal gene coding for the polypeptide of the present invention would be identified and its structure would be revealed. If the sequence of a chromosomal gene consistent with the sequence of said cDNA has been registered, the promoter region and exon and intron structures in the chromosomal gene coding for the polypeptide of the present invention can be determined by comparing the sequence of said cDNA with the sequence of said chromosomal gene.

Comparison between the nucleotide sequence of β3Gal-T5 cDNA (SEQ ID NO: 2) and DNA sequences registered in Genome Project Database revealed that since a part of the sequence of Registration No. AF064860 contains the sequence of the cDNA of β3Gal-T5, the βGal-T5 chromosomal gene is located in human chromosome 21q22.3.

For the purpose of revealing the promoter region in the β3Gal-T5 chromosomal gene, the 5'-terminal region of β3Gal-T5 cDNA was obtained from Colo205 cells by the 5' RACE method. The 5' RACE method employed was that described in instructions attached to the kit (5' RACE system, Version 2.0, a product of GIBCO).

First, single-stranded cDNA was synthesized using Colo205-derived mRNA (1 μg) as a template and two synthetic DNAs having the sequences represented by SEQ ID NOS: 22 and 23 as primers. After the synthesis, terminal deoxynucleotidyl transferase was used to add oligo-dC to the 3'-terminus of said cDNA, and then PCR was conducted using synthetic DNA having a dG tail attached to the kit as the forward primer and synthetic DNA having the sequence represented by SEQ ID NO: 24 as the reverse primer.

After heating at 97° C. for 11 minutes, PCR was carried out using 42-cycle reaction, each cycle consisting of reaction at 94° C. for 1 minute, at 55° C. for 1 minute and at 72° C. for 2 minutes.

The amplified fragment was digested with Hind III and SpeI and then subcloned between HindIII-SpeI sites in pBluescript SK(–). The five plasmids thus obtained were sequenced, and as a result, it was revealed that the origin of transcription of the β3Gal-T5 chromosomal gene in Colo205 cells is a base at the 85153-position in Registration No. AF064860 mentioned above.

Accordingly, it was revealed that the region upstream from this origin of transcription is a promoter region functioning at least in Colo205 cells.

The promoter region (including the transcription-regulating region) on the β3Gal-T5 chromosomal gene is estimated to be a 5-kb region (sequence of 1 to 5000 in the nucleotide sequence represented by SEQ ID NO: 3) upstream from the origin of transcription.

A 1-kb region (sequence of 4001 to 5000 in the nucleotide sequence represented by SEQ ID NO: 3) upstream from the origin of transcription was analyzed for the presence of a consensus sequence for a binding sequence of a transcription factor by using a TFSEARCH (transcription factor search) program.

No TATA box was present upstream of the origin of transcription, but it is estimated that two CdxA sites, one AP-1 site and one MZF-1 (myeloid zinc finger 1 protein) site are present in a 150-bp region upstream of the origin of transcription.

The promoter region can also be experimentally specified by introducing a plasmid having a reporter gene ligated downstream from said region into cells expressing β3Gal-T5 and examining whether the reporter gene is expressed or not.

For further analyzing exon and intron regions in the β3Gal-T5 chromosomal gene, whether isoforms of β3Gal-T5 cDNA are present or not was examined by the PCR method.

numbers in SEQ ID NO: 3. In Table 4, the nucleotide sequence indicated by capital letters is an exon region, the nucleotide sequence indicated by small letters is an intron region.

The structure of the β3Gal-T5 chromosomal gene (positions and sequences of the exon and intron regions), its position on the chromosome, and the position and sequence of the promoter region of the β3Gal-T5 chromosomal gene could be specified for the first time by revealing the structure and functions of the β3Gal-T5 cDNA according to the present invention.

TABLE 4

| | Exon/intron junctions of the β 3Gal-T5 chromosomal gene | | | |
|---|---|---|---|---|
| Exon No. | Nucleotide sequence No. in SEQ ID NO:3 | Length (bp) | Sequence of splice acceptor site | Sequence of splice donor site |
| exon1 | 5001–5273 | 273 | — | CTGTCACGgtatttcc (SEQ ID NO:38) |
| exon1' | 5001–5140 | 140 | — | CCAAGCAGgtttctgg (SEQ ID NO:39) |
| exon2 | 5459–5567 | 109 | ctctctagAGAACCCT (SEQ ID NO:40) | GTTTGGAGgtagggct (SEQ ID NO:41) |
| exon3 | 7427–7586 | 160 | tttcctagTGATTCCT (SEQ ID NO:42) | AGCAAAAAgtgagtta (SEQ ID NO:43) |
| exon4 | 8234–10562 | 2329 | cctttcagATGGCTTT (SEQ ID NO:44) | |

PCR was carried out using the Colo205 cell-derived single-stranded cDNA prepared in Example 1 as a template and synthetic DNAs having the sequences represented by SEQ ID NOS: 22 and 25 as primers.

After heating at 97° C. for 11 minutes, PCR was carried out using 42-cycle reaction, each cycle consisting of reaction at 94° C. for 1 minute, at 55° C. for 1 minute and at 72° C. for 2 minutes.

Figure 6:
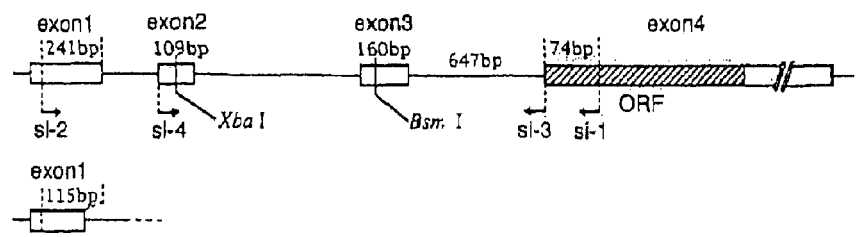
FIG. 6, A shows the structure of human β3Gal-T5 chromosomal gene. Four exons are shown by square and introns by line. An XbaI site is present in exon 2, and a BsmI site is present in exon 3. The coding region (open reading frame) is shown by oblique line. The positions of primers. (si-1, si-2, si-3, si-4) used for analysis of isoforms of human β3Gal-T5 cDNA are shown by arrow.
Figure 6:
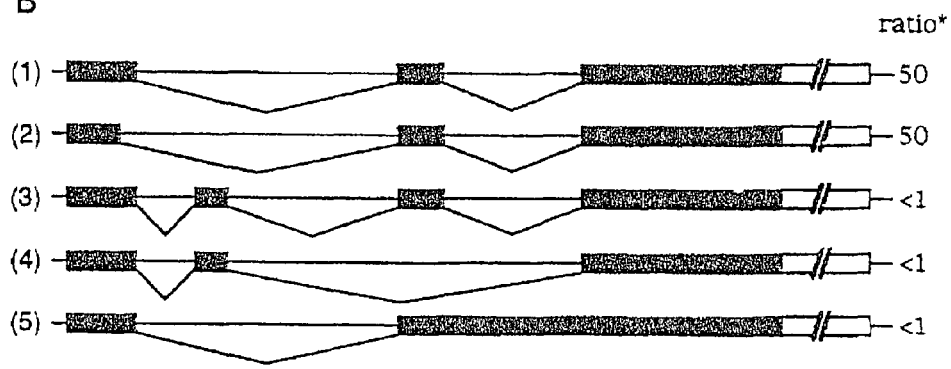
Figure 6:
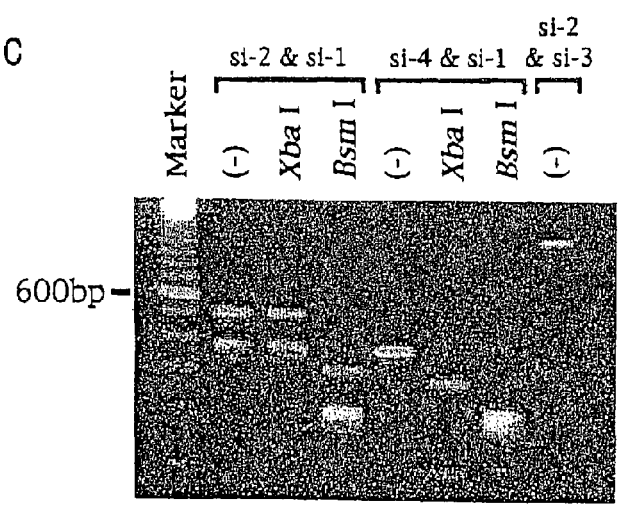

The amplified fragment was digested with HindIII and then subcloned into HindIII site in pBluescript SK(−). The plasmids thus obtained were determined for their nucleotide sequences, and as a result, it was revealed that at least five β3Gal-T5 cDNA isoforms are present in Colo205 cells (FIG. 6).

The proportion of the expression levels of the respective isoforms, as determined by comparing the amounts of the PCR-amplified fragments corresponding to the respective isoforms, was that isoform 1 is 50%, isoform 2 is 50%, and isoforms 3, 4 and 5 are 1% or less, respectively.

The PCR-amplified fragment corresponding to each isoform was specified by the size of the amplified fragment and by treatment with restriction enzyme (XbaI or BsmI).

The above results revealed that the β3Gal-T5 chromosomal gene comprises 4 exons and 3 introns. The sequence of the promoter region (including transcription-regulating region) of the β3Gal-T5 chromosomal gene and the sequence of the 3Gal-T5 chromosomal gene are represented by SEQ ID NO: 3. The sequence of the promoter region (including transcription-regulating region) of the β3Gal-T5 chromosomal gene is a 1 to 5000-bp in the nucleotide sequence represented by SEQ ID NO: 3. The sequence of the β3Gal-T5 chromosomal gene is a 5001-to 10562-bp in the nucleotide sequence represented by SEQ ID NO: 3. The positions of the exons and introns in the β3Gal-T5 chromosomal gene are shown in Table 4 by using the nucleotide

INDUSTRIAL APPLICABILITY

According to the present invention, there can be provided a novel polypeptide having β1,3-galactosyltransferase activity involved in the synthesis of type 1 sugar chains in cancer cells in the digestive system, such as colon cancer cells, pancreatic cancer cells, etc., a process for producing said polypeptide, a DNA coding for said polypeptide, a recombinant vector comprising said DNA integrated therein, a transformant carrying said recombinant vector, an antibody recognizing said polypeptide, a quantification method and an immunostaining method for the polypeptide of the present invention by use of said antibody, a process for producing type 1 sugar chain-containing sugar chains and complex carbohydrates containing said sugar chains by use of said polypeptide, a process for producing type 1 sugar chain-containing sugar chains and complex carbohydrates containing said sugar chains by use of a transformant carrying said recombinant vector, a method for screening a substance altering expression of a gene coding for said polypeptide, a method for screening a substance altering activity of said polypeptide, a method for diagnosis of diseases such as colon cancers, pancreatic cancers and stomach cancers by use of said DNA or said antibody, and a method for treating diseases such as colon cancers, pancreatic cancers and stomach cancers by use of said DNA, said substance altering expression of a gene coding for the polypeptide, or said substance altering the activity of the polypeptide.

| SEQUENCE LISTING FREE TEXT |
|---|
| SEQ ID NO: 4 Description of Artificial Sequence: Synthetic DNA |
| SEQ ID NO: 5 Description of Artificial Sequence: Synthetic DNA |

SEQUENCE LISTING FREE TEXT

| | |
|---|---|
| SEQ ID NO: 6 | Description of Artificial Sequence: Synthetic DNA |
| SEQ ID NO: 7 | Description of Artificial Sequence: Synthetic DNA |
| SEQ ID NO: 8 | Description of Artificial Sequence: Synthetic DNA |
| SEQ ID NO: 9 | Description of Artificial Sequence: Synthetic DNA |
| SEQ ID NO: 10 | Description of Artificial Sequence: Synthetic DNA |
| SEQ ID NO: 11 | Description of Artificial Sequence: Synthetic DNA |
| SEQ ID NO: 12 | Description of Artificial Sequence: Synthetic DNA |
| SEQ ID NO: 13 | Description of Artificial Sequence: Synthetic DNA |
| SEQ ID NO: 14 | Description of Artificial Sequence: Synthetic DNA |
| SEQ ID NO: 15 | Description of Artificial Sequence: Synthetic DNA |
| SEQ ID NO: 16 | Description of Artificial Sequence: Synthetic DNA |
| SEQ ID NO: 17 | Description of Artificial Sequence: Synthetic DNA |
| SEQ ID NO: 18 | Description of Artificial Sequence: Synthetic DNA |
| SEQ ID NO: 19 | Description of Artificial Sequence: Synthetic DNA |
| SEQ ID NO: 20 | Description of Artificial Sequence: Synthetic DNA |
| SEQ ID NO: 21 | Description of Artificial Sequence: Synthetic DNA |
| SEQ ID NO: 22 | Description of Artificial Sequence: Synthetic DNA |
| SEQ ID NO: 23 | Description of Artificial Sequence: Synthetic DNA |
| SEQ ID NO: 24 | Description of Artificial Sequence: Synthetic DNA |
| SEQ ID NO: 25 | Description of Artificial Sequence: Synthetic DNA |

What is claimed is:

1. An isolated polypeptide consisting of the amino acid sequence by SEQ ID NO: 1.

2. An isolated polypeptide comprising the sequence of amino acids 31 to 310 in the amino acid sequence SEQ ID NO:1.

3. An isolated polypeptide comprising the amino acid sequence SEQ ID NO: 1.

4. An isolated DNA selected from the group consisting of:
   (a) DNA coding for the polypeptide described in claims 1, 2 or 3,
   (b) DNA comprising the nucleotide sequence of 402 to 1331 in the nucleotide sequence SEQ ID NO: 2, and
   (c) DNA comprising the nucleotide sequence of 492 to 1331 in the nucleotide sequence SEQ ID NO: 2.

5. A recombinant DNA prepared by integrating the DNA described in claim 4 into a vector.

6. A recombinant DNA according to claim 5 which is plasmid pAMo-3GT5 or plasmid pBS-3GT5 (FERM BP-6645).

7. A non-human transformant transformed with the DNA described in claim 4.

8. A transformant according to claim 7 wherein the host is selected from the group consisting of a microorganism, an animal cell, a plant cell, an insect cell and a non-human transgenic animal.

9. A transformant according to claim 8 wherein the host is a microorganism belonging to the genus *Escherichia*.

10. A transformant according to claim 8 wherein the host is an animal cell selected from the group consisting of a mouse myeloma cell, a rat myeloma cell, a mouse hybridoma cell, a CHO cell, a BHK cell, an African green monkey kidney cell, a Namalwa cell, a Namalwa KJM-1 cell, a human embryonic kidney cell and a human leukemia cell.

11. A transformant according to claim 8 wherein the host is an insect cell selected from the group consisting of a *Spodoptera frugiperda* ovarian cell, a *Trichoplusia ni* ovarian cell and a silkworm ovarian cell.

12. A process for producing a polypeptide, which comprises culturing a non-human transformant transformed with a recombinant DNA prepared by integrating DNA coding for the polypeptide of any one of claims 1, 2 or 3 into a vector in a medium to thereby form and accumulate said polypeptide in culture, and collecting said polypeptide from said culture.

13. A process for producing a polypeptide, which comprises breeding a non-human transgenic animal transfected with a recombinant DNA prepared by integrating DNA coding for the polypeptide of any one of claims 1, 2 or 3 into a vector to thereby form and accumulate said polypeptide in said animal, and collecting said polypeptide from said animal.

14. A process according to claim 13 wherein formation and accumulation occur in animal milk.

15. A process for producing a polypeptide, which comprises synthesizing the polypeptide of any one of claims 1, 2 or 3 in an in vitro transcription-translation system using DNA coding for said polypeptide.

16. A process for producing a reaction product having galactose, which comprises:
    selecting a polypeptide according to any one of claims 1, 2 or 3 as an enzyme source;
    providing (a) said enzyme source, (b) an acceptor substrate selected from the group consisting of: i) N-acetylglucosamine (GlcNAc), ii) an oligosaccharide having N-acetylglucosamine residue at the non-reducing terminus thereof, and iii) a complex carbohydrate having N-acetylglucosamine residue at the non-reducing terminus thereof, and (c) uridine-5'-diphosphate galactose in an aqueous medium to thereby form and accumulate said reaction product in the aqueous medium, wherein the galactose is transferred via β1,3-linkage to N-acetylglucosamine or N-acetylglucosamine residue of said acceptor substrate; and
    collecting said reaction product from said aqueous medium.

17. A process for producing a reaction product having galactose, which comprises:
    selecting a polypeptide according to any of claims 1, 2 or 3 as an enzyme source;
    providing (a) said enzyme source, (b) an acceptor substrate selected from the group consisting of: i) glucose, ii) an oligosaccharide having glucose residue at the non-reducing terminus thereof, and iii) a complex carbohydrate having glucose residue at the non-reducing terminus thereof, and (c) uridine-5'-diphosphate galactose in an aqueous medium to thereby form and accumulate said reaction product in the aqueous medium, wherein the galactose is transferred via β1,3-linkage to glucose or glucose residue of said acceptor substrate; and
    collecting said reaction product from said aqueous medium.

18. A process for producing a sugar chain or a complex carbohydrate, which comprises culturing a transformant of claim 8 in a medium to thereby form and accumulate a sugar chain having galactose transferred via β 1,3-linkage to N-acetylglucosamine, N-acetylglucosamine residue, glucose or glucose residue thereof or a complex carbohydrate containing said sugar chain in the culture, and collecting said sugar chain or said complex carbohydrate from said culture.

19. A process for producing a sugar chain or a complex carbohydrate, which comprises breeding the non-human transgenic animal of claim 8 to thereby form and accumulate in said animal a sugar chain having galactose transferred via β 1,3-linkage to N-acetylglucosamine, N-acetylglucosamine residue, glucose or glucose residue thereof or a complex carbohydrate containing said sugar chain, and collecting said sugar chain or said complex carbohydrate from said animal.

20. A process according to claim 16 wherein the complex carbohydrate is a complex carbohydrate selected from the group consisting of a glycoprotein, a glycolipid, a proteoglycan, a glycopeptide, a lipopolysaccharide, a peptidoglycan and a glycoside which is a steroid compound with a sugar chain.

21. A process according to claim 19 wherein formation and accumulation occur in animal milk.

22. A method for determining the expression level of a gene encoding a polypeptide (i) consisting of the amino acid sequence SEQ ID NO: 1, (ii) comprising the sequence of amino acids 31 to 310 in SEQ ID NO: 1 or (iii) comprising the amino acid sequence represented by SEQ ID NO: 1, which comprises hybridization using DNA according to claim 4.

23. A method for determining the expression level of DNA according to claim 4, which comprises conducting polymerase chain reaction using an oligonucleotide comprising a consecutive 5 to 60 nucleotide sequence of said DNA or DNA complementary thereto.

24. A method for detecting cancers or cancer metastasis, which comprises conducting the method of claim 23 and correlating the expression level to that obtained with cancer or cancer metastasis.

25. A method for inhibiting transcription of DNA according to claim 4 or translation of its corresponding mRNA, which comprises blocking expression or translation using an oligonucleotide comprising a consecutive 5 to 60 nucleotide sequence of DNA complementary thereto.

26. A method for immunological detection of a polypeptide according to claims 1, 2 or 3, which comprises applying an antibody thereto and determining an antigen-antibody reaction.

27. A method for screening a compound, which comprises contacting a transformant according to claim 8 which expresses said isolated DNA with a test sample and determining the amount of protein expressed.

28. A process according to claim 17 wherein the complex carbohydrate is a complex carbohydrate selected from the group consisting of a glycoprotein, a glycolipid, a proteoglycan, a glycopeptide, a lipopolysaccharide, a peptidoglycan and a glycoside which is a steroid compound with a sugar chain.

29. A process according to claim 18 wherein the complex carbohydrate is a complex carbohydrate selected from the group consisting of a glycoprotein, a glycolipid, a proteoglycan, a glycopeptide, a lipopolysaccharide, a peptidoglycan and a glycoside which is a steroid compound with a sugar chain.

30. An insolated DNA that hybridizes under stringent conditions with the DNA of claim 4 and encodes a polypeptide having ⊕1,3-galactosyltransferase activity capable of synthesizing Gal ⊕1-3GlcNAc structure, wherein the stringent conditions comprise hybridizing the DNA at 65° C. in the presence of 0.7 to 1.0 mol/L NaCl using the filter on which a DNA prepared from colonies or plaques is immobilized and then washing the filter at 65° using 0.1 to 2-fold concentration of saline-sodium citrate solution.

* * * * *

UNITED STATES PATENT AND TRADEMARK OFFICE
CERTIFICATE OF CORRECTION

| | |
|---|---|
| PATENT NO. | : 7,241,605 B1 |
| APPLICATION NO. | : 09/914152 |
| DATED | : July 10, 2007 |
| INVENTOR(S) | : Hisashi Narimatsu et al. |

It is certified that error appears in the above-identified patent and that said Letters Patent is hereby corrected as shown below:

ON TITLE PAGE AT (75) INVENTOR

"Katsutoshi Sasaki, Machida (JP)" should read --Katsutoshi Sasaki, Sagamihara (JP)--.

ON TITLE PAGE AT (56) OTHER PUBLICATIONS

In "Ishhiki, et al., "Homo . . ."": "Ishhiki," should read --Isshiki,--.

COLUMN 1

Line 9, "etc." should read --etc.,--;
Line 52, "i.e." should read --i.e.,--; and
Line 64, "No. 181759/94," should read --No. 6-181759,--.

COLUMN 2

Line 15, "1,3-galactosyl-" should read --β1,3-galactosyl- --; and
Line 27, "in" (second occurrence) should read --in the--.

COLUMN 3

Line 1, "etc." should read --etc.,--;
Line 43, "etc." should read --etc.,--; and
Line 53, "etc." should read --etc,--.

COLUMN 4

Line 5, "3Galp1-4Glc" should read --3Galβ1-4Glc--; and
Line 46, "β11,3-glactosyltransferase" should read --β1,3-galactosyltransferase--.

COLUMN 6

Line 9, "11,3-" should read --β1.3- --; and
Line 62, "oligonicleotide" should read --oligonucleotide--.

UNITED STATES PATENT AND TRADEMARK OFFICE
CERTIFICATE OF CORRECTION

PATENT NO. : 7,241,605 B1
APPLICATION NO. : 09/914152
DATED : July 10, 2007
INVENTOR(S) : Hisashi Narimatsu et al.

It is certified that error appears in the above-identified patent and that said Letters Patent is hereby corrected as shown below:

COLUMN 8

Line 39, "sialyl Lewis" should read --sialyl-Lewis--;
Line 39, "chains. The" should read --chains. ¶ The--;
Line 41, "etc." should read --etc.,--;
Line 53, "336963/93)]." should read --5-336963)].--; and
Line 64, "etc." should read --etc.,--.

COLUMN 9

Line 16, "P1,3-galactosyltransferases," should read --β1,3-galactosyltransferases,--.

COLUMN 10

Line 18, "an" should read --any--;
Line 23, "22979/91," should read --3-22979,--;
Line 27, "336963/93]," should read --5-336963],--;
Line 28, "227075/" should read --2-227075),--;
Line 29, "90), etc." should read --etc.,--;
Line 38, "227075/90)," should read --2-227075),--; and
Line 57, "the" (second occurrence) should be deleted.

COLUMN 11

Line 52, "etc." should read --etc.,--.

COLUMN 13

Line 6, "22979/91," should read --3-22979,--;
Line 6, "4,686,191," should read --4,686,191;--;
Line 7, "094," should read --094;--;
Line 19, "etc." should read --etc.,--;
Line 20, "pen P" should read --penP--;
Line 23, "etc." should read --etc.,--; and
Line 63, "etc." should read --etc.,--.

UNITED STATES PATENT AND TRADEMARK OFFICE
CERTIFICATE OF CORRECTION

PATENT NO. : 7,241,605 B1
APPLICATION NO. : 09/914152
DATED : July 10, 2007
INVENTOR(S) : Hisashi Narimatsu et al.

It is certified that error appears in the above-identified patent and that said Letters Patent is hereby corrected as shown below:

COLUMN 14

Line 22, "22979/91," should read --3-22979,--;
Line 26, "336963/93)," should read --5-336963), and--;
Line 28, "227075/90)." should read --2-227075).--;
Line 34, "a" (second occurrence) should read --α--; and
Line 56, "227075/90)," should read --2-227075),--.

COLUMN 15

Line 22, "227075/90)," should read --2-227075),--;
Line 30, "227075/90)," should read --2-227075),--; and
Line 43, "e.g." should read --e.g.,--.

COLUMN 16

Line 32, "β1, 3-galactosyltransferase" should read --β1,3-galactosyltransferase--.
Line 44, "etc." should read --etc.,--; and
Line 57, "etc." should read --etc.,--.

COLUMN 17

Line 38, "the" (second occurrence) should be deleted.

COLUMN 18

Line 22, "181759/" should read --6-181759],--;
Line 23, "94.]," should be deleted; and
Line 53, "336963/93," should read --5-336963,--.

COLUMN 19

Line 15, "227075/90." should read --2-227075.--.

COLUMN 20

Line 8, "336963/93" should read --5-336963--; and
Line 46, "181759/94," should read --6-181759,--.

UNITED STATES PATENT AND TRADEMARK OFFICE
CERTIFICATE OF CORRECTION

PATENT NO.      : 7,241,605 B1
APPLICATION NO. : 09/914152
DATED           : July 10, 2007
INVENTOR(S)     : Hisashi Narimatsu et al.

It is certified that error appears in the above-identified patent and that said Letters Patent is hereby corrected as shown below:

COLUMN 22

Line 6, "1,3-" should read --β1,3- --; and
　　Line 63, "etc." should read --etc.,--.

COLUMN 23

Line 16, "etc." should read --etc.,--.

COLUMN 25

Line 51, "human." should read --humans.--;
　　Line 54, "mouse," should read --mice,--;
　　Line 54, "human." should read --humans.--; and
　　Line 59, "etc." should read --etc.,--.

COLUMN 26

Line 63, "a1,3-fucosyltrans-" should read -- α1,3-fucosyltrans- --.

COLUMN 29

Line 23, "181759/94," should read --6-181759,--.

COLUMN 30

Line 50, "etc." should read --etc.,--;
　　Line 53, "etc." should read --etc.,--; and
　　Line 56, "etc." should read --etc.,--.

COLUMN 31

Line 53, "(HCT-3 GT5H)" should read --(HCT-3GT5H)--.

COLUMN 32

Line 62, "181759/94," should read --6-181759,--; and
　　Line 64, "β1, 3-glactosyltransferase" should read --β1,3-glactosyltransferase--.

UNITED STATES PATENT AND TRADEMARK OFFICE
CERTIFICATE OF CORRECTION

PATENT NO. : 7,241,605 B1
APPLICATION NO. : 09/914152
DATED : July 10, 2007
INVENTOR(S) : Hisashi Narimatsu et al.

It is certified that error appears in the above-identified patent and that said Letters Patent is hereby corrected as shown below:

COLUMN 34

Line 10, "β33Gal-T4" should read --β3Gal-T4--;
Line 17, "181759/94." should read --6-181759.--;
Line 36, "181759/94]." should read --6-181759].--;
Line 42, "β3Gal-T1," should read --β3Gal-T1--;
Line 58, "181759/94]." should read --6-181759].--; and
Line 61, "(pH8.3)," should read --(pH 8.3),--.

COLUMN 35

Line 11, "Nos:" should read --NOS:--; and
Line 65, "β3-actin" should read --β-actin--.

COLUMN 37

Line 10, "referred" should read --referred to--;
Line 11, "to" should read --as--;
Line 22, "fragment" should read --fragments--;
Line 23, "was" should read --were--;
Line 27, "336963/93)]" should read --5-336963)]--;
Line 60, "byQiagen," should read --by Qiagen,--; and
Line 60, "cDNAwas" should read --cDNA was--.

COLUMN 40

Line 15, "181759/94]," should read --6-181759],--;
Line 28, "FERMBP-6645" should read --FERM BP-6645--;
Line 63, "therein(FIG. 3, A)." should read --therein (FIG. 3, A).--; and
Line 65, "3Gal-T5" should read --β3Gal-T5--.

COLUMN 42

Line 58, "β11,3-galactosyltransferase" should read --β1,3-galactosyltransferase--;
Line 59, "β1,3Gal-T3)" should read --β3Gal-T3)--;
Line 61, "(β1,3Gal-T1," should read --β3Gal-T1,--; and
Line 65, "11,3-galactosyl-" should read --β1,3-galactosyl- --.

UNITED STATES PATENT AND TRADEMARK OFFICE
CERTIFICATE OF CORRECTION

PATENT NO. : 7,241,605 B1
APPLICATION NO. : 09/914152
DATED : July 10, 2007
INVENTOR(S) : Hisashi Narimatsu et al.

It is certified that error appears in the above-identified patent and that said Letters Patent is hereby corrected as shown below:

COLUMN 43

Line 20, "181759/94." should read --6-181759.--;
    Line 24, "Example 3" should read --Example 2--;
    Line 28, "1,3-galactosyltransferase" should read --β1,3-galactosyltransferase--;
    Line 55, "β1, 3-glactosyltransferase" should read --β1,3-galactosyltransferase--;
    Line 63, "/The" should read --The--; and
    Line 66, "1,3-galac-" should read --β1,3-galac- --.

COLUMN 44

Line 4, "181759/94 and 823021/94," should read --6-181759 and 6-823021,--.

COLUMN 45

Line 2, "β11,3-galactosyltrans-" should read --β1,3-galactosyltrans- --;
    Line 43, "β1,3-galactosyk-" should read --β1,3-galactosyl- --;
    Line 44, "β3Gal-T1," should read --β3Gal-T1--; and
    Line 59, "organs" should read --organ--.

COLUMN 46

Line 3, "βGal-T5" should read--β3Gal-T5--;
    Line 24, "βGal-T5" should read --β3Gal-T5--; and
    Line 45, "Hind III" should read --HindIII--.

COLUMN 47

Line 59, "3Gal-T5" should read --β3Gal-T5--; and
    Line 64, "5001-to" should read --5001- to--.

COLUMN 79

Line 3, "by" should be deleted.

COLUMN 80

Line 5, "via P1,3-" should read --via β1,3- --;
    Line 30, "β 1,3-linkage" should read --β1,3-linkage--; and
    Line 39, "β 1,3-linkage" should read --β1,3-linkage--.

UNITED STATES PATENT AND TRADEMARK OFFICE
CERTIFICATE OF CORRECTION

PATENT NO. : 7,241,605 B1
APPLICATION NO. : 09/914152
DATED : July 10, 2007
INVENTOR(S) : Hisashi Narimatsu et al.

It is certified that error appears in the above-identified patent and that said Letters Patent is hereby corrected as shown below:

<u>COLUMN 82</u>

Line 7, "insolated" should read --isolated--;
Line 10, "⊕1,3-galactosyltransferase" should read --β1,3-galactosyltransferase--;
Line 11, "⊕1-3GlcNAc" should read --β1-3GlcNAc--; and
Line 15, "65° using" should read --65°C using--.

Signed and Sealed this

Fourth Day of December, 2007

JON W. DUDAS
*Director of the United States Patent and Trademark Office*